US008658596B2

(12) United States Patent
Fallon et al.

(10) Patent No.: US 8,658,596 B2

(45) Date of Patent: Feb. 25, 2014

(54) BIGLYCAN AND RELATED THERAPEUTICS AND METHODS OF USE

(75) Inventors: Justin R. Fallon, Brooklyn, CT (US); Mark A. Bowe, Damascus, MD (US); Beth McKechnie, Franklin, MA (US); Michael Rafii, San Diego, CA (US); Alison Amenta, Pawtucket, RI (US); Mary Lynn Mercado, Robbinsville, NJ (US); Hiroki Hagiwara, Tokyo (JP)

(73) Assignee: Brown University Research Foundation, Providence, RI (US)

( * ) Notice: Subject to any disclaimer, the term of this patent is extended or adjusted under 35 U.S.C. 154(b) by 0 days.

(21) Appl. No.: 12/881,891

(22) Filed: Sep. 14, 2010

(65) Prior Publication Data

US 2011/0183910 A1 Jul. 28, 2011

Related U.S. Application Data

(60) Continuation of application No. 12/072,008, filed on Feb. 22, 2008, now Pat. No. 7,816,322, which is a division of application No. 10/868,247, filed on Jun. 14, 2004, now Pat. No. 7,335,637, which is a division of application No. 09/715,836, filed on Nov. 17, 2000, now Pat. No. 6,864,236.

(60) Provisional application No. 60/166,253, filed on Nov. 18, 1999.

(51) Int. Cl.

*A61K 38/00* (2006.01)
*C07K 1/00* (2006.01)
*C07K 14/00* (2006.01)

(52) U.S. Cl.

USPC ......... 514/8.3; 514/16.5; 514/17.9; 514/18.2; 514/21.2; 530/350

(58) Field of Classification Search

None

See application file for complete search history.

(56) References Cited

U.S. PATENT DOCUMENTS

| | | | |
|---|---|---|---|
| 5,340,934 | A | 8/1994 | Termine et al. |
| 5,654,270 | A | 8/1997 | Ruoslahti et al. |
| 5,705,609 | A | 1/1998 | Ruoslahti et al. |
| 6,864,236 | B1 | 3/2005 | Fallon et al. |
| 7,335,637 | B2 | 2/2008 | Fallon et al. |
| 7,612,038 | B2 | 11/2009 | Fallon et al. |
| 7,759,314 | B2 | 7/2010 | Fallon et al. |
| 7,816,322 | B2 | 10/2010 | Fallon et al. |
| 8,138,154 | B2 | 3/2012 | Fallon et al. |
| 2004/0063627 | A1 | 4/2004 | Fallon et al. |
| 2005/0043221 | A1 | 2/2005 | Fallon et al. |
| 2005/0059580 | A1 | 3/2005 | Fallon et al. |
| 2008/0274966 | A1 | 11/2008 | Fallon et al. |
| 2010/0130405 | A1 | 5/2010 | Fallon et al. |
| 2011/0053854 | A1 | 3/2011 | Fallon et al. |
| 2012/0245095 | A1 | 9/2012 | Fallon et al. |

FOREIGN PATENT DOCUMENTS

| | | | |
|---|---|---|---|
| EP | 0686397 | | 12/1995 |
| WO | WO-93/10808 | | 7/1993 |
| WO | WO-9513298 | A1 | 5/1995 |
| WO | WO-00/54801 | | 9/2000 |
| WO | WO-01/36475 | A2 | 5/2001 |
| WO | WO-03/015615 | | 2/2003 |
| WO | WO-03/070195 | A2 | 8/2003 |
| WO | WO-2007/123848 | | 11/2007 |
| WO | WO-2008/100789 | | 8/2008 |
| WO | WO-2011/146480 | A1 | 11/2011 |

OTHER PUBLICATIONS

Bianco, P. et al. Expression and Localization of the Two Small Proteoglycans, Biglycan and Decorin, in Developing Human Skeletal and Non-Skeletal Tissues. *J. Histochem. Cytochem* 38, 1549-1563 (Nov. 1990).

Bowe, M. A. et al. The Small Lucine-rich Repeat Proteoglycan Biglycan Binds to Dystroglycan and is Unregulated in Dystphic Muscle. *J. Cell. Biol.* 148, 801-810 (2000).

Chan, Yiu-mo et al. Molecular Organization of Sarcoglycan Complex in Mouse Myotubes in Culture. *J. Cell Bio.* 143, 2033-2044 (Dec. 28, 1998).

Coral-Vasquez, R. et al. Disruption of the Sarcoglycan-Sarcospan Complex in Vascular Smooth Muscle: A Novel Mechanism for Cardiomyopathy and Muscular Dystrophy. *Cell* 98, 465-74 (1999).

Crosbie, Rachelle H. et al. Membrane Targeting and Stabilizatoin of Sarcospan is Mediated by the Sarcoglycan Subcomplex. *J. Cell. Biol.* 145, 159-165 (Apr. 5, 1999).

Ervasti, James M. & Campbell, Kevin P. A Role for the Dystrophin-Glycoprotein Complex as a Transmembrane Linker between Laminin and Actin. *J. Cell Biol.* 122, 809-823 (Aug. 1993).

Ferri, R. T. et al. A Role for Biglycan in Agrin-Induced Postsynaptic Differentiation. *Society for Neuroscience Abstracts* 26 (2000) [Abstract Only].

Fisher, L. W. et al. Deduced Protein Sequence of Bone Small Proteoglycan I (Biglycan) Shows Homology with Proteoglycan II (Decorin) and Several Nonconnective Tissue Proteins in a Variety of Species. *J. Biol. Chem.* 264, 4571 (1989).

Gee, Stephen H. et al. Dystroglycan-a, a Dystrophin-Associated Glycoprotein, is a Functional Agrin Receptor. *Cell* 77, 675-686 (Jun. 3, 1994).

(Continued)

*Primary Examiner* — Olga N Chernyshev

(74) *Attorney, Agent, or Firm* — Ropes & Gray LLP

(57) ABSTRACT

The invention provides compositions and methods for treating, preventing, and diagnosing diseases or conditions associated with an abnormal level or activity of biglycan; disorders associated with an unstable cytoplasmic membrane, due, e.g., to an unstable dystrophin associated protein complex (DAPC); disorders associated with abnormal synapses or neuromuscular junctions, including those resulting from an abnormal MuSK activation or acetylcholine receptor (AChR) aggregation. Examples of diseases include muscular dystrophies, such as Duchenne's Muscular Dystrophy, Becker's Muscular Dystrophy, neuromuscular disorders and neurological disorders.

18 Claims, 16 Drawing Sheets

(56) References Cited

OTHER PUBLICATIONS

Guglieri, et al., "Molecular Etiopathogenesis of Limb Girdle Muscular and Congenital Muscular Dystrophies: Boundaries and Contiguities," Clinica Chimica Acta 361 (2005) 54-79.

Hasenohrl et al., "Facilitation of learning following injection of the chondroitin sulfate proteoglycan biglycan into the vicinity of the nucleu basalis magnocellularis," *Behavioural Brain Research,* 70:59-67 (1995).

Hoch, Werner. Formation of the Neuromuscular Junction: Agrin and its unusual receptors. *Eur. J. Biochem.* 265, 1-10 (1999).

Hocking, A. M. et al. Eukaryotic Expression of Recombinant Biglycan. *Am. Soc. For Biochem & Mol. Biol.* 27, 19571-77 (1996).

Holt, Kathleen H. et al. Functional Rescue of the Sarcoglycan Complex in the BIO 14.6 Hamster Using S-Sarcoglycan Gene Transfer. *Mol. Cell* 1, 841-848 (May 1998).

Ibraghimov-Beslrovanaya et al. Human Dystroglycan: Skeletal Muscle cDNA, Genomic Structure, Origin of Tissue Specific Isoforms and Chromosomal Localization. *Hum. Mol. Genet.* 2, 1651-1657 (1993).

Iozzo, R. Matrix Proteoglycans: From Molecular Design to Cellular Function. *Ann. Rev. Biochem.* 67, 609-652 (1998).

Jarvelainen, Hannu T. et al. Differential Expression of Small Chondroitin/Dermatan Sulfate Proteoglycans, PG-I/Biglycan and PG-II/Decorin, by Vascular Smooth Muscle and Endothelial Cells in Culture. *J. Biol. Chem.* 266, 23274-23281 (Dec. 5, 1991).

Junghans, Ulrich et al. Purification of a Meningeal Cell-derived Chondroitin Sulphate Proteoglycan with Neurotrophic Activity for Brain Neurons and its Identification as Biglycan. *Euro. J. Neurosci.* 7, 2341-2350 (1995).

Khurana, T. S. et al. Interaction of ARIA, a Neuregulin, with the Dystroglycan / Sarcoglycan Complex in Skeletal Muscle. *Mol. Cell. Biol.* 7, 314 (1996).

Krishnan, P. et al. Distinct Secondary Structures of the Leucine-rich Repeat Proteoglycans Decorin and Biglycan. *J. Biol. Chem.* 274, 10945-50 (1999).

Lampe et al., "Collagen VI Related Muscle Disorders," J. Med. Genet. 2005;42;673-685.

Mercado et al., Biglycan regulates the expression and sarcolemmal localization of dystrobrevin, syntrophin, and nNOS. FASEB J. Aug. 2006;20(10):1724-6. Epub Jun. 28, 2006.

O'Toole et al., Alternative splicing of agrin regulates its binding to heparin, α-dystroglycan, and the cell surface. Proc. Natl. Acad. Sci vol., 93 pages. 7369-7374 (1996).

Peat et al., Exclusion of biglycan mutations in a cohort of patients with neuromuscular disorders. Neuromuscul Disord. Aug. 2008;18(8):606-9. Epub Jul. 7, 2008.

Rafii et al., "Interactions of the Proteoglycan Biglycan with the Dystrophin Associated Protein Complex and its Roles in Muscular Dystrophy and Synaptogenesis," *Molecluar Biology of the Cell,* 11:146a (2000).

Sakamoto, Aiji et al. Both hypertrophic and dilated cardiomyopathies are caused by mutation of the same gene, S-sarcoglycan, in hamster: An animal model of disrupted dystrophin-associated glycoprotein complex. *PNAS* 94, 13873-13878 (Dec. 1997).

Speer et al., "Evidence for locus heterogeneity in the Bethlem myopathy and linkage to 2q37," Hum. Mol. Genet. Jul. 1996;5(7):1043-6.

Spence et al., "Muscular dystrophies, the cytoskeleton and cell adhesion," BioEssays 24:542-552, 2002.

Tomoyasu, Hiroshi et al. Identification of haemopoietic biglycan in hyperplastic thymus associated with myasthenia gravis. *J. Neuroimmunology* 89, 59-63 (1998).

Vanegas et al., "Ullrich scleroatonic muscular dystrophy is caused by recessive mutations in collagen type VI," PNAS vol. 98; No. 13, 2001.

Von der Mark et al., "Immunochemistry, genuine size and tissue localization of collagen VI," Eur. J. Biochem. 142(3):493-502, 1984.

Wiberg et al., "Biglycan and Decorin Bind Close to the N-terminal Region of the Collagen VI Triple Helix," J. Biol. Chem., 276;22, 18947-18952, 2001.

Winder, Steven J. The complexitites of dystroglycan. *Trends in Biochem. Sci.* 26, 118-124 (2001).

Amenta et al., "Biglycan Recruits Utrophin to the Sarcolemma and Counters Dystrophic Pathology in MDX Mice," *Proc Natl. Acad. Sci. USA,* 108(2):762-767 (2011).

Ameye, "Mice Deficient in Small Leucine-Rich Proteoglycans: Novel In Vivo Models for Osteoporosis, Osteroarthritis, Ehlers-Danlos Syndrome, Muscular Dystrophy, and Corneal Diseases," *Glycobiology,* 12(9):107R-116R (2002).

Athanasopoulos et al., "Recombinant adeno-associated viral (rAAV) vectors as therapeutic tools for Duchenne muscular dystrophy (DMD)," Gene Therapy 11:S109-S121 (2004).

Balaban et al., "Corticosterois treatment and functional improvement in Duchenne muscular dystrophy: long-term effect," American Journal of Physical Medicine & Rehabilitation / Assoc. of AcAdemic Physiatrists, 84:11 843-850 (2005).

Bonaldo et al., "Collagen VI deficiency induces early onset myopathy in the mouse: an animal model for Bethlem myopathy," Human Molecular Genetics 7:13 2134-2140 (1998).

Brandan et al., "Novel Regulatory Mechanisms for the Proteoglycans Decorin and Biglycan During Muscle Formation and Muscular Dystrophy," *Matrix Biol.,* 27:700-708 (2008).

Brown. "Hybridization Analysis of DNA Blots," Unit 2.10, Current Protocols in Molecular Biology, John Wiley & Sons (2003).

Casar et al., "Transient Up-Regulation of Biglycan During Skeletal Muscle Regeneration: Delayed Fiber Growth Along with Decorin Increase in Biglycan-Deficient Mice," Dev. Biol., 268:358-371 (2004).

Farooqi et al., Effects of Recombinant Leptin Therapy in a Child with Congenital Leptin Deficiency, N. E. Journal of Medicine, 341: 879-884 (1999).

Fukuta et al. "Molecular Cloning and Expression of Chick Chondrocyte Chondroitin 6-Sulfotransferase," *J. Biol. Chem.,* 270(31)18575-18580 (1995).

Gregorevic et al., "Gene therapy for muscular dystrophy—a review of promising progress," Expert Opin Biol Ther., 3(5) 803-14 (2003).

Hammond et al., "PRO-051, an antisense oligonucleotide for the potential treatment of Duchenne muscular dystrophy" Current Opinion in Molecular Therapeutics, 12:4 478-486 (2010).

Hildebrand et al., "Interaction of the Small Intestitial Proteoglycans Biglycan, Decorin and Fibromodulin with Transforming growth Factor Beta," *J. Biochem.,* 302:527-534 (1994).

Hocking et al., "Leucine-rich Repeat Glycoproteins of the Extracellular Matrix," *Matrix Biol.,* 17(1):1-19 (1998).

Hwang et al., "Retrovirally Mediated Overexpression of Gylycosaminoglycan-Deficient Biglycan in Arterial Smooth Muscle Cells Induces Tropoelastin Synthesis and Elastic Fiber Formation in Vitro And in Neointimae after Vascular Injury", Am J. Pathol. 173(6):1919-1928 (2008).

Khan, M.A. "Corticosteroid therapy in Duchenne muscular dystrophy" Journal of the Neurological Sciences, 120:1, 8-14 (1993).

King, W.M. et al. "Orthopedic outcomes of long-term daily corticosteroid treatment in Duchenne muscular dystrophy" Neurology, 68(19): 1607-1613 (2007).

Kobe & Deisenhofer, "The Leucine-Rich Repeat: a Versatile Binding Motif," *Trends Biochem. Sci.,* 19(10):415-421 (1994).

Kresse et al., "Different Usage of the Glycosaminoglycan Attachment Sites of Biglycan," *J. Biol. Chem.,* 276(16):13411-13416 (2001).

Krivickas, L.S. et al. "Single muscle fiber contractile properties in adults with muscular dystrophy treated with MYO-029" Muscle & Nerve, 39:1 309 (2009).

Lamandé et al., "Reduced collagen VI causes Bethlem myopathy: a heterozygous *COL6A1* nonsense mutation results in mRNA decay and functional haploinsufficiency," Human Molecular Genetics, 7:6 (981-989 (1998).

Langton, et al., "Localization of the Functional Domains of Human Tissue Inhibitor of Metalloproteinases-3 and the Effects of a Sorsby's Fundus Dystropy Mutation," The Journal of Biological Chemistry, 273:16778-16781 (1998).

(56) References Cited

OTHER PUBLICATIONS

Lechner et al., “Developmental Regulation of Biglycan Expression in Muscle and Tendon,” Muscle Nerve, 34:347-355 (2006).
Matthews D.J. et al. “Use of corticosteroids in a population-based cohort of boys with Duchenne and Becker muscular dystrophy”, Journal of Child Neurology, 25:11, 1319-1324 (2010).
Moreth et al., “The Proteoglycan Biglycan Regulates Expression of the B Cell Chemoattractant CXCL13 and Aggravates Murine Lupus Nephritis,” *J. Clin. Invest.*, 120(12):4251-4272 (2010).
Nastuk et al., “Expression Cloning and Characterization of NSIST, a Novel Sulfotransferase Expressed by a Subset of Neurons and Postsynaptic Targets,” *J. Neuroscience,* 18(18)7167-7177 (1998).
O’Brien et al., “Smooth Muscle Cell Biglycan Overexpression Results in Increased Lipoprotein Retention on Extracellular Matrix: Implications for the Retention of Lipoproteins in Atherosclerosis,” Altherosclerosis, 177L29-35 (2004).
Rafii et al, “Biglycan Binds to α- and γ-Sarcoglycan and Regulates Their Expression Duing Development,” *J. Cell Physiol.,* 209(2):439-447 (2006).
Rühland et al., The Glycosaminoglycan Chain of Decorin Plays an Important Role in Collagen Fibril Formation at Early Stages of Fibrillogenesis, The FEBS Journal, 274:4246-4255 (2007).
Schaefer et al., “Biological Functions of the Small Leucine-rich Proteoglycans: From Genetics to Signal Transduction,” *J. Biol. Chem.,* 283(31):21305-21309 (2008).
Scott et al., “Crystal Structure of the Biglycan Dimer and Evidence That Dimerization Is Essential for Folding and Stability of Class I Small Leucine-rich Repeat Proteoglycans,” *J. Biol. Chem.*, 281(19):13324-13332 (2006).
Smythe et al., “Altered caveolin-3 expression disrupts PI(3) kinase signaling leading to death of cultured muscle cells,” Experimental Cell Research, 312:15 2816-2825 (2006).
Xu et al., “Targeted Disruption of the Biglycan Gene Leads to an Osteoporosis-Like Phenotype In Mice,” *Nature Genetics,* 20:78-82 (1998).

```
TORPEDO   IQAIEFEDL     LGLGFNEIR
          |||||  |||    ||||  |  ||
HUMAN     IQAIELEDL     LGLGHNQIR
         241      249  258      266

TORPEDO   TSYHGISLFNNPVNYWDVL
            | |||||||||  ||  |
HUMAN     AYYNGISLFNNPVPYWEVQ
         330               348
```

35S-ALPHA-SARC OVERLAY

BIGLYCAN AND RELATED THERAPEUTICS AND METHODS OF USE

CROSS-REFERENCE TO RELATED APPLICATION

This application is a divisional of U.S. application Ser. No. 12/072,008 filed Feb. 22, 2008, which is a divisional of U.S. application Ser. No. 10/868,247 filed on Jun. 14, 2004 and now issued as U.S. Pat. No. 7,335,637, which is a divisional of U.S. application Ser. No. 09/715,836 filed Nov. 17, 2000 and now issued as U.S. Pat. No. 6,864,236, which claims the benefit of U.S. Provisional Application No. 60/166,253 filed Nov. 18, 1999. The entire teachings of the referenced applications are incorporated herein by reference.

STATEMENT OF RIGHTS

This invention was made with Government support under Grants HD23924 and MH53571 awarded by the National Institutes of Health. The U.S. Government has certain rights in this invention.

BACKGROUND OF THE INVENTION

The dystrophin-associated protein complex (DAPC) links the cytoskeleton to the extracellular matrix and is necessary for maintaining the integrity of the muscle cell plasma membrane. The core DAPC consists of the cytoskeletal scaffolding molecule dystrophin and the dystroglycan and sarcoglycan transmembrane subcomplexes. The DAPC also serves to localize key signaling molecules to the cell surface, at least in part through its associated syntrophins (Brenman, et al. (1996) *Cell.* 84: 757-767; Bredt, et al. (1998), *Proc Natl Acad Sci USA.* 95: 14592). Mutations in either dystrophin or any of the sarcoglycans result in muscular dystrophies characterized by breakdown of the muscle cell membrane, loss of myofibers, and fibrosis (Hoffman, et al. 1987. *Cell.* 51: 919; Straub and Campbell (1997) *Curr Opin Neurol.* 10: 168). Moreover, mutations in the extracellular matrix protein laminin-α2, which associates with the DAPC on the cell surface, are the basis of a major congenital muscular dystrophy (Helbling-Leclerc, et al. (1995) *Nat Genet.* 11: 216).

The α-/β-dystroglycan subcomplex forms a critical structural link in the DAPC. The transmembrane β-dystroglycan and the wholly extracellular α-dystroglycan arise by proteolytic cleavage of a common precursor (Ibraghimov, et al. (1992) *Nature* 355: 696; Bowe, et al. (1994) *Neuron* 12: 1173). The cytoplasmic tail of β-dystroglycan binds dystrophin, while the highly glycosylated, mucin-like α-dystroglycan binds to several ECM elements including agrin, laminin, and perlecan (Ervasti and Campbell, (1993) *J Cell Biol.* 122: 809; Bowe, et al. (1994) *Neuron.* 12: 1173; Gee, et al. (1994) *Cell* 77: 675; Hemler, (1999) *Cell* 97: 543). This binding to matrix proteins appears to be essential for assembly of basal lamina, since mice deficient in dystroglycan fail to form these structures and die very early in development (Henry, M. D. and K. P. Campbell. 1998. *Cell.* 95: 859). β-Dystroglycan can bind the signaling adapter molecule Grb2 and associates indirectly with p125FAK (Yang, et al. (1995) *J. Biol. Chem.* 270: 11711; Cavaldesi, et al. (1999), *J. Neurochem.* 72: 01648). Although the significance of these associations remains unknown, these binding properties suggest that dystroglycan may also serve to localize signaling molecules to the cell surface.

Several lines of evidence suggest that dystroglycan may also function in neuromuscular junction formation, in particular, in postsynaptic differentiation. For purposes of clarity, the components of the neuromuscular junction are summarized here. The major structural features of the neuromuscular junction (NMJ) or nerve-muscle synapse are the pre- and post-synaptic specializations of the motor neuron and muscle, respectively, the intervening synaptic basal lamina, and the specialized Schwann cell cap (Salpeter, et al (1987) *The Vertebrate Neuromuscular Junction.* New York, Alan R. Liss.). The presynaptic apparatus is marked by ordered arrays of synaptic vesicles, a subset of which are poised to fuse with the plasma membrane at the active zones, and release acethylcholine that is recognized by acetylcholine receptors (AChRs) on the muscle, and ultimately results in electrical activation and contraction of the muscle (Heuser, et al (1981) *J. Cell Biol.* 88: 564). Immediately across the 50 nm synaptic cleft from these zones are the crests of the postjunctional folds. These crests bristle with Acetylcholine receptors (AChRs), which can reach densities of >10,000 molecules/$\mu m^2$ (Fertuck, et al (1976) *J. Cell. Biol.* 69: 144). The localized and tightly regulated secretion of acetylcholine into the narrow synaptic cleft, coupled with the high AChR density in the postsynaptic membrane, ensures rapid and reliable synaptic transmission between neuron and muscle. Perturbations of these specializations, such as the decrease in the number of functional AChRs seen in myasthenia gravis, can lead to debilitating and often fatal clinical outcomes (Oosterhuis, et al (1992) *Neurology & Neurosurgery* 5: 638).

The synaptic basal lamina (SBL) is interposed between the pre- and post-synaptic membranes and contains molecules important for the structure, function, and regulation of the neuromuscular junction (Bowe, M. A & Fallon, J. R., (1995) *Ann. Rev. Neurosci.* 18: 443; Sanes, et al. (1999) *Ann. Rev. Neurosci.* 22: 389). It consists of a distinct set of extracellular matrix molecules including specialized laminins, proteoglycans and collagens (Hall, et al (1993) *Neuron* 10: (Suppl.) 99). The SBL also contains molecules essential for the regulation of synaptic structure and function including AChE, neuregulins, and agrin. The SBL thus serves both as a specialized structure for maintaining the localized differentiation of the synapse as well as a repository for essential regulatory molecules.

The molecular composition of the postsynaptic membrane is known in considerable detail. As noted above, the most abundant membrane protein is the AChR. The cytosolic AChR associated protein rapsyn (formerly known as the 43 kD protein) is present at stoichiometric levels with the receptor and is likely to form a key link between the cytosolic domain of the AChR and the cytoskeleton (Froehner, et al (1995) *Nature* 377: 195; Gautam, et al. (1995) *Nature* 377: 232). The postsynaptic membrane is also enriched in erbB2-4, some or all of which serve as neuregulin receptors (Altiok, et al. (1995) *EMBO J.* 14: 4258; Zhu, et al. (1995) *EMBO J.* 14: 5842). AChR and other molecules are essential for nerve-muscle communication. The cytoskeletal elements can be broadly grouped into two subsets. Dystrophin and utrophin are members of the dystrophin-associated protein complex, or DAPC, and are linked to the synaptic basal lamina via the transmembrane heteromer α-/β-dystroglycan. The postsynaptic cytoskeleton is also enriched in several focal adhesion-associated molecules including α-actinin, vinculin, talin, paxillin, and filamin (Sanest et al (1999) *Ann. Rev. Neurosci.* 22: 389). The latter proteins probably communicate, directly or indirectly, with the extracellular matrix through integrins, some of which are enriched at synapses (Martin, et al. (1996) *Dev. Biol.* 174: 125). Actin is associated with both sets of cytoskeletal molecules (Rybakova et al. (1996) *J. Cell Biol.* 135: 661; Amann, et al. (1998) *J. Biol. Chem.* 273: 28419-23;

Schoenwaelder et al. (1999) *Curr. Opin. Cell. Biol.* 11: 274). The functions of these specialized sets of proteins are considered below.

α-Dystroglycan binds the synapse organizing molecule agrin (Bowe, et al. (1994) *Neuron.* 12: 1173; Campanelli, et al. (1994) *Cell.* 77: 663; Gee, et al. (1994) *Cell.* 77: 675; Sugiyama, et al. (1994) *Neuron.* 13: 103; O'Toole, et al. (1996) *Proc Natl Acad Sci USA.* 93: 7369) (reviewed in Fallon and Hall, (1994) *Trends Neurosci.* 17: 469), and β-dystroglycan binds to the AChR-associated protein rapsyn (Cartaud, et al. (1998) *J Biol Chem.* 273: 11321). Further, agrin-induced AChR clustering on the postsynaptic membrane is markedly decreased in muscle cells expressing reduced levels of dystroglycan (Montanaro, et al. (1998) *J Neurosci.* 18: 1250). The precise role of dystroglycan in this process is unknown. Currently available evidence suggests that dystroglycan is not part of the primary agrin receptor, but rather may play a structural role in the organization of postsynaptic specializations (Gesemann, et al. (1995) *Biol.* 128: 625; Glass, et al. (1996) *Cell.* 85: 513; Jacobson, et al. (1998) *J Neurosci.* 18: 6340).

Another molecule that plays an important role in neuromuscular junction formation is the tyrosine kinase receptor MuSK, which becomes phosphorylated in response to agrin. However, agrin does not bind to MuSK and it is unclear how agrin stimulates MuSK. The existence of a co-receptor had been suggested. Activation of MuSK by antibody cross-linking is sufficient to induce the clustering of AChRs on cultured myotubes (Xie et al. (1997) *Nat. Biotechnol.* 15:768 and Hopf and Hoch (1998) *J. Biol. Chem.* 273: 6467) and a constitutively active MuSK can induce postsynaptic differentiation in vivo (Jones et al. (1999) *J. Neurosci.* 19:3376). However, MuSK phosphorylation is necessary but not sufficient for agrin-induced AChR clustering.

The realm of dystroglycan function ranges far beyond muscle. As noted above, mice defective in dystroglycan die long before muscle differentiation. In a surprising development, a-dystroglycan in non-muscle cells has been shown to function as a receptor for Lassa Fever and choriomeningitis fever viruses (Cao, W., et al., 1998, *Science.* 282: 2079), and on Schwann cells as a co-receptor for *Mycobacterium leprae* (Rambukkana, et al. (1998) *Science.* 282: 2076). Dystroglycan is also abundant in brain, but its function there is not understood (Gorecki, et al. (1994) *Hum Mol Genet.* 3: 1589; Smalheiser and Kim (1995) *J Biol Chem.* 270: 15425):

α-Dystroglycan is comprised of three known domains. An amino-terminal domain folds into an autonomous globular configuration (Brancaccio, et al. (1995) *Febs Lett.* 368: 139). The middle third of the protein is serine- and threonine-rich, and is highly glycosylated (Brancaccio, et al. (1997) *Eur J Biochem.* 246: 166). Indeed, the core molecular weight of α-dystroglycan is ~68 kDa, but the native molecule migrates on SDS-PAGE as a polydisperse band whose size ranges from 120-190 kDa, depending upon the species and tissue source (Ervasti and Campbell (1993) *J Cell Biol.* 122: 809; Bowe, et al. (1994) *Neuron.* 12: 1173; Gee, et al. (1994) *Cell.* 77: 675; Matsumura, et al. (1997) *J Biol Chem.* 272: 13904). Glycosylation of α-dystroglycan, probably in this middle third, is essential for its laminin- and agrin-binding properties.

While it is clear that dystroglycan and the DAPC play crucial: roles in a variety of processes in muscle as well as in other tissues, the underlying mechanisms remain obscure.

SUMMARY OF THE INVENTION

The invention provides methods and compositions for stabilizing dystrophin-associated protein complexes (DAPCs) on the surface of a cell. Stabilizing DAPC complexes on cell membranes allows membranes to be less "leaky" and thus, provides a longer life span to cells. The invention also provides methods for activating a postsynaptic membrane, such as to render the membrane more sensitive to an incoming signal from a neural cell (e.g., at a neuromuscular junction). Activating a postsynaptic membrane may comprise stimulating aggregation of AChR on the cell membrane and/or activating MuSK, such as by phosphorylation.

In one embodiment, the method comprises contacting the target cell with a biglycan comprising an amino acid sequence which is at least about 90% identical to a portion of biglycan having SEQ ID NO: 9 and having at least one biological activity of biglycan. In a preferred method, the biglycan or portion thereof (referred to herein as "biglycan") binds to alpha-dystroglycan; alpha-sarcoglycan and/or gamma-sarcoglycan. In an even more preferred embodiment, the biglycan stimulates phosphorylation of alpha-sarcoglycan on a cell membrane. The biglycan also preferably potentiates agrin-induced AChR aggregation on the surface of the cell; stimulate the phosphorylation of MuSK on the cell; and potentiate agrin-induced phosphorylation of MuSK.

The biglycan may comprise one or more 24 amino acids repeat motifs in the Leucine Rich Repeat (LRR) of human biglycan having SEQ ID NO: 9. In another embodiment, the biglycan comprises a cysteine-rich region, e.g., the C-terminal or the N-terminal Cysteine-rich region. The biglycan may comprise glycosaminoglycan (GAG) side chains. In an even more preferred embodiment, the biglycan comprises an amino acid sequence which is at least about 90% identical to amino acids 20-368 or 38-368 of SEQ ID NO: 9, even more preferably at least 95% identical or 100% identical to amino acids 20-368 or 38-368 of SEQ ID NO: 9. In another embodiment, the biglycan is encoded by a nucleic acid which hybridizes to SEQ ID NO: 8. The biglycan can be Torpedo DAG-125, or human biglycan having SEQ ID NO: 9, or a portion of biglycan and having at least one biological activity of biglycan.

The invention also provides methods for treating, preventing and diagnosing diseases or disorders that are associated with abnormal levels or activity of biglycan; with unstable cytoplasmic membranes, due in particular, to unstable DAPCs; or abnormal synapses or neuromuscular junctions.

For example, the invention provides a method for treating or preventing a condition associated with an abnormal dystrophin-associated protein complex (DAPC) in cells of a subject, comprising administering to the subject a pharmaceutically efficient amount of biglycan or a compound which stabilizes the DAPC. Examples of diseases that can be treated or prevented include muscular dystrophies, such as Duchenne's Muscular Dystrophy, Becker's Muscular Dystrophy, Congenital Muscular Dystrophy, Limb-girdle Muscular Dystrophy, and myotonic dystrophy; and cardiomyopathies.

In another example, the invention provides a method for treating or preventing a condition characterized by an abnormal neuromuscular junction or synapse in a subject, comprising administering to the subject a pharmaceutically efficient amount of a biglycan or homolog which binds to, and/or induces phosphorylation of MuSK and/or which induces aggregation of acetylcholine receptors (AChRs). The condition can be a neuromuscular or neurological disease.

In yet another example, the invention provides a diagnostic method for determining whether a subject has or is at risk of developing a condition associated with an abnormal DAPC or abnormal synapse or neuromuscular junction, or other disease associated with an abnormal biglycan level or activity, comprising determining the level or activity of biglycan in a tissue of the subject, wherein the presence of an abnormal level and/or activity of biglycan in the tissue of a subject indicates that the subject has or is at risk of developing a condition associated with an abnormal DAPC or abnormal synapse or neuromuscular junction or other disease associated with an abnormal biglycan level or activity.

Also within the scope of the invention are screening methods for identifying agents which bind to biglycan, such as a human biglycan or Torpedo DAG-125, or agents which inhibit its binding to another molecule, such as a member of a DAPC or MuSK. Agents identified in these assays can be used, e.g., in therapeutic methods. Screening methods for identifying agents which modulate phosphorylation induced by biglycan are also within the scope of the invention.

Other aspects of the invention are described below or will be apparent to those skilled in the art in light of the present disclosure.

DETAILED DESCRIPTION OF THE INVENTION

General

Figure 1:
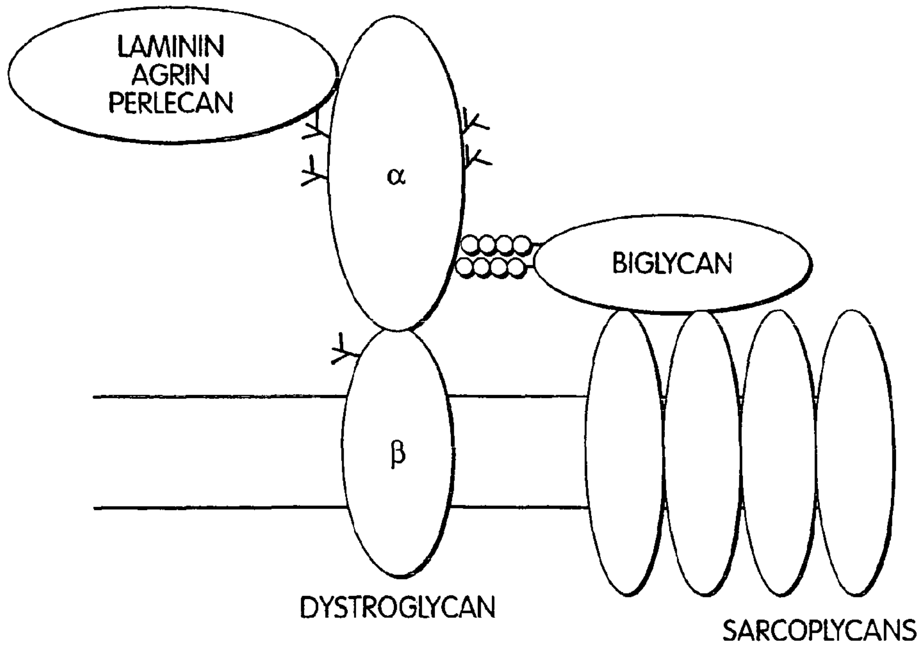
FIG. 1 is a diagram of the interaction of DAG-125 or biglycan with a DAPC.

The invention is based at least in part on the observation that biglycan interacts with, and sometimes modifies, components of the dystrophin-associated protein complex (DAPC), as well as activates components playing an important role in neuromuscular junction formation. In particular, biglycan was shown to interact with α-dystroglycan, an extracellular component of the DAPC, as well as with α-sarcoglycan and γ-sarcoglycan, which are components of the sarcoglycan complex of the DAPC. Biglycan was also shown to phosphorylate α-sarcoglycan, showing that biglycan does not solely interact with components of the DAPC, but also modifies some of the components. The proteoglycan of the invention has been found to be overexpressed in an animal model of muscular dystrophy that is characterized by the absence of dystrophin. The integrity of the DAPC and its association with the extracellular matrix (ECM) are essential for muscle cell viability. Accordingly, biglycan is believed to stabilize the DAPC complex at the surface of cells, in particular, muscle cells, and can be part of a compensatory mechanism that allows survival of dystrophin negative fibers.

It has also been shown herein that biglycan is involved in neuromuscular junction formation, e.g., induced by agrin. Agrin, which is an extracellular matrix protein present in the synaptic basal lamina, is secreted by the nerve terminal and triggers neuromuscular junction formation by activating the receptor tyrosine kinase MuSK, thereby inducing phosphorylation and clustering of AChR. It had not previously been known how agrin activates the receptor MuSK, since agrin does not bind directly to this receptor. The inventors have uncovered that activation of the receptor MuSK by agrin is actually potentiated by biglycan. This discovery is based at least in part on their finding that biglycan binds directly to the MuSK receptor; biglycan directly induces the tyrosine phosphorylation of MuSK; biglycan potentiates agrin-induced phosphorylation of MuSK; and biglycan potentiates agrin-induced clustering of AChRs. In addition, the inventors have shown that myotubes from biglycan deficient mice show a defective response to agrin, in particular the cells are defective in agrin-induced AChR clustering, which was further shown to be corrected by the addition of biglycan to the culture media of the myotubes. Thus, it was clearly shown that the absence of biglycan in cells results in a deficiency in agrin-induced AChR clustering, which can be corrected by the addition of biglycan to the cells. The role of biglycan in mediating neuromuscular junction formation, in particular, postsynaptic differentiation, is further supported by the fact biglycan binds to α-dystroglycan (shown herein), and that α- and β-dystroglycans interact with components of the postsynaptic membrane. For example, agrin binds to α-dystroglycan (see FIG. 1 and "Background of the Invention") and β-dystroglycan binds to the AChR-associated protein rapsyn. In addition, agrin-induced AChR clustering is markedly decreased in muscle cells expressing reduced levels of dystroglycan, further demonstrating the role of dystroglycan in postsynaptic membranes. Thus, it was demonstrated herein that biglycan plays an important role in the formation of neuromuscular junctions both by interacting with the agrin receptor MuSK and by interacting with α-dystroglycan. It is likely that biglycan plays a functional and a structural role in the organization of the postsynaptic specializations.

Furthermore, since DAPCs are also found in brain, agrin has been found in senile plaques in brains of subjects with Alzheimer's disease, and peripheral and central neural deficiencies are present in some patients lacking dystrophin, biglycan is also believed to be involved in formation of synapses.

Thus, the results described herein indicate that biglycan plays an important role in maintaining the integrity of muscle cell plasma membrane, at least in part by interacting with α-dystroglycan and the sarcoglycans in the DAPC; in neuromuscular junction formation, at least in part by mediating agrin-induced AChR clustering and MuSK activation; and also probably in synapse formation. Based at least on these findings, the invention provides compositions and methods for diagnosing, treating and/or preventing diseases or conditions associated with a dysfunctional DAPC, an unstable cellular structure, a defect in neuromuscular junctions or synapses. Such diseases include, in particular, muscular dystrophies, such as Duchenne, Limb-girdle, other myopathies, neuromuscular disorders, and neurological disorders.

Furthermore, in view of the wide tissue distribution of DAPCs and dystroglycans, the proteoglycan of the invention is likely to play a role in regulating signaling through the cytoplasmic membrane and/or maintaining the integrity of cytoplasmic membranes of cells other than muscle cells. For example, dystroglycan or other DAPC components are abundant in brain, kidney, and heart (see "Background of the Invention"). Thus, the invention provides, more generally, compositions, diagnostic and, therapeutic methods for diseases or disorders associated with an abnormality of a membrane protein complex with which the protein of the invention interacts, e.g., the DAPC, or MuSK receptor.

Based at least on the fact that dystroglycan is known to be a receptor used by microorganisms for entering cells, e.g., Lassa Fever and choriomeningitis fever viruses, the compositions of the invention can be used for treating and/or preventing infections by such microorganisms. Without wanting to be limited to a specific mechanism of action, biglycan therapeutics may hinder or inhibit binding of the microorganism to dystroglycan.

Both human biglycan (described, e.g., in Fischer et al. as "bone small proteoglycan" J. Biol. Chem. 264: 4571 (1996); GenBank Accession No. J04599; SEQ ID NO: 9) and DAG-125 isolated from Torpedo electric organ have been shown to interact with DAPC components. Based on sequence homologies between the two proteins and similar biological activities (further described herein), it is believed that the human biglycan (SEQ ID NO: 9) may be the human ortholog of the Torpedo DAG-125. Alternatively, the human ortholog of the Torpedo DAG-125 may be a protein that is highly related to human biglycan. For purposes of clarity, the term "biglycan" as used herein is intended to include the human biglycan (SEQ ID NO: 9) and Torpedo DAG-125, as well as homologs of these proteoglycans.

Definitions

For convenience, the meaning of certain terms and phrases employed in the specification, examples, and appended claims are provided below.

"GAGs" refers to glycosaminoglycans, which is used interchangeably herein with "mucopolysaccharides," are long, unbranched polysaccharide chains composed of repeating disaccharide units. One of the two sugars is always an amino sugar (N-acetylglucosamine or N-acetylgalactosamine). Glycosaminoglycans are covalently linked to a serine residue of a core protein, to form a proteoglycan molecule.

The term "glycan" is used interchangeably herein with the term "polysaccharide" and "oligosaccharide."

The term "glycoprotein" refers to a protein which contains one or more carbohydrate groups covalently attached to the polypeptide chain. Typically, a glycoprotein contains from 1% to 60% carbohydrate by weight in the form of numerous, relatively short, branched oligosaccharide chains of variable composition. In contrast to glycoproteins, proteoglycans are much larger (up to millions of daltons), and they contain 90% to 95% carbohydrate by weight in the form of may long, unbranched glycosaminoglycan chains.

The term "proteoglycan of the invention" refers to a proteoglycan molecule having one or more of the characteristics and biological activities of biglycan. Accordingly, a preferred proteoglycan of the invention includes a proteoglycan having one or more of the following characteristics: a molecular weight between 100 and 150 kDa, or an apparent mobility of 125 kDa, as determined on an SDS acrylamide gel; one or more glycosaminoglycan side chain; a molecular weight of the core between 35 and 40 kDa, preferably around 37 kDa; an amino acid sequence selected from SEQ ID NO: 1-6 and 9 or variant thereof; one of more biological activities of biglycan, as listed infra, under the corresponding definition. In one embodiment, the proteoglycan of the invention is a SLRP, e.g., human biglycan. A preferred proteoglycan of the invention is Torpedo DAG-125 or a mammalian, preferably human, ortholog thereof. Another preferred proteoglycan of the invention is biglycan, e.g., human biglycan having SEQ ID NO: 9. The term "proteoglycan of the invention" further includes portions of the wild type proteoglycan, provided that these portions have at least one biological activity of a biglycan protein. Accordingly, the term "proteoglycan of the invention" includes molecules that consist only of the core (i.e., protein part of the molecule), or of the GAG side chains, portions thereof and/or combinations thereof.

The term "biglycan" refers to proteoglycans having at least one biological activity of human biglycan or Torpedo DAG-125. Preferred biglycans include Torpedo DAG-125 (comprising SEQ ID NO: 1-3), human biglycan (SEQ ID NO: 9), as well as homologs thereof. Preferred homologs are proteoglycans or proteins or peptides having at least about 70% identity, at least about 75% identity, at least about 80% identity, at least about 85% identity, at least about 90% identity, at least about 95% identity, and even more preferably, at least about 98 or 99% identity. Even more preferred homologs are those which have a certain percentage of homology (or identity) with human biglycan or Torpedo DAG-125 and have at least one biological activity of these proteoglycans. The term biglycan is not limited to the full length biglycan, but includes also portions having at least one activity of biglycan.

The term "human biglycan" refers to the proteoglycan described in Fischer et al. J. Biol. Chem. 264: 4571 (1989), having GenBank Accession No. J04599, and the amino acid sequence set forth in SEQ ID NO: 9. A cDNA sequence encoding the human biglycan protein is set forth in SEQ ID NO: 7, and the open reading frame thereof as SEQ ID NO: 8.

The term "biglycan core" refers to a biglycan that does not include GAG chains.

The term "biglycan proteoglycan" or "biglycan PG" refers to a biglycan having at least one GAG chain.

The term "biglycan nucleic acid" refers to a nucleic acid encoding a biglycan proteoglycan, e.g., a nucleic acid encoding a protein having SEQ ID NO: 9.

A "biological activity of biglycan" is intended to refer to one or more of: the ability to maintain the integrity of a plasma membrane; the ability to stabilize DAPCs on plasma membranes; the ability to bind to one or more components of DAPCs; e.g., binding to a-dystroglycan, binding to a sarcoglycan component, such as $\alpha$-sarcoglycan or $\gamma$-sarcoglycan; binding to MuSK; stimulating the formation of neuromuscular junctions, such as by stimulating postsynaptic differentiation; potentiation of AChR aggregation, e.g., agrin-induced AChR aggregation; phosphorylation of DAPC components, e.g., sarcoglycans; stimulation MuSK phosphorylation or potentiating agrin-induced MuSK phosphorylation.

A "biglycan therapeutic" is a compound which can be used for treating or preventing a disease that is associated with an abnormal cytoplasmic membrane, e.g., an unstable membrane; an abnormal DAPC; abnormal neuromuscular junction; abnormal synapse; abnormal AChR aggregation; or abnormal MuSK activation. A biglycan therapeutic can be an agonist or an antagonist of one or more of the biological activities of biglycan. A therapeutic can be any type of compound, including a protein or derivative thereof, e.g., a proteoglycan, a nucleic acid, a glycan, or a small organic or synthetic molecule.

The term "abnormal" is used interchangeably herein with "aberrant" and refers to a molecule, or activity with differs from the wild type or normal molecule or activity.

The term "DAPC" refers to "dystrophin-associated protein complex", a membrane complex, set forth in FIG. 1, which comprises dystrophin, alpha- and beta-dystroglycans, and the sarcoglycan transmembrane complex.

"Sarcoglycans" exit in different forms including alpha-, beta-, gamma-, delta-, and epsilon-sarcoglycans. Certain sarcoglycans are specific for certain tissues, e.g., alpha and delta-sarcoglycans are skeletal muscle specific.

"Dystrophin-associated proteins" includes proteins or glycoproteins, such as alpha-dystroglycan, dystrobrevin, sarcospan and the syntrophins.

The term "AChR" refers to acetylcholine receptor.

The term "SLRP" refers to small leucine rich repeat proteoglycan.

The term "MASC" refers to muscle cell-associated specificity component.

The term "RATL" refers to rapsyn-associated transmembrane linker.

The term "HSPG" refers to heparan sulfate proteoglycans.

The term "MuSK" used interchangeably herein with "muscle specific kinase," refers to a protein tyrosine kinase that is expressed in normal and denervated muscle, as well as other tissues including heart, spleen, ovary or retina (See Valenzuela, D., et al., 1995, *Neuron* 15: 573-584). The tyrosine kinase has alternatively been referred to as "Dmk" for "denervated muscle kinase." Thus, the terms MuSK and Dmk may be used interchangeably. The protein appears to be related to the Trk family of tyrosine kinases, and is further described in U.S. Pat. No. 5,814,478.

The term "MuSK activating molecule" as used herein refers to a molecule which is capable of inducing phosphorylation of the MuSK receptor in the context of a differentiated muscle cell. One such activating molecule is agrin as described in the Examples set forth herein.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of SEQ ID NO: 7 or 8, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length human biglycan polynucleotide sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

"Small molecule" as used herein, is meant to refer to a composition, which has a molecular weight of less than about 5 kD and most preferably less than about 4 kD. Small molecules can be nucleic acids, peptides, polypeptides, peptidomimetics, carbohydrates, lipids or other organic (carbon containing) or inorganic molecules. Many pharmaceutical companies have extensive libraries of chemical and/or biological mixtures, often fungal, bacterial, or algal extracts, which can be screened with any of the assays of the invention to identify compounds that modulate the bioactivity of a proteoglycan of the invention.

A "myoblast" is a cell that, by fusion with other myoblasts, gives rise to myotubes that eventually develop into skeletal muscle fibres. The term is sometimes used for all the cells recognisable as immediate precursors of skeletal muscle fibres. Alternatively, the term is reserved for those post-mitotic cells capable of fusion, others being referred to as presumptive myoblasts.

"Myofibril" is a long cylindrical organelle of striated muscle, composed of regular arrays of thick and thin filaments, and constituting the contractile apparatus.

A "myotube" is an elongated multinucleate cells (three or more nuclei) that contain some peripherally located myofibrils. They are formed in vivo or in vitro by the fusion of myoblasts and eventually develop into mature muscle fibres that have peripherally located nuclei and most of their cytoplasm filled with myofibrils. In fact, there is no very clear distinction between myotubes and muscle fibers proper.

"Utrophin" (dystrophin associated protein) is an autosomal homologue of dystrophin (of size 395 kD) localised near the neuromuscular junction in adult muscle, though in the absence of dystrophin (i.e. in Duchenne muscular dystrophy) utrophin is also located on the cytoplasmic face of the sarcolemma.

As used herein, the term "transfection" means the introduction of a nucleic acid, e.g., an expression vector, into a recipient cell by nucleic acid-mediated gene transfer. The term "transduction" is generally used herein when the transfection with a nucleic acid is by viral delivery of the nucleic acid. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the recombinant protein is disrupted.

As used herein, the term "transgene" refers to a nucleic acid sequence which has been introduced into a cell. Daughter cells deriving from a cell in which a transgene has been introduced are also said to contain the transgene (unless it has been deleted). A transgene can encode, e.g., a polypeptide, partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene). Alternatively, a transgene can also be present in an episome. A transgene can include one or more transcriptional regulatory sequences and any other nucleic acid, (e.g. intron), that may be necessary for optimal expression of a selected coding sequence.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

"Derived from" as that phrase is used herein indicates a peptide or nucleotide sequence selected from within a given sequence. A peptide or nucleotide sequence derived from a named sequence may contain a small number of modifications relative to the parent sequence, in most cases representing deletion, replacement or insertion of less than about 15%, preferably less than about 10%, and in many cases less than about 5%, of amino acid residues or base pairs present in the parent sequence. In the case of DNAs, one DNA molecule is also considered to be derived from another if the two are capable of selectively hybridizing to one another.

The terms "chimeric", "fusion" and "composite" are used to denote a protein, peptide domain or nucleotide sequence or molecule containing at least two component portions which are mutually heterologous in the sense that they are not, otherwise, found directly (covalently) linked in nature. More specifically, the component portions are not found in the same continuous polypeptide or gene in nature, at least not in the same order or orientation or with the same spacing present in the chimeric protein or composite domain. Such materials contain components derived from at least two different proteins or genes or from at least two non-adjacent portions of the same protein or gene. Composite proteins, and DNA sequences which encode them, are recombinant in the sense that they contain at least two constituent portions which are not otherwise found directly linked (covalently) together in nature.

The term "modulate" refers to inhibiting or stimulating.

The term "activating a postsynaptic membrane" refers to the stimulation of the transfer of a signal at neuromuscular junction, generally, from a nerve cell to a muscle cell. Activation usually includes the stimulation of aggregation of AChR on the cell membrane at the neuromuscular junction; and/or the phosphorylation of MuSK. Activation results in induction of postsynaptic differentiation.

The term "treating" with regard to a subject, refers to improving at least one symptom of the subject's disease or disorder. Treating can be curing the disease or condition or improving it, but reducing at least certain symptoms of it.

Compounds of the Invention

The invention provides compounds for use in maintaining the integrity of plasma cell membranes, in particular, compounds which stabilize dystrophin associated protein complexes (DAPC) in these membranes, thereby preventing the disintegration of the membranes. The invention also provides compounds which stimulate neuromuscular junction formation, such as by stimulating postsynaptic membrane differentiation, and more generally compounds which stimulate synapse formation.

In a particular embodiment, the compound binds to one or more components of the DAPC. The compound preferably binds to α-dystroglycan and/or to a sarcoglycan component, such as α-sarcoglycan. In an even more preferred embodiment, the compound of the invention binds both to α-dystroglycan and to a component of the sarcoglycan complex, e.g., selected from the group consisting of α-sarcoglycan, γ-sarcoglycan and δ-sarcoglycan. The component of the sarcoglycan to which the compound of the invention binds is preferably α-sarcoglycan. Generally, the compound of the invention contacts one or more components of the DAPC, e.g., to thereby stabilize the complex and reduce destabilization of the plasma membrane resulting from an abnormal DAPC complex, such as those seen in muscular dystrophies.

Yet in an even more preferred embodiment, the compound of the invention binds to a region of α-dystroglycan which is different from the region to which agrin, laminin and perlecan bind (see FIG. 1). Binding of the compounds of the invention do not require the presence of glycosyl side chains on α-dystroglycan. More preferably, the compounds of the invention bind to the C-terminal part of alpha-dystrogylcan, preferably to about amino acids 345 to 891, more preferably to about amino acids 1-750, about amino acids 30-654, about amino acids 345-653, or about amino acids 494-653 of human alpha-dystroglycan. Thus, a preferred compound of the invention binds to a region consisting essentially of the C-terminal 150 amino acids of a-dystroglycan, i.e., amino acids 494-653.

Other compounds of the invention bind to the receptor tyrosine kinase MuSK. Such compounds can bind to MuSK and/or α-dystroglycan and/or a component of the sarcoglycan complex, e.g., α-sarcoglycan.

The compounds preferably bind specifically to one or more of the above-cited molecules, i.e., they do not significantly or at a detectable level bind to other molecules to produce an undesirable effect in the cell. The compounds preferably bind with a dissociation constant of $10^{-6}$ or less, and even more preferably with a dissociation constant of $10^{-7}$, $10^{-8}$, $10^{-9}$, $10^{-10}$, $10^{-11}$, $10^{-12}$, or $10^{-13}$ M or less. The dissociation constant can be determined according to methods well known in the art.

Binding assays for determining the level of binding of a compound to a component of the DAPC or to MuSK or for identifying members of library of compounds which bind to these molecules are known in the art and are also further described herein. Methods for preparing DAPC components or MuSK for use in such assays are also known. Such components can be isolated from tissue or they can be prepared recombinantly or synthetically. Their nucleotide and amino acid sequences are publicly available, e.g., from GenBank, or from publications.

Other preferred compounds of the invention have one or more biological activities of biglycan, in addition to, or instead of, being able to bind one or more components of the DAPC and/or MuSK. For example, a compound of the invention can stimulate neuromuscular junction formation, in particular, postsynaptic membrane differentiation, including inducing aggregation of AChRs and/or stimulating or stimulating agrin-induced tyrosine phosphorylation of MuSK.

The compound of the invention can be a protein or derivative thereof, in particular a proteoglycan, a nucleic acid, such as a nucleic acid encoding a proteoglycan of the invention, a glycan, a peptidomimetic or derivative thereof, or a small organic molecule. Generally, the compound can be any type of molecule provided that the compound has the required characteristics, e.g., binding to α-sarcoglycan and/or other DAPC components.

In a preferred embodiment, the compound of the invention is a proteoglycan having a molecular weight from about 100 kDa to about 150 kDa, preferably from about 110 kDa to about 140 kDa, and most preferably from about 120 to about 130 kDa, as determined, e.g., by migration on an SDS acrylamide gel. The core of the proteoglycan of the invention has a molecular weight from about 25 to about 45 kDa, preferably from about 30 to about 40 kDa and most preferably around 37 kDa. Fragments or portions of these proteoglycans are also within the scope of the invention.

The proteoglycan preferably contains one or more glycosaminoglycan side chains, such as a mucopolysaccharide side chain, e.g., heparan, chondroitin, or dermatan. Preferred side chains consist of chondroitin sulfate, e.g., 4-sulfate (chondroitin sulfate type A) and 6-sulfate (chondroitin sulfate type C). Any side chain can be used in the invention, provided that the proteoglycan has at least one bioactivity of biglycan.

In an even more preferred embodiment, the proteoglycan of the invention comprises one or more of the following amino acid sequence in its core: IQAIEFEDL (SEQ ID NO: 1); LGLGFNEIR (SEQ ID NO: 2); and TSYHGISLFNNPVNYWDVL (SEQ ID NO: 3), or amino acid sequences related thereto, such as amino acid sequences from the mammalian ortholog of the Torpedo protein from which these amino acid sequences were obtained. The proteoglycan preferably contains all three of these sequences or sequences related thereto. For example, the proteoglycan of the invention can comprise one or more of the following amino acid sequences, which are part of human biglycan: IQAIELEDL (SEQ ID NO: 4); LGLGHNQIR (SEQ ID NO: 5); and AYYNGISLFNNPVPYWEVQ (SEQ ID NO: 6).

Although composition including, and methods using, Torpedo DAG-125 are within the scope of the invention, preferred compositions and methods are those relating to mammalian, including vertebrate, homologs of Torpedo DAG-125, referred to herein as orthologs of Torpedo DAG-125. Preferred orthologs of Torpedo DAG-125 are human, rodent, murine, canine, feline, ovine, and bovine orthologs. As shown herein, it is highly likely that the mammalian DAG-125 is biglycan, however, it may also be a molecule that is related to biglycan, and, e.g., also to decorin (see below), but is actually a not previously described protein. Thus, the invention also provides compositions comprising the mammalian ortholog of Torpedo DAG-125, such as the human ortholog of Torpedo DAG-125.

A mammalian ortholog of Torpedo DAG-125 can be isolated by screening libraries with probes containing nucleotide sequences encoding one or more of SEQ ID NOs 1-3. Numerous other methods are available for cloning the mammalian ortholog of Torpedo DAG-125. For example, antibodies to Torpedo DAG-125 can be produced and used to screen mammalian expression libraries. The identification of the cloned proteins as mammalian orthologs of Torpedo DAG-125 can be established by performing the same biological assays as those described in the Examples employing Torpedo DAG-125.

Thus, the proteoglycan of the invention can also be a member of the family of small leucine-rich proteoglycans (SLRP), also referred to as "nonaggregating or small dermatan-sulfate proteoglycans because of their inability to interact with hyaluronan, or because of their type of glycosaminoglycans, respectively. SLRPs are organized into three classes based on their protein and genomic organization. All SLRPs are characterized by a central domain containing leucine rich repeats (LRR) flanked at either side by small cysteine clusters. The SLRPs are described, e.g., in Iozzo et al. (1998) *Ann. Rev. Biochem.* 67:609, specifically incorporated herein by reference.

Figure 5A:
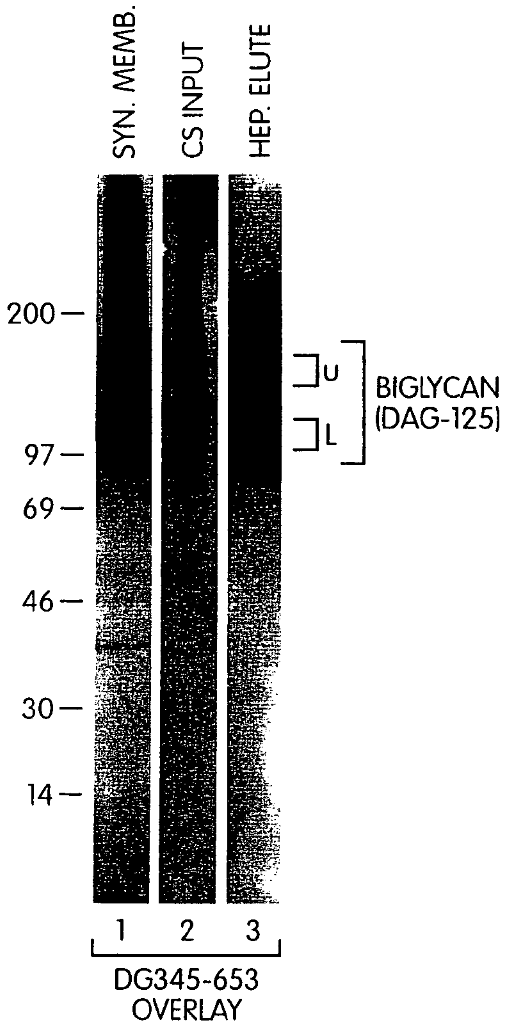
FIG. 5 A shows a blot overlay assay in which a filter with synaptic membranes, input or elute from a column was incubated with a portion of alpha-dystroglycan.
FIG. 5B shows the sequence alignment between the Torpedo DAG-125 sequences (SEQ ID NOs: 1-3) and human biglycan (SEQ ID NOs: 4-6).
FIG. 5C is a diagram of the structure of biglycan: the prepro-region, which is absent in the mature biglycan, corresponds to amino acids 1-37 of SEQ ID NO: 9; the N-terminal cysteine-rich region corresponds to amino acids 38-80 of SEQ ID NO: 9; the LLR region corresponds to about amino acids 81-314 of SEQ ID NO: 9; and the C-terminal cysteine-rich region corresponds to amino acids 315-368 of SEQ ID NO: 9. Circles represent chondroitin sulfate side chains. "S—S" denotes intrachain disulfide binding.
Figure 5B:
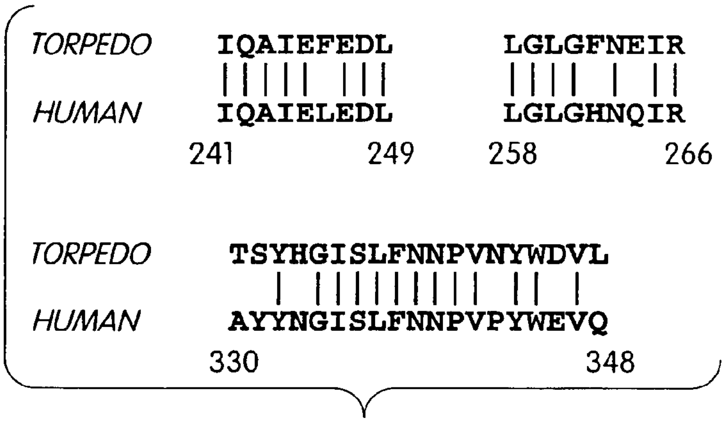
Figure 5C:
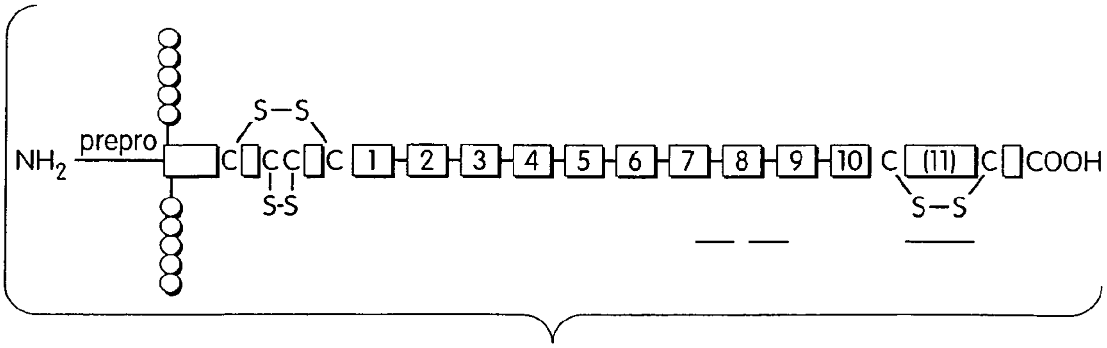

SLRP protein cores range from ~35-45 kD with one or two GAG chains attached at the extreme N-terminus. The general structure of the SLRP protein core consists of a tandem array of 6-10 leucine-rich repeats (LRR) flanked by domains with conserved, disulfide-bonded cysteines (FIG. 5C). Depending upon the extent of glycosylation and number of GAG chains, the native molecular weight ranges from ~100-250 kD. On the basis of their sequence homology, lozzo, supra, has proposed that SLRPs be grouped into three classes consisting of: 1) biglycan and decorin; 2) fibromodulin, lumican, keratocan, PREPLP, and osteoadherin; and 3) epiphycan and osteoglycin. The most compelling feature of the SLRP protein core is the LRRs. Such repeats (24aa each in the SLRPs) mediate protein-protein interactions in a wide variety of intracellular, transmembrane, and extracellular contexts (Kobe & Deisenhofer, (1994) *Trends Biochem. Sci.* 19: 415-21). The neurotrophin binding site on trkB, for example, is an LRR (Windisch et al., (1995) *Biochemistry* 34: 11256-63). The repeats are thought to have a general structure of an $\alpha$-helix followed by beta-sheet in an anti-parallel array, although sequence analysis has suggested that this order might be reversed in the SLRPs (Hocking et al., (1998) *Matrix Biol.* 17: 1-19). It is likely that the conserved residues of each repeat dictate their secondary structure, while the intervening amino acids determine specificity of ligand binding.

Preferred SLRPs for use in the invention include Class I SLRPs, such as biglycan and decorin. The partial amino acid sequences of DAG-125, the Torpedo proteoglycan which was shown to bind to alpha-dystroglycan (see Examples) shows strong homology to human biglycan (see FIG. 5B): a 78% identity was found in a total of 37 amino acid long sequence. Biglycan from rodent, pig and human are >95% identical. Decorin and biglycan from human are only 55% identical. Such homology is consistent with decorin and biglycan having both shared and unique functions. Thus, although Torpedo DAG-125 has amino acid sequence that more closely resemble that of human biglycan, based on the similarity of structure and function between biglycan and decorin, the latter proteoglycan and derivatives thereof may also be used to practice the invention.

Nucleotide and amino acid sequences of biglycan and decorin genes and proteins from various species are publically available, such as in GenBank. For example, human biglycan can be found under GenBank Accession No. J04599 (human hPGI encoding bone small proteoglycan I (biglycan), described in Fisher et al. (1989) J. Biol. Chem. 264: 4571; SEQ ID Nos: 7-9) and M65154; cow biglycan can be found under GenBank Accession No. L07953; rat biglycan can be found under GenBank Accession No. U17834, mouse biglycan can be found under GenBank Accession No. L20276 and X53928; ovis biglycan can be found under GenBank Accession No. AF034842; human decorin can be found at GenBank Accession No. M14219; rabbit decorin can be found at GenBank Accession No. 147020; chick decorin can be found at GenBank Accession No. P28675; Equus decorin can be found at GenBank Accession No. AF038; bovine decorin can be found at GenBank Accession No. P21793; ovis decorin can be found at GenBank Accession No. AF125041; and rat decorin can be found at GenBank Accession No. Q01129. Sequences of biglycan and decorin and other SLRPs can be found in GenBank.

Decorin and biglycan have one and two glycosaminoglycan (GAG) chains, respectively. Their composition is tissue specific and can be regulated at a number of levels (Hocking et al., (1998) *Matrix Biol* 17: 1-19). For example, the biglycan GAG from skin and cartilage is predominantly dermatan sulfate, while biglycan synthesized in bone is a chondroitin sulfate proteoglycan. Heparan sulfate side chains have not been reported. Both the protein core and the cell type contribute to the distinct glycosylation of these SLRPs.

Other proteoglycans or cores thereof of the invention include fusion proteins. For example, biglycan or a portion thereof can be fused to an immunoglobulin portion. Alternatively, the fusion protein is a combination between two or more portions of proteoglycans of the invention, e.g., a portion of a biglycan molecule fused to a portion of a decorin molecule (see examples).

Portions and fragments of the proteoglycans of the invention are also within the scope of the invention. A portion is typically at least five, 10, 15, or 20 amino acids long. Preferred portions are those which are sufficient for exerting a biological activity, such as interacting with a DAPC component. Portions can comprise or consist of one or more specific domain of a protein. Domains of biglycan and decorin include two cysteine-rich regions (included in the N- and C-terminal 40-50 amino acids of mature biglycan) and leucine-rich repeats (LRRs). The "LRR region" refers to the region of biglycan containing the repeats, and consists essentially of amino acids 81-314. Each individual repeat is referred to herein as an "LRR." LRRs are believed to mediate protein: protein interactions and may thus be sufficient for stabilizing DAPCs and postsynaptic membranes. Based at least on the observation that both decorin and biglycan bind to MuSK and that the LLR region in both of these proteins is very similar, it is believed that the LRRs are involved in mediating the interaction of biglycan (and decorin) with MuSK and may be involved in mediating MuSK phosphorylation.

Another preferred biglycan of the invention consists of a portion of biglycan that is capable of binding to a sarcoglycan. It has been shown that the alpha-sarcoglycan binding domain of human biglycan is located in the N-terminal domain of the mature biglycan protein, i.e., amino acids 38-80, and more specifically, amino acids 38-58 of SEQ ID NO: 9. The GAG chains are not necessary for binding to alpha-sarcoglycan. It has also been shown that the C-terminal cysteine-rich domain mediates interaction with gamma-sarcoglycan. Accordingly, preferred biglycans of the invention include portions of biglycan consisting of the N-terminal or the C-terminal cysteine-rich domain, i.e., amino acids 38-80 and 315-368 of SEQ ID NO: 9. Combinations of certain domains of biglycan are also within the scope of the invention.

Thus, preferred fragments consist of at least about 30 amino acids, at least about 40 amino acids, 50, 60, 70, 80, 90, 100, 150, or 200 amino acids. Short portions of the proteoglycans of the invention are termed "mini-proteoglycan of the invention." For example, a biglycan core fragment of about 20, 30 or 40 amino acids is referred to as a "mini-biglycan."

Human biglycan consists of 368 amino acids (SEQ ID NO: 9), of which amino acids 1-19 constitute a signal peptide (GenBank Accession No. NP_001702 and Fisher et al., supra). Thus biglycan without a signal peptide consists of amino acids 20-368 of SEQ ID NO: 9. The mature biglycan protein consists of amino acids 38-368 of SEQ ID NO: 9, since amino acids 1-37, being a pre-propeptide, are cleaved during processing. Amino acids 38-80 correspond to the N-terminal cysteine-rich region. About amino acids 81-314 corresponds to the leucine rich repeat region, containing 10 repeats of about 24 or 23 amino acids. The open reading frame in the cDNA encoding human biglycan corresponds to nucleotides 121-1227 of SEQ ID NO: 7 and is represented as SEQ ID NO: 8. The nucleotide sequence encoding a mature form of biglycan consists in nucleotides 232-1227 of SEQ ID NO: 7.

In addition to agonists, the invention also provides antagonists of biglycan. An antagonist can be, e.g., a portion of the wild type proteoglycan of the invention which inhibits the action of the wild type proteoglycan, such as by competitively inhibiting the binding of the wild type proteoglycan to a target protein such as a component of a DAPC. Thus, an antagonist can be a dominant negative mutant.

The proteoglycan can be a mature form of the proteoglycan core, i.e., deprived of the signal peptide, or the full length proteoglycan with the signal peptide.

Preferred proteoglycans of the invention are encoded by nucleotide sequences which are at least about 70%, preferably at least about 80%, even more preferably at least about 85%, at least about 90%, at least about 95%, at least about 98%, and even more preferably at least about 99% identical to the nucleotide sequence of an SLRP, e.g., biglycan, or ortholog thereof, or portion thereof.

Preferred nucleic acids of the invention include those encoding a polypeptide comprising an amino acid sequence which is at least about 70%, preferably at least about 80%, even more preferably at least about 85%, at least about 90%, at least about 95%, at least about 98%, and even more preferably at least about 99% identical to the nucleotide sequence of an SLRP, e.g., biglycan (e.g., SEQ ID NO: 7 or 8 encoding human biglycan) or DAG-125 or ortholog thereof, portion thereof. In one embodiment, the nucleic acid encodes a polypeptide containing one or more of SEQ ID NOs: 1-3 or SEQ ID NOs: 4-6 or 9.

Another aspect of the invention provides a nucleic acid which hybridizes under stringent conditions to a nucleic acid encoding biglycan, e.g., having one or more of SEQ ID NOS: 1 to 6 or 9, or complement thereof. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature of salt concentration may be held constant while the other variable is changed. In a preferred embodiment, a nucleic acid of the present invention will bind to one of SEQ ID NOS 1 to 6 or complement thereof or nucleic acid encoding a SLRP under moderately stringent conditions, for example at about 2.0×SSC and about 40° C. In a particularly preferred embodiment, a nucleic acid of the present invention will hybridize to a nucleotide sequence encoding one of SEQ ID NOS: 1 to 6 or 9, such as a nucleic acid having SEQ ID NO: 7 or 8, or a complement thereof under high stringency conditions.

Methods for preparing compounds of the invention are well known in the art. For a compound of the invention which is a protein or a derivative thereof, the compound can be isolated from a tissue or the compound can be recombinantly or synthetically produced. Isolation of the protein from a tissue is described in the Examples. The proteins or proteoglycans of the invention isolated from tissue are preferably at least about 70%, preferably at least about 80%, at least about 85%, at least about 90%, at least about 95%, at least about 98% and most preferably, at least about 99% pure. Accordingly, preferred compounds contain less than about 1%, and even more preferably less than about 0.1% of material from which the compound was extracted.

The protein of the invention can also be produced recombinantly, according to methods well known in the art. Typically, a gene encoding the protein is inserted into a plasmid or vector, and the resulting construct is then transfected into appropriate cells, in which the protein is then expressed, and from which the protein is ultimately purified.

Accordingly, the present invention further pertains to methods of producing the subject proteins. For example, a host cell transfected with an expression vector encoding a protein of interest can be cultured under appropriate conditions to allow expression of the protein to occur. The protein may be secreted, by inclusion of a secretion signal sequence, and isolated from a mixture of cells and medium containing the protein. Alternatively, the protein may be retained cytoplasmically and the cells harvested, lysed and the protein isolated. A cell culture includes host cells, media and other byproducts. Suitable media for cell culture are well known in the art. The proteins can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the protein.

Thus, a coding sequence for a protein of the present invention can be used to produce a recombinant form of the protein via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures.

Expression vehicles for production of a recombinant protein include plasmids and other vectors. For instance; suitable vectors for the expression of the instant fusion proteins include plasmids of the types: pBR322-derived plasmids, pEMBL-derived plasmids, pEX-derived plasmids, pBTac-derived plasmids and pUC-derived plasmids for expression in prokaryotic cells, such as *E. coli.*

A number of vectors exist for the expression of recombinant proteins in yeast. For instance, YEP24, YIPS, YEP51, YEP52, pYES2, and YRP17 are cloning and expression vehicles useful in the introduction of genetic constructs into *S. cerevisiae* (see, for example, Broach et al., (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used.

The protein can be produced either in eukaryotic cells, e.g., mammalian cells, yeast cells, insect cell (baculovirus system) or in prokaryotic cells. However, if the protein is a proteoglycan, it is preferably to express it in a cell of the same type as that which normally produces that particular proteoglycan. This assures that the correct types of glucose side chain(s) are attached to the core (i.e., protein) of the proteoglycan. In particular, when biglycan is used in the invention, it is preferable that biglycan contains the appropriate GAG side chains. For example, when biglycan is used in the context of muscle cells, it is preferable to produce biglycan in muscle cells, e.g., C2 muscle cells. The biglycan can also be produced in Torpedo cells, e.g., cells from the electric organ of Torpedo.

Cells that can be used for producing a compound of the invention, e.g., a proteoglycan can further be modified to increase the level and/or activity of an enzyme that catalyzes posttranslational modifications, e.g., glycosylations or sulfonations. For example, a cell can be transformed or cotransfected with an expression construct encoding a sulfotransferase, e.g., a chondroitin sulfotransferase, e.g., a chondroitin-6-sulfotransferase (C6ST; Fukuta et al. (1995) *J. Biol. Chem.* 270: 18575), or a nervous system involved sulfotransferase (NSIST), described in Nastuk et al. (1998) *J. Neuroscience* 18: 7167.

Alternatively, a protein core of a proteoglycan can be produced in a prokaryote, which results in a protein without glucose side chains, and the appropriate side chains can be added later, such as by synthetic chemistry. In yet another embodiment, a proteoglycan is produced in one type of eukaryotic cell and the protein can be stripped of its side chains, prior to adding the appropriate side chains. Methods for synthetically adding glycan side chains to a protein are known in the art.

In a preferred embodiment, a recombinant protein of the invention, such as biglycan or decorin, is produced using a vaccinia-based system, as described in Krishnan et al. (1999) *J. Biol. Chem.* 294: 10945 and in Hocking et al. (1996) J. Biol. Chem. 271:19571. Infection of muscle cells with this vector encoding biglycan or decorin for example, results in the production of biglycan or decorin having muscle specific GAG chains. Biophysical studies, such as far UV circular dichroism showed that these recombinant proteins retain their native structure. In an even more preferred embodiment, these recombinant proteins are epitope-tagged, as further described herein, which facilitates co-immunoprecipitation and binding studies.

For example, a proteoglycan of the invention can be produced in a eukaryotic cell using the vaccinia virus/T7 bacteriophage expression system. A recombinant vaccinia virus, vBGN4 encoding the proteoglycan of the invention, e.g., mature biglycan protein, can be expressed as a polyhistidine fusion protein under control of the T7 phage promoter and expressed, e.g., in HT-1080 cells and UMR106 cells, as described in Hocking et al. (1996) *J Biol Chem* 271: 19571-7.

Immortalized cell lines, e.g., muscle cell lines, such as biglycan negative cell lines, can be obtained as described in Jat et al., PNAS (1991) 88: 5096-100; Noble et al., (1992) *Brain Pathology* 2: 39-46. In one embodiment, a H-2K$^{b}$/tsA58 transgenic mouse is used. This mouse is a heterozygote harboring a thermolabile immortalizing gene (the tsA58 mutant of SV40 large T antigen) under the control of an interferon-inducible promoter (this mouse is available at Charles River). When cells containing this gene are cultured, they proliferate indefinitely at 33° C. in the presence of interferon. However, when the temperature is raised to 39° C. (at which temperature the tsA58 antigen is non-functional) and interferon is removed, the cells cease dividing.

This method has been used for growing a wide variety of cell types, including astrocytes, osteoclasts, trabecular network, and colon epithelial cells (Chambers et al., (1993) *PNAS* 90: 5578-82; Groves et al., (1993) *Dev. Biol.* 159: 87-104; Whitehead et al., (1993) *PNAS* 90: 587-91; Noble et al., (1995) *Transgenic Res.* 4: 215-25; Tamm et al., (1999) *Invest. Ophtamol. Vis. Sci.* 40: 1392-403. This technique is well suited for the production of muscle cell lines. For example, in one study alone 65 separate muscle cell lines were derived from animals ranging in age from neonates to four weeks (Morgan et al., (1994) *Dev. Biol.* 162 486-98). These lines were maintained for upwards of 80 generations. Remarkably, they not only formed myotubes when shifted to non-permissive conditions in culture, but also formed muscle when implanted into host mice. The H-2K$^{b}$/tsA58 transgenic method was also used by D. Glass and colleagues to produce a MuSK$^{-/-}$ muscle cell line (Sugiyama et al., (1997) *J. Cell Biol.* 139: 181-91).

To produce conditionally immortalized cell lines, mice having a specific mutation, e.g., a deficiency in biglycan or MuSK, can be crossed with heterozygote H-2K$^{b}$/tsA58 transgenic mice. The crosses are straightforward since only one copy of the gene is required for full activity. Muscle cells from neonatal animals can then be plated out and grown under permissive conditions (33° C. with interferon). Proliferating cells can then be cloned and samples from each line shifted to the non-permissive temperature and tested for their ability to form myotubes. Wild type; decorin$^{-/-}$; biglycan$^{-/0}$; and decorin$^{-/-}$ biglycan$^{-/0}$ cell lines are examples of cell lines which can be obtained using this technique.

In a further embodiment, the compound of the invention is a glycan or polyssacharide. In fact, in certain applications, it may be that in certain cases, the core of a proteoglycan may not be necessary for the desired activity, such as for stabilizing the DAPC by contacting one or more components thereof. For example, it has been shown herein that the GAG side chains of biglycan are necessary for its interaction with α-dystroglycan, indicating that the interaction is likely to be mediated by the GAG side chains.

The compounds of the invention can also be peptidomimetics or small organic molecules, which can be prepared, e.g., based on the structure of the proteoglycan.

Although the preferred method for treating subjects with a biglycan is by administration of the biglycan to the subject (based at least on the efficiency of biglycan when added to cell cultures, as described in the Examples), the proteoglycans of the invention can also be produced in a subject by gene therapy techniques. Thus, e.g., a subject can receive an injection in a muscle (e.g., where the subject has a muscle dystrophy) of a vector encoding a protein or proteoglycan of the invention, such that the vector is capable of entering muscle cells and being expressed therein. Alternatively, the vector can be a viral vector, which is provided with the viral capside and the virus infects the cells, e.g., muscle cells and thereby deliver the vector. Methods and vectors for gene therapy are well known in the art. Illustrative methods are set forth below.

The preferred mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press, 1989) Chapters 16 and 17. In some instances, it may be desirable to express the recombinant fusion proteins by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the -gal containing pBlueBac III).

In yet other embodiments, the subject expression constructs are derived by insertion of the subject gene into viral vectors including recombinant retroviruses, adenovirus, adeno-associated virus, and herpes simplex virus-1, or recombinant bacterial or eukaryotic plasmids. As described in greater detail below, such embodiments of the subject expression constructs are specifically contemplated for use in various in vivo and ex vivo gene therapy protocols.

Retrovirus vectors and adeno-associated virus vectors are generally understood to be the recombinant gene delivery system of choice for the transfer of exogenous genes in vivo, particularly into humans. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, A. D. (1990) Blood 76:271). Thus, recombinant retrovirus can be constructed in which part of the retroviral coding sequence (gag, pol, env) has been replaced by nucleic acid encoding a fusion protein of the present invention rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al., (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include SYMBOL 121 \f "Symbol"Crip, SYMBOL 121 \f. "Symbol" Cre, SYMBOL 121 \f. "Symbol"2 and SYMBOL 121 \f. "Symbol" Am. Retroviruses have been used to introduce a variety of genes into many different cell types, including neural cells, epithelial cells, endothelial cells, lymphocytes, myoblasts, hepatocytes, bone marrow cells, in vitro and/or in vivo (see for example Eglitis et al., (1985) Science 230:1395-1398; Danos and Mulligan, (1988) PNAS USA 85:6460-6464; Wilson et al., (1988) PNAS USA 85:3014-3018; Armentano et al., (1990) PNAS USA 87:6141-6145; Huber et al., (1991) PNAS USA 88:8039-8043; Ferry et al., (1991) PNAS USA 88:8377-8381; Chowdhury et al., (1991) Science 254:1802-1805; van Beusechem et al., (1992) PNAS USA 89:7640-7644; Kay et al., (1992) Human Gene Therapy 3:641-647; Dai et al., (1992) PNAS USA 89:10892-10895; Hwu et al., (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Furthermore, it has been shown that it is possible to limit the infection spectrum of retroviruses and consequently of retroviral-based vectors, by modifying the viral packaging proteins on the surface of the viral particle (see, for example PCT publications WO93/25234, WO94/06920, and WO94/11524). For instance, strategies for the modification of the infection spectrum of retroviral vectors include: coupling antibodies specific for cell surface antigens to the viral env protein (Roux et al., (1989) PNAS USA 86:9079-9083; Julan et al., (1992) J. Gen Virol 73:3251-3255; and Goud et al., (1983) Virology 163:251-254); or coupling cell surface ligands to the viral env proteins (Neda et al., (1991) J. Biol. Chem. 266:14143-14146). Coupling can be in the form of the chemical cross-linking with a protein or other variety (e.g. lactose to convert the env protein to an asialoglycoprotein), as well as by generating fusion proteins (e.g. single-chain antibody/env fusion proteins). This technique, while useful to limit or otherwise direct the infection to certain tissue types, and can also be used to convert an ecotropic vector in to an amphotropic vector.

Another viral gene delivery system useful in the present invention utilizes adenovirus-derived vectors. The genome of an adenovirus can be manipulated such that it encodes a gene product of interest, but is inactivate in terms of its ability to replicate in a normal lytic viral life cycle (see, for example, Berkner et al., (1988) BioTechniques 6:616; Rosenfeld et al., (1991) Science 252:431-434; and Rosenfeld et al., (1992) Cell 68:143-155). Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they are not capable of infecting nondividing cells and can be used to infect a wide variety of cell types, including airway epithelium (Rosenfeld et al., (1992) cited supra), endothelial cells (Lemarchand et al., (1992) PNAS USA 89:6482-6486), hepatocytes (Herz and Gerard, (1993) PNAS USA 90:2812-2816) and muscle cells (Quantin et al., (1992) PNAS USA 89:2581-2584). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham (1986) J. Virol. 57:267). Most replication-defective adenoviral vectors currently in use and therefore favored by the present invention are deleted for all or parts of the viral E1 and E3 genes but retain as much as 80% of the adenoviral genetic material (see, e.g., Jones et al., (1979) Cell 16:683; Berkner et al., supra; and Graham et al., in Methods in Molecular Biology, E. J. Murray, Ed. (Humana, Clifton, N.J., 1991) vol. 7. pp. 109-127). Expression of the inserted chimeric gene can be under control of, for example, the E1A promoter, the major late promoter (MLP) and associated leader sequences, the viral E3 promoter, or exogenously added promoter sequences.

Yet another viral vector system useful for delivery of the subject chimeric genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. (1992) 158:97-129). It is also one of the few viruses that may integrate its DNA into non-dividing cells, and exhibits a high frequency of stable integration (see for example Flotte et al., (1992) Am. J. Respir. Cell. Mol. Biol. 7:349-356; Samulski et al., (1989) J. Virol. 63:3822-3828; and McLaughlin et al., (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al., (1985) Mol. Cell. Biol. 5:3251-3260 can be used to introduce DNA into cells. A variety of nucleic acids have been introduced into different cell types using AAV vectors (see for example Hermonat et al., (1984) PNAS USA 81:6466-6470; Tratschin et al., (1985) Mol. Cell. Biol. 4:2072-2081; Wondisford et al., (1988) Mol. Endocrinol. 2:32-39; Tratschin et al., (1984) J. Virol. 51:611-619; and Flotte et al., (1993) J. Biol. Chem. 268:3781-3790).

Other viral vector systems that may have application in gene therapy have been derived from herpes virus, vaccinia virus, and several RNA viruses. In particular, herpes virus vectors may provide a unique strategy for persistence of the recombinant gene in cells of the central nervous system and ocular tissue (Pepose et al., (1994) Invest Ophthalmol Vis Sci 35:2662-2666).

In addition to viral transfer methods, such as those illustrated above, non-viral methods can also be employed to cause expression of a protein in the tissue of an animal. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the gene by the targeted cell. Exemplary gene delivery systems of this type include liposomal derived systems, poly-lysine conjugates, and artificial viral envelopes.

In a representative embodiment, a gene encoding a protein of interest can be entrapped in liposomes bearing positive charges on their surface (e.g., lipofectins) and (optionally) which are tagged with antibodies against cell surface antigens of the target tissue (Mizuno et al., (1992) No Shinkei Geka 20:547-551; PCT publication WO91/06309; Japanese patent application 1047381; and European patent publication EP-A-43075). For example, lipofection of muscle, neural or cardiac cells can be carried out using liposomes tagged with monoclonal antibodies against specific tissue-associated antigens (Mizuno et al., (1992) Neurol. Med. Chir. 32:873-876).

In yet another illustrative embodiment, the gene delivery system comprises an antibody or cell surface ligand which is cross-linked with a gene binding agent such as poly-lysine (see, for example, PCT publications WO93/04701, WO92/22635, WO92/20316, WO92/19749, and WO92/06180). For example, any of the subject gene constructs can be used to transfect specific cells in vivo using a soluble polynucleotide carrier comprising an antibody conjugated to a polycation, e.g. poly-lysine (see U.S. Pat. No. 5,166,320). It will also be appreciated that effective delivery of the subject nucleic acid constructs via mediated endocytosis can be improved using agents which enhance escape of the gene from the endosomal structures. For instance, whole adenovirus or fusogenic peptides of the influenza HA gene product can be used as part of the delivery system to induce efficient disruption of DNA-containing endosomes (Mulligan et al., (1993) Science 260-926; Wagner et al., (1992) PNAS USA 89:7934; and Christiano et al., (1993) PNAS USA 90:2122).

Nucleic acids encoding biglycan proteins can also be administered to a subject as "naked" DNA, as described, e.g., in U.S. Pat. No. 5,679,647 and related patents by Carson et al., in WO 90/11092 and Feigner et al. (1990) Science 247: 1465.

In clinical settings, the gene delivery systems can be introduced into a patient by any of a number of methods, each of which is familiar in the art. For instance, a pharmaceutical preparation of the gene delivery system can be introduced systemically, e.g. by intravenous injection, and specific transduction of the construct in the target cells occurs predominantly from specificity of transfection provided by the gene delivery vehicle, cell-type or tissue-type expression due to the transcriptional regulatory sequences controlling expression of the gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al., (1994) PNAS USA 91: 3054-3057).

The gene encoding the proteoglycan of the invention can be under the control of a constitutive, or inducible promoter. These are well known in the art.

Methods for determining whether a compound has a biological activity of a biglycan protein are described in the Examples. A biological activity of a biglycan protein is intended to refer to one or more of: the ability to maintain the integrity of a plasma membrane; the ability to stabilize DAPCs on plasma membranes; the ability to bind to one or more components of DAPCs; e.g., binding to α-dystroglycan, binding to a sarcoglycan component, such as α-sarcoglycan; phosphorylation of α-sarcoglycan; binding to MuSK; stimulating the formation of neuromuscular junctions, such as by stimulating postsynaptic differentiation; stimulating AChR aggregation; stimulation of MuSK phosphorylation and potentiation of agrin-induced MuSK phosphorylation. Such methods can further be adapted for screening libraries of compounds for identifying compounds having one or more of the above-described activities.

Breakdown of cytoplasmic membranes, e.g., the presence of "leaky membranes" can be determined by assays which measure the release of creatine kinase or the absorption of Evans Blue dye, as described, e.g., in Tinsley et al. (1996) *Nature* 384: 349 and Straub et al. (1997) *J. Cell Biol.* 139: 375).

The compounds of the invention can also be tested in a variety of animal models, in particular the mdx mice, which are dystrophin negative (see Examples).

Methods of Treatment

General:

The invention provides therapeutic and prophylactic methods of treatment of disorders including muscular, neuromuscular, and neurological disorders. Therapeutic methods are intended to eliminate or at least reduce at least one symptom of a disease or disorder, and preferably cure the disease or disorder. Prophylactic methods include those intended to prevent the appearance of a disease or disorder, i.e., a method which is intended to combat the appearance of the disease or disorder.

As described herein, biglycan was shown to bind to alpha-dystroglycan and to sarcoglycans, and thereby functions as a link between various components of DAPCs. Furthermore, biglycan levels were found to be high in muscle cells of mice lacking dystrophin (mdx mice, which are a model of muscular dystrophy). Since the absence of dystrophin in muscle cells is known to destabilize the cytoplasmic membrane, the upregulation of biglycan in dystrophin negative muscle cells may be a compensatory mechanism for the absence of dystrophin. Accordingly, the invention provides for methods for preventing and treating diseases or disorders that are associated with plasma membrane instability or organization, in particular, an instability resulting from an abnormal DAPC on the plasma membrane. Since the DAPC is found on the membrane of muscle cells, diseases that can be treated according to the invention include diseases of the muscle, such as muscular dystrophies and muscle atrophy.

Furthermore, since DAPCs are also found on other cell types, the invention also provides methods for treating diseases associated with any abnormal DAPC. For example, DAPC are present in the brain, and since, in addition, agrin has been found in senile plaques in patients with Alzheimer's disease, neurological diseases can also be treated or prevented according to the methods of the invention. A further indication that neurological disorders can be treated or prevented according to the methods described herein is based on the observation that patients with muscular dystrophy often also suffer from peripheral and central nervous system disorder. Accordingly, about one third of patients with Duchenne Muscular Dystrophy have a mental affliction, in particular, mental retardation. Thus, dystrophin, and hence, DAPCs, are believed to play a role in the nervous system.

Patients with Duchenne's Muscular Dystrophy also have diaphragm problems, indicating a role for dystrophin, and possibly DAPCs, in diaphragms. Thus, therapeutics of the invention would also find an application in disorders associated with diaphragm abnormalities.

It should be noted that diseases that can be treated or prevented include not only those in which biglycan is abnormal, but more generally any disease or condition that is associated with a defect that can be improved or cured by biglycan. In particular, diseases that are characterized by a defect or an abnormality in any component of the DAPC or component associated therewith, thereby resulting, e.g., in an unstable plasma membrane, can be treated or prevented according to the methods of the invention, provided that the proteoglycan of the invention can at least partially cure the defect resulting from the deficient component. In particular, diseases that can be treated according to the method of the invention include any disease associated with an unstable DAPC, which can be rendered more stable by the presence of a proteoglycan of the invention.

Furthermore, since biglycan was shown to bind to, and phosphorylates MuSK, a receptor which is known for mediating agrin-induced stimulation of neuromuscular junction formation, in particular postsynaptic membrane differentiation, to potentiate agrin-induced AChR aggregation, and to correct a defective agrin-induced AChR aggregation in myotubes of biglycan negative mice by its addition to the myotubes, the invention also provides methods for preventing and treating, diseases or disorders of neuromuscular junctions, such as neuromuscular disorders. Most interestingly, exogenously added biglycan was shown to be able to correct a defective agrin-induced AChR aggregation in myotubes of biglycan negative mice.

Exemplary Diseases and Disorders:

Diseases or disorders that are characterized by a destabilization or improper organization of the plasma membrane of specific cell types include muscular dystrophies (MDs), a group of genetic degenerative myopathies characterized by weakness and muscle atrophy without nervous system involvement. The three main types are pseudohypertrophic (Duchenne, Becker), limb-girdle, and facioscapulohumeral. For example, muscular dystrophies and muscular atrophies are characterized by a breakdown of the muscle cell membrane, i.e., they are characterized by leaky membranes, which are believed to result from a mutation in a component of the DAPC, i.e., dystrophin. Mutations in the sarcoglycans are also known to result in muscular dystrophies and leaky membranes. Accordingly, the invention provides for methods for treating or preventing diseases associated with mutations in dystrophin and/or in sarcoglycans or other component of DAPCs, in particular muscular dystrophies.

Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is wheelchair-bound by age 13 and usually dies by age 20.

Another type of dystrophy that can be treated according to the methods of the invention includes congenital muscular dystrophy (CMD), a very disabling muscle disease of early clinical onset, is the most frequent cause of severe neonatal hypotonia. Its manifestations are noticed at birth or in the first months of life and consist of muscle hypotonia, often associated with delayed motor milestones, severe and early contractures and joint deformities. Serum creatine kinase is raised, up to 30 times the normal values, in the early stage of the disease, and then rapidly decreases. The histological changes in the muscle biopsies consist of large variation in the size of muscle fibers, a few necrotic and regenerating fibers, marked increase in endomysial collagen tissue, and no specific ultrastructural features. The diagnosis of CMD has been based on the clinical picture and the morphological changes in the muscle biopsy, but it cannot be made with certainty, as other muscle disorders may present with similar clinico-pathological features. Within the group of diseases classified as CMD, various forms have been individualized. The two more common forms are the occidental and the Japanese, the latter being associated with severe mental disturbances, and usually referred to as Fukuyama congenital muscular dystrophy (FCMD).

One form of congenital muscular dystrophy (CMD) has recently been characterized as being caused by mutations in the laminin alpha 2-chain gene. Laminin is a protein that associates with DAPCs. Thus, the invention also provides methods for treating diseases that are associated with abnormal molecules which normally associate with DAPCs.

Other muscular dystrophies within the scope of the invention include limb-girdle muscular dystrophy (LGMD), which represents a clinically and genetically heterogeneous class of disorders. These dystrophies are inherited as either autosomal dominant or recessive traits. An autosomal dominant form, LGMD1A, was mapped to 5q31-q33 (Speer, M. C. et al., Am. J. Hum. Genet. 50:1211, 1992; Yamaoka, L. Y. et al., Neuromusc. Disord. 4:471, 1994), while six genes involved in the autosomal recessive forms were mapped to 15q15.1 (LGMD2A) (Beckmann, J. S. et al., C. R. Acad. Sci. Paris 312:141, 1991), 2p16-p13 (LGMD2B) (Bashir, R. et al., Hum. Mol. Genet. 3:455, 1994), 13q12 (LGMD2C) (Ben Othmane, K. et al., Nature Genet. 2:315, 1992; Azibi, K. et al., Hum. Mol. Genet. 2:1423, 1993), 17g12-g21.33 (LGMD2D) (Roberds, S. L. et al., Cell 78:625, 1994; McNally, E. M., et. al., Proc. Nat. Acad. Sci. U.S.A. 91:9690, 1994), 4q12 (LG1MD2E) (Lim, L. E., et. al., Nat. Genet. 11:257, 1994; Bonnemann, C. G. et al. Nat. Genet. 11:266, 1995), and most recently to 5q33-q34 (LGMD2F) (Passos-Bueno, M. R., et. al., Hum. Mol. Genet. 5:815, 1996). Patients with LGMD2C, 2D and 2E have a deficiency of components of the sarcoglycan complex resulting from mutations in the genes encoding gamma-, alpha-, and beta-sarcoglycan, respectively. The gene responsible for LGMD2A has been identified as the muscle-specific calpain, whereas the genes responsible for LGMD1A, 2B and 2F are still unknown.

Yet other types of muscular dystrophies that can be treated according to the methods of the invention include Welander distal myopathy (WDM), which is an autosomal dominant myopathy with late-adult onset characterized by slow progression of distal muscle weakness. The disorder is considered a model disease for hereditary distal myopathies. The disease is linked to chromosome 2p13. Another muscular dystrophy is Miyoshi myopathy, which is a distal muscular dystrophy that is caused by mutations in the recently cloned gene dysferlin, gene symbol DYSF (Weiler et al. (1999) *Hum Mol Genet* 8: 871-7). Yet other dystrophies include Hereditary Distal Myopathy, Benign Congenital Hypotonia, Central Core disease, Nemaline Myopathy, and Myotubular (centronuclear) myopathy.

Other diseases that can be treated or prevented according to the methods of the invention include those characterized by tissue atrophy, e.g., muscle atrophy, other than muscle atrophy resulting from muscular dystrophies, provided that the atrophy is stopped or slowed down upon treatment with a therapeutic of the invention. Furthermore, the invention also provides methods for reversing tissue atrophies, e.g., muscle atrophies. This can be achieved, e.g., by providing to the atrophied tissue a therapeutic of the invention, such as DAG-125 or mammalian ortholog thereof, or biglycan.

Muscle atrophies can result from denervation (loss of contact by the muscle with its nerve) due to nerve trauma; degenerative, metabolic or inflammatory neuropathy (e.g., GuillianBarre syndrome), peripheral neuropathy, or damage to nerves caused by environmental toxins or drugs. In another embodiment, the muscle atrophy results from denervation due to a motor neuronopathy. Such motor neuronopathies include, but are not limited to: adult motor neuron disease, including Amyotrophic Lateral Sclerosis (ALS or Lou Gehrig's disease); infantile and juvenile spinal muscular atrophies, and autoimmune motor neuropathy with multifocal conduction block. In another embodiment, the muscle atrophy results from chronic disuse. Such disuse atrophy may stem from conditions including, but not limited to: paralysis due to stroke, spinal cord injury; skeletal immobilization due to trauma (such as fracture, sprain or dislocation) or prolonged bed rest. In yet another embodiment, the muscle atrophy results from metabolic stress or nutritional insufficiency, including, but not limited to, the cachexia of cancer and other chronic illnesses, fasting or rhabdomyolysis, endocrine disorders such as, but not limited to, disorders of the thyroid gland and diabetes.

Since muscle tissue atrophy and necrosis are often accompanied by fibrosis of the affected tissue, the reversal or the inhibition of atrophy or necrosis can also result in an inhibition or reversal of fibrosis.

In addition, the therapeutics of the invention may be of use in the treatment of acquired (toxic or inflammatory) myopathies. Myopathies which occur as a consequence of an inflammatory disease of muscle, include, but not limited to polymyositis and dermatomyositis. Toxic myopathies may be due to agents, including, but are not limited to adiodarone, chloroquine, clofibrate, colchicine, doxorubicin, ethanol, hydroxychloroquine, organophosphates, perihexyline, and vincristine.

Neuromuscular dystrophies within the scope of the invention include myotonic dystrophy. Myotonic dystrophy (DM; or Steinert's disease) is an autosomal dominant neuromuscular disease which is the most common form of muscular dystrophy affecting adults. The clinical picture in DM is well established but exceptionally variable (Harper, P. S., Myotonic Dystrophy, 2nd ed., W. B. Saunders Co., London, 1989). Although generally considered a disease of muscle, with myotonia, progressive weakness and wasting, DM is characterized by abnormalities in a variety of other systems. DM patients often suffer from cardiac conduction defects, smooth muscle involvement, hypersomnia, cataracts, abnormal glucose response, and, in males, premature balding and testicular atrophy (Harper, P. S., Myotonic Dystrophy, 2nd ed., W. B. Saunders Co., London, 1989). The mildest form, which is occasionally difficult to diagnose, is seen in middle or old age and is characterized by cataracts with little or no muscle involvement. The classical form, showing myotonia and muscle weakness, most frequently has onset in early adult life and in adolescence. The most severe form, which occurs congenitally, is associated with generalized muscular hypoplasia, mental retardation, and high neonatal mortality. This disease and the gene affected are further described in U.S. Pat. No. 5,955,265.

Another neuromuscular disease is spinal muscular atrophy ("SMA"), which is the second most common neuromuscular disease in children after Duchenne muscular dystrophy. SMA refers to a debilitating neuromuscular disorder which primarily affects infants and young children. This disorder is caused by degeneration of the lower motor neurons, also known as the anterior horn cells of the spinal cord. Normal lower motor neurons stimulate muscles to contract. Neuronal degeneration reduces stimulation which causes muscle tissue to atrophy (see, e.g., U.S. Pat. No. 5,882,868).

The above-described muscular dystrophies and myopathies are skeletal muscle disorders. However, the invention also pertains to disorders of smooth muscles, e.g., cardiac myopathies, including hypertrophic cardiomyopathy, dilated cardiomyopathy and restrictive cardiomyopathy. At least certain smooth muscles, e.g., cardiac muscle, are rich in sarcoglycans. Mutations in sarcoglycans can result in sarcolemmal instability at the myocardial level (see, e.g., Melacini (1999) *Muscle Nerve* 22: 473). For example, animal models in which a sarcoglycan is mutated show cardiac creatine kinase elevation. In particular, it has been shown that delta-sarcoglycan (Sgcd) null mice develop cardiomyopathy with focal areas of necrosis as the histological hallmark in cardiac and skeletal muscle. The animals also showed an absence of the sarcoglycan-sarcospan (SG-SSPN) complex in skeletal and cardiac membranes. Loss of vascular smooth muscle SG-SSPN complex was associated with irregularities of the coronary vasculature. Thus, disruption of the SG-SSPN complex in vascular smooth muscle perturbs vascular function, which initiates cardiomyopathy and exacerbates muscular dystrophy (Coral-Vazquez et al. (1999) *Cell* 98: 465).

Similarly to delta-sarcoglycan negative mice, mice lacking gamma-sarcoglycan showed pronounced dystrophic muscle changes in early life (Hack et al. (1998) *J Cell Biol* 142: 1279). By 20 wk of age, these mice developed cardiomyopathy and died prematurely. Furthermore, apoptotic myonuclei were abundant in skeletal muscle lacking gamma-sarcoglycan, suggesting that programmed cell death contributes to myofiber degeneration. Vital staining with Evans blue dye revealed that muscle lacking gamma-sarcoglycan developed membrane disruptions like those seen in dystrophin-deficient muscle. It was also shown that the loss of gamma-sarcoglycan produced secondary reduction of beta- and delta-sarcoglycan with partial retention of alpha- and epsilon-sarcoglycan, indicating that beta-, gamma-, and delta-sarcoglycan function as a unit. Since the other components of the cytoplasmic membrane complex were functional, the complex could be stabilized by the presence of a therapeutic of the invention.

In addition to animal models, certain cardiomyopathies in humans have been linked to mutations in dystrophin, dystroglycans or sarcoglycans. For example, dystrophin has been identified as the gene responsible for X-linked dilated cardiomyopathy (Towbin J. A. (1998) *Curr Opin Cell Biol* 10: 131, and references therein). In this case, the dystrophin gene contained a 5'-mutation which results in cardiomyopathy without clinically-apparent skeletal myopathy (Bies et al. (1997) *J Mol Cell Cardiol* 29: 3175.

Furthermore, cardiomyopathy was also found in subjects having Duchenne's Muscular Dystrophy (associated with a mutated dystrophin), or other types of muscular dystrophies, such as Limb Girdle Muscular Dystrophy. For example, dilated cardiomyopathy was present in one autosomal dominant case and in three advanced autosomal recessive or sporadic patients, of whom two were found to have alpha sarcoglycan deficiency. Two of these three patients and three other cases showed ECG abnormalities known to be characteristic of the dystrophinopathies. A strong association between the absence of alpha sarcoglycan and the presence of dilated cardiomyopathy was found. In six autosomal dominant cases there were atrioventricular (AV) conduction disturbances, increasing in severity with age and in concomitant presence of muscle weakness. Pacemaker implantation was necessary in certain of these patients (see van der Kooi (1998) *Heart* 79: 73).

Therapeutics of the invention can also be used to treat or prevent cardiomyopathy, e.g., dilated cardiomyopathy, of viral origin, e.g., resulting from an enterovirus infection, e.g., a Coxsackievirus B3. It has been shown that purified Coxsackievirus protease 2A cleaves dystrophin in vitro and during Coxsackievirus infection of cultured myocytes and in infected mouse hearts, leading to impaired dystrophin function (Badorff et al. (1999) *Nat Med* 5: 320. Cleavage of dystrophin results in disruption of the dystrophin-associated glycoproteins alpha-sarcoglycan and beta-dystroglycan. Thus, cardiomyopathy could be prevented or reversed by administration of a therapeutic of the invention to a subject having been infected with a virus causing cardiomyopathy, e.g., by disruption of dystrophin or a protein associated therewith. Administration of the therapeutic could restabilize or reorganize the cytoplasmic membrane of affected cardiac cells.

Thus, the therapeutics of the invention can also be used to prevent or to treat smooth muscle disorders, such as cardiac myopathies, and to stop atrophy and/or necrosis of cardiac smooth muscle tissue. The treatment can also be used to promote survival of myocytes.

Neurological disorders that can be treated according to the methods of the invention include polymyositis, and neurogenic disorders. Another neurological disease that can be treated is Alzheimer's disease.

Other diseases that can be treated according to the methods of the invention include those in which the proteoglycan of the invention is present at abnormal levels, or has an abnormal activity, relative to that in normal subjects. For example, a disease or disorder could be caused by a lower level of biglycan, resulting in, e.g., unstable cytoplasmic membranes. Alternatively, a disease or disorder could result from an abnormally high level or activity of biglycan, resulting in, e.g., overstimulation of MuSK or over-aggregation of AChRs (see below).

Yet other diseases or disorders that are within the scope of the invention include those that are associated with an abnormal interaction between a proteoglycan of the invention and another molecule (other than those of the DAPC or MuSK), e.g., a complement factor, such as Clq. For example, it has been shown that Clq interacts with biglycan (Hocking et al. (1996) *J. Biol. Chem.* 271: 19571). It is also known that binding of Clq to cell surfaces mediates a number of biological activities including enhancement of phagocytosis and stimulation of superoxide production. Thus, since biglycan binds to Clq, biglycan or another proteoglycan or core thereof, of the invention could be used to inhibit the binding of Clq to its receptor on cell surfaces to inhibit one or more of such biological activities. In addition, compounds of the invention which inhibit the interaction between Clq or other complement component and a cell surface can also be used to inhibit complement mediated necrosis of the cells and tissues containing such cells.

Also within the scope of the invention are methods for preventing or inhibiting infections of cells by microorganisms, e.g., viruses. For example, it has been shown that dystroglycan is a receptor via which certain microorganisms enter eukaryotic cells (*Science* (1998) 282: 2079). Thus, by administrating to a subject a therapeutic of the invention which occupies the site on dystroglycan molecules to which the microorganism binds, entering of the microorganism into the cell can be inhibited. This method can be used, e.g., to prevent or inhibit Lassa Fever virus and lymphocytic choriomeningitis virus (LCMV) infection, as well as infection by other arenaviruses, including Oliveros, and Mobala. Soluble α-dystroglycan was shown to block both LCMV and LFV infection (*Science* (1998) 282: 2079).

In addition to cell cultures, e.g., established from patients having, e.g., a muscular dystrophy, various animal models can be used to select the most appropriate therapeutic for treating a disease. In particular, to identify a therapeutic for use in preventing or treating a muscular dystrophy or cardiomyopathy associated with a mutated or absent DAPC component or, mice having mutated versions of these proteins, or having null mutations in the genes encoding these proteins, can be used. For example, mice having a disrupted sarcoglycan, such as delta-sarcoglycan, can be used. Such mice are described, e.g., Coral-Vazquez et al. (1999) *Cell* 98: 465. Alternatively, mice deficient in dystrophin (mdx mice), or in alpha- or gamma-sarcoglycans can be used. Such mice have been described herein and in the literature. Additional mice can be made according to known methods in the art. In an illustrative embodiment to identify therapeutics, different therapeutics are administered to delta-sarcoglycan null mice, and the effect of the therapeutics are evaluated by studying cardiac function. Another animal model that can be used for this purpose is the cardiomyopathic hamster that does not express delta-sarcoglycan due to a genomic deletion. This rat is an animal model for autosomal recessive cardiomyopathy, and is further described in Sakamoto et al. *FEBS Lett* 1999 (1999) 44: 124.

Effective Dose and Administration of Therapeutic Compositions

The above-described diseases or disorders can be treated or ameliorated in a subject by administering to the subject a pharmaceutically efficient amount of a compound of the invention. Depending on whether the disease is caused by higher levels or activity or by lower levels or activity of biglycan, an agonist or an antagonist biglycan therapeutic is administered to a subject having the disease. Although a person of skill in the art will be able to predict which therapeutic to administer for treating any of the diseases of the invention, tests can be performed to determine the appropriate therapeutic to administer. Such tests can use, e.g., animal models of the disease. Alternatively, in cases where diseases are due to a mutation in, e.g., biglycan, in vitro tests can be undertaken to determine the effect of the mutation. This will allow the determination of what type of therapeutic should be administered to a subject having this type of mutation.

The therapeutic can also be a compound which modulates, i.e., inhibits or stimulates, expression of biglycan, or mammalian ortholog thereof, or biglycan. Such compounds can be identified as further described herein.

Another manner of administering a therapeutic of the invention to a subject is by preparing cells expressing and secreting the proteoglycan of interest, inserting the cells into a matrix and administering this matrix to the subject at the desired location. Thus, cells engineered in accordance with this invention may also be encapsulated, e.g. using conventional biocompatible materials and methods, prior to implantation into the host organism or patient for the production of a therapeutic protein. See e.g. Hguyen et al, Tissue Implant Systems and Methods for Sustaining viable High Cell Densities within a Host, U.S. Pat. No. 5,314,471 (Baxter International, Inc.); Uludag and Sefton, 1993, J. Biomed. Mater. Res. 27(10):1213-24 (HepG2 cells/hydroxyethyl methacrylate-methyl methacrylate membranes); Chang et al, 1993, Hum Gene Ther 4(4):433-40 (mouse Ltk-cells expressing hGH/immunoprotective perm-selective alginate microcapsules; Reddy et al, 1993, J Infect Dis 168(4):1082-3 (alginate); Tai and Sun, 1993, FASEB J 7(10:1061-9 (mouse fibroblasts expressing hGH/alginate-poly-L-lysine-alginate membrane); Ao et al, 1995, Transplanataion Proc. 27(6):3349, 3350 (alginate); Rajotte et al, 1995, Transplantation Proc. 27(6):3389 (alginate); Lakey et al, 1995, Transplantation Proc. 27(6):3266 (alginate); Korbutt et al, 1995, Transplantation Proc. 27(6):3212 (alginate); Dorian et al, U.S. Pat. No. 5,429,821 (alginate); Emerich et al, 1993, Exp Neurol 122 (1):37-47 (polymer-encapsulated PC12 cells); Sagen et al, 1993, J Neurosci 13(6):2415-23 (bovine chromaffin cells encapsulated in semipermeable polymer membrane and implanted into rat spinal subarachnoid space); Aebischer et al, 1994, Exp Neurol 126(2):151-8 (polymer-encapsulated rat PC12 cells implanted into monkeys; see also Aebischer, WO 92/19595); Savelkoul et al, 1994, J Immunol Methods 170 (2):185-96 (encapsulated hybridomas producing antibodies; encapsulated transfected cell lines expressing various cytokines); Winn et al, 1994, PNAS USA 91(6):2324-8 (engineered BHK cells expressing human nerve growth factor encapsulated in an immunoisolation polymeric device and transplanted into rats); Emerich et al, 1994, Prog Neuropsychopharmacol Biol Psychiatry 18(5):935-46 (polymer-encapsulated PC12 cells implanted into rats); Kordower et al, 1994, PNAS USA 91(23):10898-902 (polymer-encapsulated engineered BHK cells expressing hNGF implanted into monkeys) and Butler et al WO 95/04521 (encapsulated device). The cells may then be introduced in encapsulated form into an animal host, preferably a mammal and more preferably a human subject in need thereof. Preferably the encapsulating material is semipermeable, permitting release into the host of secreted proteins produced by the encapsulated cells. In many embodiments the semipermeable encapsulation renders the encapsulated cells immunologically isolated from the host organism in which the encapsulated cells are introduced. In those embodiments the cells to be encapsulated may express one or more proteoglycans of the host species and/or from viral proteins or proteins from species other than the host species.

Alternatively, the therapeutic is a nucleic acid encoding the core of a proteoglycan of the invention. Thus, a subject in need thereof, may receive a dose of viral vector encoding the protein of interest, which may be specifically targeted to a specific tissue, e.g., a dystrophic tissue. The vector can be administered in naked form, or it can be administered as a viral particle (further described herein). For this purpose, various techniques have been developed for modification of target tissue and cells in vivo. A number of viral vectors have been developed, such as described above, which allow for transfection and, in some cases, integration of the virus into the host. See, for example, Dubensky et al. (1984) Proc. Natl. Acad. Sci. USA 81, 7529-7533; Kaneda et al., (1989) Science 243, 375-378; Hiebert et al. (1989) Proc. Natl. Acad. Sci. USA 86, 3594-3598; Hatzoglu et al. (1990) J. Biol. Chem. 265, 17285-17293 and Ferry, et al. (1991) Proc. Natl. Acad. Sci. USA 88, 8377-8381. The vector may be administered by injection, e.g. intravascularly or intramuscularly, inhalation, or other parenteral mode. Non-viral delivery methods such as administration of the DNA via complexes with liposomes or by injection, catheter or biolistics may also be used.

In yet another embodiment, cells are obtained from a subject, modified ex vivo, and introduced into the same or a different subject. Additional methods of administration of the therapeutic compounds are set forth below.

Toxicity:

Toxicity and therapeutic efficacy of compounds of the invention can be determined by standard pharmaceutical procedures in cell cultures or experimental animals, e.g., for determining The $Ld_{50}$ (The Dose Lethal To 50% Of The Population) And The $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. In particular, where the therapeutic is administered for potentiating AChR aggregation, it is desirable to establish the dose that will result in stimulation, if desired, or inhibition, if desired. Tests can then be continued in medical tests. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical Compositions:

Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

In clinical settings, a gene delivery system for the therapeutic gene encoding a proteoglycan of the invention can be introduced into a patient by any of a number of methods, each of which is familiar in the art. For instance, a pharmaceutical preparation of the gene delivery system can be introduced systemically, e.g., by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g., Chen et al. (1994) *PNAS* 91: 3054-3057). A gene encoding a proteoglycan of the invention can be delivered in a gene therapy construct by electroporation using techniques described, for example, by Dev et al. ((1994) *Cancer Treat Rev* 20:105-115).

A preferred mode of delivering DNA to muscle cells includes using recombinant adeno-associated virus vectors, such as those described in U.S. Pat. No. 5,858,351. Alternatively, genes have been delivered to muscle by direct injection of plasmid DNA, such as described by Wolff et al. (1990) *Science* 247:1465-1468; Acsadi et al. (1991) *Nature* 352:815-818; Barr and Leiden (1991) *Science* 254:1507-1509. However, this mode of administration generally results in sustained but generally low levels of expression. Low but sustained expression levels are expected to be effective for practicing the methods of the invention.

The pharmaceutical preparation of the gene therapy construct or compound of the invention can consist essentially of the gene delivery system in an acceptable diluent, or can comprise a slow release matrix in which the gene delivery vehicle or compound is imbedded. Alternatively, where the complete gene delivery system can be produced intact from recombinant cells, e.g., retroviral vectors, the pharmaceutical preparation can comprise one or more cells which produce the gene delivery system.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Diagnostic Methods

Based at least on the observation that biglycan binds to at least one component of DAPCs, protein complexes which are critical for maintaining the integrity of plasma membranes, the invention provides diagnostic methods for determining whether a subject has or is likely to develop a disease or condition which is characterized by, or associated with, plasma membrane instability, in particular, abnormal or unstable DAPCs, such as muscular dystrophies. Furthermore, it has been observed in an animal model for muscular dystrophy, which lacks dystrophin, that the amount of the proteoglycan biglycan is elevated, and thereby believed to be a compensatory mechanism.

Furthermore, based at least on the observation that biglycan binds to, and phosphorylates MuSK and potentiates agrin-induced MuSK phosphorylation, and that biglycan stimulates agrin-mediated AChR aggregation, the invention also provides diagnostic methods for determining whether a subject has or is likely to develop a disease or condition which is characterized by abnormal synapses or neuromuscular junctions, e.g., neurological or neuromuscular diseases.

Accordingly, the identification of abnormal levels or activity of the proteoglycan of the invention in a subject would indicate that the subject has, or is likely to develop a disease or condition relating to abnormal or unstable DAPCs. Diseases can be characterized by a high levels of proteoglycan of the invention, e.g., if the cell compensates for the lack of another DAPC component or molecule associating therewith, e.g., as seen in dystrophin negative mice. Alternatively, a high level or activity of proteoglycan of the invention can at least be part of the cause of the disease.

In addition, an elevated level or activity of a proteoglycan of the invention could be associated with, or be at least in part, the cause of neurological or neuromuscular diseases, e.g., by overstimulating AChR aggregation and/or activating MuSK.

Diseases are also likely to be caused or associated with a lower level or activity of proteoglycan of the invention, which may, e.g., cause DAPCs to be more unstable than those on cells of subjects having a normal amount or activity of the proteoglycan of the invention. Accordingly, a lower level or activity of the proteoglycan of the invention in cells of a subject would result in leaky membranes.

A lower level or activity of the proteoglycan of the invention could also result in insufficient AChR aggregation and/or insufficient MuSK activation, thereby resulting in abnormal synapses or neuromuscular junctions. Such situations can thus result in neurological or neuromuscular diseases, and result, e.g., in atrophy of tissues.

As used herein, the term "diagnostic assay" refers to the specific use of the methods described herein to identify an individual predisposed to a disease, such as a muscular disorder, a neuromuscular disorder or a neurological disorder. Such diagnostic assays are particularly useful as prenatal diagnostic assays, which can be used to determine whether a fetus is predisposed to one or more of these disorders. For prenatal diagnosis, for example, a sample can be obtained by biopsy of muscle tissue from the fetus or by biopsy of placenta from the pregnant mother.

In one embodiment, the method comprises determining the level of, or the biological activity of a proteoglycan of the invention relative to that in non affected subjects, or determining whether the proteoglycan or gene encoding it contains a mutation, or abnormal glycan side chains.

A patient sample may be any cell, tissue, or body fluid but is preferably muscle tissue, cerebrospinal fluid, blood, or a blood fraction such as serum or plasma. As used herein, the term "sample" refers to a specimen obtained from a subject, which can be a human subject. In general, a tissue sample, which can be obtained, for example, by biopsy of muscle or placenta of an individual suspected of being predisposed to a disorder, is a suitable sample. In many cases, it is useful to prepare the sample as a tissue section, which can be examined by histologic analysis. Alternatively, proteins or nucleic acids can be extracted from a sample and can be examined using methods such as gel electrophoresis and appropriate "blotting" methods, which are well known in the art and described in detail below.

A sample can be obtained from a normal subject or from a test subject, who is suspected of being predisposed to a disorder, such as a muscular, neuromuscular or neurological disorder, and is being examined for altered expression or localization of the proteoglycan of the invention or altered expression of the mRNA encoding the proteoglycan of the invention.

A sample obtained from a normal subject can be used as a "control" sample, which is useful for comparison with a sample obtained from a test subject. A control sample can be, for example, a muscle sample or a placenta sample, which is obtained from an age- and sex-matched individual who does not exhibit and is not predisposed to a disorder, such as a muscular, neuromuscular, or neurological disorder. A control sample exhibits a level of expression and a pattern of expression of the proteoglycan of the invention and a level of expression of the proteoglycan mRNA that is characteristic of the human population in general and does not significantly deviate from the normal levels of expression or pattern of localization expected for a person in the population. It is expected that, after a statistically significant number of control samples have been examined, an amount of expression of the proteoglycan of the invention per unit of a sample will be determined to be normal for a control sample. As used herein, a "normal" amount of proteoglycan of the invention in a control sample means an amount that is within an expected range for a person that is not predisposed to a disorder, e.g., a muscular, neuromuscular, or neurological disorder.

Altered expression of the proteoglycan of the invention in a sample obtained from a test subject can be identified qualitatively by visually comparing, for example, photomicrographs of an immunohistochemically stained control sample with the sample obtained from the test subject. Alternatively, altered expression of proteoglycan of the invention can be measured quantitatively using, for example, densitometric analysis. Altered expression of proteoglycan of the invention protein also can be determined using methods of gel electrophoresis and, if desired, immunoblot analysis. Such methods are well known in the art.

In the diagnostic method of the present invention, a muscle biopsy sample is obtained from an individual to be tested. Typically, an individual to be tested according to the diagnostic assays of the invention is an individual who is at risk of having a disorder, e.g., a muscular, neuromuscular, or neurological disorder, for example, a person from a family at risk, or a person showing one or more symptoms of such disorders. In the case of muscular or neuromuscular disorders, muscle samples can be obtained from patients by surgical biopsy. The site of biopsy can be any skeletal muscle suspected of being dystrophic. Muscle groups about the shoulder and pelvic girdles, however, are the most affected and are likely to be the most common site of biopsy. Such muscle samples are analyzed for the presence and/or biological activity of the proteoglycan of the invention, and can also be analyzed by antibody staining to determine levels of dystrophin, dystrophin-associated proteins. To ensure that control and experimental extracts contain substantially similar quantities of protein, extracts are separated electrophoretically and stained, for example, with Coomassie blue.

Methods for the determination of levels of dystrophin and dystrophin-associated proteins are carried out by conventional techniques. Such techniques are disclosed, for example, in U.S. Pat. Nos. 5,187,063; 5,260,209; and 5,308,752, the disclosures of which are incorporated herein by reference. International Publication Number WO 89/06286 also discloses such conventional techniques, as well as the nucleic sequence encoding dystrophin.

Altered localization of the proteoglycan of the invention in a sample also can be determined. As used herein, the term "localization" refers to the pattern of deposition of the proteoglycan of the invention in a sample. The localization of the proteoglycan of the invention also can be determined qualitatively or quantitatively. "Altered" localization refers to a pattern of deposition of the proteoglycan of the invention in a sample that is different from the pattern of localization observed in a control sample.

The level of expression mRNA encoding the proteoglycan of the invention can be determined and can be used to identify an individual that is predisposed to a disorder, such as muscular, neuromuscular, or neurological disorder. Methods for determining the level of expression of proteoglycan mRNA in a sample are well known in the art and include, for example, northern blot analysis, which can be used to determine whether proteoglycan mRNA is expressed at a normal level in a test sample. Northern blot analysis also can be used to determine whether the proteoglycan mRNA that is expressed in a cell is a full length transcript. For example, an RNA sample obtained from a tissue sample can be contacted with a nucleic acid probe that hybridizes to the mRNA encoding the proteoglycan of the invention. One skilled in the art would know that the probe can be a DNA or RNA probe and can be prepared from a cDNA encoding the proteoglycan or can be synthesized as an oligonucleotide. In addition, the skilled artisan would recognize that such hybridization should be performed under stringent conditions, which can be determined empirically (see, for example, Sambrook et al., Molecular Cloning: A laboratory manual (Cold Spring Harbor Laboratory Press 1989), which is incorporated herein by reference). Methods for isolating intact total RNA and poly A+ mRNA and for performing Northern blot analysis are well known in the art (Sambrook et al., 1989).

A sensitive method of determining the level of expression of mRNA encoding the proteoglycan of the invention in a sample is the reverse transcriptase-polymerase chain reaction (RT-PCR), which is well known in the art (see, for example, H. A. Erlich, PCR Technology: Principles and applications for DNA amplification (Stockton Press, 1989), which is incorporated herein by reference; see chap. 8). The RT-PCR method is particularly useful for examining a sample that fails to give a detectable signal by northern blot analysis. Due to the amplification steps involved in PCR analysis, a rare proteoglycan mRNA can be identified in a sample.

Methods for determining levels of proteoglycan of the invention can use, e.g., antibodies binding to the proteoglycan of the invention. An antibody can be used in connection with a conventional assay for the determination of levels of antigen in a tissue of interest, e.g., muscle tissue. Any method which enables the determination of protein levels present in muscle tissue based on antibody binding is useful in connection with the present invention. Preferred methods include Western blotting, immunocytochemical analysis and enzyme-linked immunoadsorbent assay (ELISA).

For assays which require solubilized extracellular matrix (e.g., ELISA and Western blotting), the amount of muscle obtained by biopsy should be sufficient to enable the extraction of the proteoglycan of the invention in a quantity sufficient for analysis. In an illustrative embodiment, the muscle tissue is homogenized by mechanical disruption using an apparatus such as a hand operated or motor driven glass homogenizer, a Waring blade blender homogenizer, or an ultrasonic probe. Homogenization can be carried out, for example, in a buffer having a pH of about 11 or 12, as further described in the Examples. The buffer can further comprise protease inhibitors, e.g., 1 mM PMSF, 0.75 mM benzamidine, 1 μg/ml aprotinin, 1 μg/ml of leupeptin, 1 μg/ml of pepstatin A. The incubation is then carried out, e.g., on ice for 2 hr. Following centrifugation, extracellular matrix solubilized in this manner can then be processed by conventional methods for use, for example, in Western blotting or ELISA analytical formats.

The solubilized extracellular matrix components, prepared as described above can be analyzed by Western blotting by first separating the components on a 3-12% SDS polyacrylamide gel (Laemmli (1970) *Nature* 227, 680) followed by transfer to a solid support, such as a nitrocellulose membrane, forming an exact replica of the original protein separation but leaving the transferred proteins accessible for further study. This solid support bearing the transferred protein components is referred to as an immunoblot. The detection of transferred proteins can be accomplished by the use of general protein dyes such as Amido black or Coomassie brilliant blue. Antibodies which are specific for the proteoglycan of the invention can be labeled with a detectable reporter group and used to stain the protein transferred to the solid support. Alternatively, unlabeled antibodies specific for the proteoglycan of the invention are incubated with an immunoblot under conditions appropriate for binding. The specific binding of these antibodies to the muscle tissue sample can be detected through the use of labeled secondary antibodies by conventional techniques.

The methods of the present invention can also be practiced in an enzyme-linked immunoadsorbent assay (ELISA) format. In this format, antibodies against the proteoglycan of the invention are adsorbed to a solid support, in most cases a polystyrene microtiter plate. After coating the support with antibody and washing, a solubilized sample is added. Proteoglycan of the invention, if present, will bind to the adsorbed antibodies. Next, a conjugate that will also bind to the proteoglycan of interest is added. A conjugates can be an antibody molecule which binds to the proteoglycan of the invention, and to which an enzyme is covalently bound. After addition of a chromogenic substrate for the enzyme, the intensity of the colored reaction products generated will be proportional to the amount of conjugated enzyme and thus indirectly to the amount of bound proteoglycan of the invention. Since the intensity of the developed color is proportional to the amount of proteoglycan of the invention present, determination of the intensity of the color produced by a standard series of concentrations of proteoglycan of the invention will allow the calculation of the amount of proteoglycan of the invention in an unknown sample. Many variations of this assay exist as described in Voller, A., Bidwell, D. E. and Bartlett, A., The Enzyme Linked Immunoadsorbent Assay (ELISA): A guide with abstracts of microplate applications, Dynatech Laboratories, Alexandria, Va. (1979).

Alternatively, tissue specimens (e.g., human biopsy samples) can be tested for the presence of the components of the DAPC complex by using monoclonal or polyclonal antibodies in an immunohistochemical technique, such as the immunoperoxidase staining procedure. In addition, immunofluorescent techniques can be used to examine human tissue specimens. In a typical protocol, slides containing cryostat sections of frozen, unfixed tissue biopsy samples are air-dried and then incubated with an antibody preparation against the proteoglycan (primary antibody) of the invention in a humidified chamber at room temperature. The slides are layered with a preparation of fluorescently labeled antibody directed against the primary antibody. Labeled secondary antibodies are also useful for detection. The staining pattern and intensities within the sample can be determined by fluorescent light microscopy.

The invention also provides a prenatal diagnostic screening procedure using a tissue such as placenta or fetal muscle, wherein the screening procedure is useful for identifying an individual predisposed to a disorder, such as a muscular, neuromuscular, or neurological disorder.

In preferred embodiments, the methods for determining whether a subject has or is at risk for developing a disease, such as a muscular, neuromuscular, or neurological disease, is characterized as comprising detecting, in a tissue sample or in cells of the subject, the presence or absence of a genetic alteration characterized by at least one of (i) an alteration affecting the integrity of a gene encoding a proteoglycan of the invention, or (ii) the mis-expression of a gene encoding a proteoglycan of the invention. To illustrate, such genetic alterations can be detected by ascertaining the existence of at least one of (i) a deletion of one or more nucleotides from a gene encoding a proteoglycan of the invention, (ii) an addition of one or more nucleotides to a gene encoding a proteoglycan of the invention, (iii) a substitution of one or more nucleotides of a gene encoding a proteoglycan of the invention, (iv) a gross chromosomal rearrangement of a gene encoding a proteoglycan of the invention, (v) a gross alteration in the level of a messenger RNA transcript of a gene encoding a proteoglycan of the invention, (vii) aberrant modification of a gene encoding a proteoglycan of the invention, such as of the methylation pattern of the genomic DNA, (vii) the presence of a non-wild type splicing pattern of a messenger RNA transcript of a gene encoding a proteoglycan of the invention, (viii) a non-wild type level of proteoglycan of the invention, (ix) allelic loss of a gene encoding a proteoglycan of the invention, and/or (x) inappropriate post-translational modification of a proteoglycan of the invention, such as the presence of abnormal glycosamino glycan side chains. As set out below, the present invention provides a large number of assay techniques for detecting alterations in a gene encoding a proteoglycan of the invention. These methods include, but are not limited to, methods involving sequence analysis, Southern blot hybridization, restriction enzyme site mapping, and methods involving detection of absence of nucleotide pairing between the nucleic acid to be analyzed and a probe. These and other methods are further described infra.

Specific diseases or disorders, e.g., genetic diseases or disorders, are associated with specific allelic variants of polymorphic regions of certain genes, which do not necessarily encode a mutated protein. Thus, the presence of a specific allelic variant of a polymorphic region of a gene, such as a single nucleotide polymorphism ("SNP"), in a subject can render the subject susceptible to developing a specific disease or disorder. Polymorphic regions in genes, e.g., a gene encoding a proteoglycan of the invention, can be identified, by determining the nucleotide sequence of genes in populations of individuals. If a polymorphic region, e.g., SNP, is identified, then the link with a specific disease can be determined by studying specific populations of individuals, e.g., individuals which developed a specific disease, such a muscular, neuromuscular, or neurological disease. A polymorphic region can be located in any region of a gene, e.g., exons, in coding or non coding regions of exons, introns, and promoter region.

It is likely that genes encoding proteoglycans of the invention comprise polymorphic regions, specific alleles of which may be associated with specific diseases or conditions or with an increased likelihood of developing such diseases or conditions. Thus, the invention provides methods for determining the identity of the allele or allelic variant of a polymorphic region of a gene encoding a proteoglycan of the invention in a subject, to thereby determine whether the subject has or is at risk of developing a disease or disorder associated with a specific allelic variant of a polymorphic region.

In an exemplary embodiment, there is provided a nucleic acid composition comprising a nucleic acid probe including a region of nucleotide sequence which is capable of hybridizing to a sense or antisense sequence of a gene encoding a proteoglycan of the invention or naturally occurring mutants thereof, or 5' or 3' flanking sequences or intronic sequences naturally associated with the subject proteoglycan genes or naturally occurring mutants thereof. The nucleic acid of a cell is rendered accessible for hybridization, the probe is contacted with the nucleic acid of the sample, and the hybridization of the probe to the sample nucleic acid is detected. Such techniques can be used to detect alterations or allelic variants at either the genomic or mRNA level, including deletions, substitutions, etc., as well as to determine mRNA transcript levels.

A preferred detection method is allele specific hybridization using probes overlapping the mutation or polymorphic site and having about 5, 10, 20, 25, or 30 nucleotides around the mutation or polymorphic region. In a preferred embodiment of the invention, several probes capable of hybridizing specifically to allelic variants, such as single nucleotide polymorphisms, are attached to a solid phase support, e.g., a "chip". Oligonucleotides can be bound to a solid support by a variety of processes, including lithography. For example a chip can hold up to 250,000 oligonucleotides. Mutation detection analysis using these chips comprising oligonucleotides, also termed "DNA probe arrays" is described e.g., in Cronin et al. (1996) *Human Mutation* 7:244. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

In certain embodiments, detection of the alteration comprises utilizing the probe/primer in a polymerase chain reaction (PCR) (see, e.g. U.S. Pat. Nos. 4,683,195 and 4,683,202), such as anchor PCR or RACE PCR, or, alternatively, in a ligase chain reaction (LCR) (see, e.g., Landegran et al. (1988) *Science* 241:1077-1080; and Nakazawa et al. (1994) *PNAS* 91:360-364), the latter of which can be particularly useful for detecting point mutations in the gene (see Abravaya et al. (1995) *Nuc Acid Res* 23:675-682). In a merely illustrative embodiment, the method includes the steps of (i) collecting a tissue or cell sample from a patient, (ii) isolating nucleic acid (e.g., genomic, mRNA or both) from the cells of the sample, (iii) contacting the nucleic acid sample with one or more primers which specifically hybridize to the gene of interest (i.e., encoding the proteoglycan of interest) under conditions such that hybridization and amplification of the gene (if present) occurs, and (iv) detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., 1990, *Proc. Natl. Acad. Sci. USA* 87:1874-1878), transcriptional amplification system (Kwoh, D. Y. et al., 1989, *Proc. Natl. Acad. Sci. USA* 86:1173-1177), Q-Beta Replicase (Lizardi, P. M. et al., 1988, *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In yet another embodiment, any of a variety of sequencing reactions known in the art can be used to directly sequence a gene of interest and detect mutations by comparing the sequence of the sample gene with the corresponding wild-type (control) sequence. Exemplary sequencing reactions include those based on techniques developed by Maxam and Gilbert (*Proc. Natl Acad Sci USA* (1977) 74:560) or Sanger (Sanger et al (1977) *Proc. Nat. Acad. Sci.* 74:5463). It is also contemplated that any of a variety of automated sequencing procedures may be utilized when performing the subject assays (*Biotechniques* (1995) 19:448), including sequencing by mass spectrometry (see, for example PCT publication WO 94/16101; Cohen et al. (1996) *Adv Chromatogr* 36:127-162; and Griffin et al. (1993) *Appl Biochem Biotechnol* 38:147-159). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers, et al. (1985) *Science* 230:1242). In general, the art technique of "mismatch cleavage" starts by providing heteroduplexes formed by hybridizing (labelled) RNA or DNA containing the wild-type sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S I nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al (1988) *Proc. Natl. Acad Sci USA* 85:4397; Saleeba et al (1992) Methods Enzymol. 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a sequence encoding a proteoglycan of the invention, e.g., a wild-type sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations or the identity of the allelic variant of a polymorphic region in genes. For example, single strand conformation polymorphism (SSCP) may be used to detect differences in electrophoretic mobility between mutant and wild type nucleic acids (Orita et al. (1989) *Proc Natl. Acad. Sci. USA* 86:2766, see also Cotton (1993) *Mutat Res* 285:125-144; and Hayashi (1992) *Genet Anal Tech Appl* 9:73-79). Single-stranded DNA fragments of sample and control nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

Examples of other techniques for detecting point mutations or the identity of the allelic variant of a polymorphic region include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al. (1986) *Nature* 324:163); Saiki et al (1989) *Proc. Natl Acad. Sci USA* 86:6230). Such allele specific oligonucleotide hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Yet other techniques that can be used to detect a mutation of specific allele include the following: selective PCR amplification as described in Gibbs et al (1989) *Nucleic Acids Res.* 17:2437-2448, Prossner (1993) *Tibtech* 11:238, and Gasparini et al (1992) *Mol. Cell Probes* 6:1; oligonucleotide ligation assay (OLA), as described, e.g., in U.S. Pat. No. 4,998,617 and in Landegren, U. et al., Science 241:1077-1080 (1988), U.S. Pat. No. 5,593,826, Tobe et al. (1996) Nucleic Acids Res 24: 3728. Other techniques can be used for detecting a single nucleotide polymorphism. Examples of such techniques are disclosed, e.g., in Mundy, C. R. U.S. Pat. No. 4,656,127; Cohen, D. et al. (French Patent 2,650,840; PCT Appln. No. WO91/02087); Genetic Bit Analysis or GBA™, described by Goelet, P. et al. (PCT Appln. No. 92/15712). Komher, J. S. et al., *Nucl. Acids. Res.* 17:7779-7784 (1989); Sokolov, B. P., *Nucl. Acids Res.* 18:3671 (1990); Syvanen, A.-C., et al., *Genomics* 8:684-692 (1990); Kuppuswamy, M. N. et al., *Proc. Natl. Acad. Sci.* (U.S.A.) 88:1143-1147 (1991); Prezant; T. R. et al., *Hum. Mutat.* 1:159-164 (1992); Ugozzoli, L. et al., *GATA* 9:107-112 (1992); Nyren, P. et al., *Anal. Biochem.* 208:171-175 (1993)).

For mutations that produce premature termination of protein translation, the protein truncation test (PTT) offers an efficient diagnostic approach (Roest, et. al., (1993) *Hum. Mol. Genet.* 2:1719-21; van der Luijt, et. al., (1994) *Genomics* 20:1-4).

The methods described herein may be performed, for example, by utilizing pre-packaged diagnostic kits comprising at least one probe nucleic acid, primer set; and/or antibody reagent described herein, which may be conveniently used, e.g., in clinical settings to diagnose patients exhibiting symptoms or family history of a disease or illness involving a proteoglycan of the invention (see below).

Any cell type or tissue may be utilized in the diagnostics described below. In a preferred embodiment a bodily fluid, e.g., blood, is obtained from the subject to determine the presence of a mutation or the identity of the allelic variant of a polymorphic region of a gene encoding a proteoglycan of interest. A bodily fluid, e.g., blood, can be obtained by known techniques (e.g. venipuncture). Alternatively, nucleic acid tests can be performed on dry samples (e.g. hair or skin). For prenatal diagnosis, fetal nucleic acid samples can be obtained from maternal blood as described in International Patent Application No. WO91/07660 to Bianchi. Alternatively, amniocytes or chorionic villi may be obtained for performing prenatal testing.

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, G. J., 1992, PCR in situ Hybridization: Protocols and Applications, Raven Press, NY).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Antibodies directed against wild type or mutant proteoglycans of the invention or allelic variant thereof, which are discussed above, may also be used in disease diagnostics and prognostics. Such diagnostic methods may be used to detect abnormalities in the level of the expression of the proteoglycan of the invention, or abnormalities in the structure and/or tissue, cellular, or subcellular location of the proteoglycan. Structural differences may include, for example, differences in the size, electronegativity, or antigenicity of the mutant proteoglycan of the invention relative to the normal proteoglycan. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook et al, 1989, supra, at Chapter 18. The protein detection and isolation methods employed herein may also be such as those described in Harlow and Lane, for example, (Harlow, E. and Lane, D., 1988, "Antibodies: A Laboratory Manual", Cold Spring Harbor Laboratory Press, Cold Spring Harbor, N.Y.), which is incorporated herein by reference in its entirety.

This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of proteoglycans. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of a proteoglycan of the invention, but also its distribution in the examined tissue. Using the present invention, one of ordinary skill will readily perceive that any of a wide variety of histological methods (such as staining procedures) can be modified in order to achieve such in situ detection.

Often a solid phase support or carrier is used as a support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

One means for labeling an antibody that specifically binds to a proteoglycan of the invention is via linkage to an enzyme and use in an enzyme immunoassay (EIA) (Voller, "The Enzyme Linked Immunosorbent Assay (ELISA)", *Diagnostic Horizons* 2:1-7, 1978, Microbiological Associates Quarterly Publication, Walkersville, Md.; Voller, et al., J. Clin. Pathol. 31:507-520 (1978); Butler, Meth. Enzymol. 73:482-523 (1981); Maggio, (ed.) *Enzyme Immunoassay*, CRC Press, Boca Raton, Fla., 1980; Ishikawa, et al., (eds.) *Enzyme Immunoassay*, Kgaku Shoin, Tokyo, 1981). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Moreover, it will be understood that any of the above methods for detecting alterations in a gene or gene product or polymorphic variants can be used to monitor the course of treatment or therapy.

Screening Methods

The invention further provides methods for identifying agents which modulate membrane integrity, in particular, by modulating DAPC stability, and agents which modulate neuromuscular junction formation, such as by modulating postsynaptic differentiation. Thus, the invention provides methods for identifying agents which modulate the activity of a proteoglycan of the invention, e.g., DAG-125, or proteoglycan having similar activity. The agent can be an agonist of a biological activity of a proteoglycan of the invention, or the agent can be an antagonist of a proteoglycan of the invention. An agonist agent will be of interest for use in prophylactic and therapeutic treatments of diseases or disorders, e.g., characterized by an instable DAPC or an inappropriate formation of a postsynaptic differentiation. An antagonist agent will be of interest for use in prophylactic and therapeutic treatments of diseases or disorders, e.g., characterized by an overactive neuromuscular junction, e.g., in situations in which there is an excess of the proteoglycan of the invention.

Accordingly, the invention provides screening methods for identifying therapeutics. A therapeutic of the invention can be any type of compound, including a protein, a peptide, a proteoglycan, a polysaccharide, a peptidomimetic, a small molecule, and a nucleic acid. A nucleic acid can be, e.g., a gene, an antisense nucleic acid, a ribozyme, or a triplex molecule.

Preferred agonists include compounds, such as proteoglycans, which mimic at least one biological activity of a proteoglycan of the invention, e.g., the capability to bind to one or more components of a DAPC, such as alpha-dystroglycan, or the capability to stimulate MuSK phosphorylation and/or AChR aggregation. Other preferred agonists include compounds which are capable of increasing the production of the proteoglycan of the invention in a cell, e.g., compounds capable of upregulating the expression of the gene encoding the proteoglycan, and compounds which are capable of enhancing an activity of a proteoglycan of the invention, and/or the interaction of a proteoglycan of the invention with another molecule, such as a component of a DAPC or MuSK.

Preferred antagonists include compounds which are dominant negative proteins, which, e.g., are capable of binding to alpha-sarcoglycan, but not to stabilize DAPCs, such as by competing with the endogenous proteoglycan of the invention. Other preferred antagonists include compounds which decrease or inhibit the production of a proteoglycan of the invention in a cell and compounds which are capable of downregulating expression of a gene encoding a proteoglycan of the invention, and compounds which are capable of downregulating an activity of a proteoglycan of the invention and/or its interaction with another molecule, such as alpha-sarcoglycan. In another preferred embodiment, an antagonist is a modified form of an alpha-dystroglycan or other molecule capable of binding to the wild type proteoglycan of the invention, which is capable of interacting with the proteoglycan of the invention, but which does not have biological activity, e.g., which does not stabilize DAPCs.

The invention also provides screening methods for identifying therapeutics which are capable of binding to a proteoglycan of the invention, e.g., a wild-type proteoglycan of the invention or a mutated form thereof, and thereby modulate the a biological activity of a proteoglycan of the invention, or degrades, or causes the proteoglycan of the invention to be degraded. For example, such a therapeutic can be an antibody or derivative thereof which interacts specifically with a proteoglycan of the invention (either wild-type or mutated).

Thus, the invention provides screening methods for identifying agonist and antagonist compounds, comprising selecting compounds which are capable of interacting with a proteoglycan of the invention or with a molecule interacting with a proteoglycan of the invention, such a component of a DAPC or MuSK, and/or compounds which are capable of modulating the interaction of an a proteoglycan of the invention with another molecule, such as a component of a DAPC or MuSK. In general, a molecule which is capable of interacting with a proteoglycan of the invention is referred to herein as "proteoglycan binding partner" or "PT-binding partner" and can be a component of a DAPC, e.g., a dystroglycan or a sarcoglycan, or MuSK.

The compounds of the invention can be identified using various assays depending on the type of compound and activity of the compound that is desired. Set forth below are at least some assays that can be used for identifying therapeutics of the invention. It is within the skill of the art to design additional assays for identifying therapeutics.

Cell-Free Assays

Cell-free assays can be used to identify compounds which are capable of interacting with a proteoglycan of the invention or binding partner thereof, to thereby modify the activity of the proteoglycan of the invention or binding partner thereof. Such a compound can, e.g., modify the structure of a proteoglycan of the invention or binding partner thereof and thereby affect its activity. Cell-free assays can also be used to identify compounds which modulate the interaction between a proteoglycan of the invention and a PT-binding partner, such as a component of a DAPC. In a preferred embodiment, cell-free assays for identifying such compounds consist essentially in a reaction mixture containing a proteoglycan of the invention, and a test compound or a library of test compounds with or without a binding partner. A test compound can be, e.g., a derivative of a PT-binding partner, e.g., a biologically inactive target peptide, or a small molecule.

These assays can be performed with a complete proteoglycan molecule of the invention. Alternatively, the screening assays can be performed with portions thereof, such as the core only, one or more LLR domains, the glycosamino glycan chains only, or portions thereof, or combinations of these portions. These can be prepared as set forth supra.

Accordingly, one exemplary screening assay of the present invention includes the steps of contacting a proteoglycan of the invention or functional fragment thereof or a PT-binding partner with a test compound or library of test compounds and detecting the formation of complexes. For detection purposes, the molecule can be labeled with a specific marker and the test compound or library of test compounds labeled with a different marker. Interaction of a test compound with a proteoglycan of the invention or fragment thereof or PT-binding partner can then be detected by determining the level of the two labels after an incubation step and a washing step. The presence of two labels after the washing step is indicative of an interaction.

An interaction between molecules can also be identified by using real-time BIA (Biomolecular Interaction Analysis, Pharmacia Biosensor AB) which detects surface plasmon resonance (SPR), an optical phenomenon. Detection depends on changes in the mass concentration of macromolecules at the biospecific interface, and does not require any labeling of interactants. In one embodiment, a library of test compounds can be immobilized on a sensor surface, e.g., which forms one wall of a micro-flow cell. A solution containing the proteoglycan of the invention, functional fragment thereof, analog or PT-binding partner is then flown continuously over the sensor surface. A change in the resonance angle as shown on a signal recording, indicates that an interaction has occurred. This technique is further described, e.g., in BIAtechnology Handbook by Pharmacia.

Another exemplary screening assay of the present invention includes the steps of (a) forming a reaction mixture including: (i) a proteoglycan of the invention, (ii) a PT-binding partner (e.g., alpha-sarcoglycan), and (iii) a test compound; and (b) detecting interaction of the proteoglycan of the invention and the PT-binding protein. The proteoglycan of the invention and PT-binding partner can be produced recombinantly, purified from a source, e.g., plasma, or chemically synthesized, as described herein. A statistically significant change (potentiation or inhibition) in the interaction of the proteoglycan of the invention and PT-binding protein in the presence of the test compound, relative to the interaction in the absence of the test compound, indicates a potential agonist (mimetic or potentiator) or antagonist (inhibitor) of a bioactivity for the test compound. The compounds of this assay can be contacted simultaneously. Alternatively, a proteoglycan of the invention can first be contacted with a test compound for an appropriate amount of time, following which the PT-binding partner is added to the reaction mixture. The efficacy of the compound can be assessed by generating dose response curves from data obtained using various concentrations of the test compound. Moreover, a control assay can also be performed to provide a baseline for comparison. In the control assay, isolated and purified proteoglycan of the invention or binding partner is added to a composition containing the PT-binding partner or proteoglycan of the invention, and the formation of a complex is quantitated in the absence of the test compound.

Complex formation between a proteoglycan of the invention and a PT-binding partner may be detected by a variety of techniques. Modulation of the formation of complexes can be quantitated using, for example, detectably labeled proteins such as radiolabeled, fluorescently labeled, or enzymatically labeled proteoglycans of the invention or PT-binding partners, by immunoassay, or by chromatographic detection.

Typically, it will be desirable to immobilize either the proteoglycan of the invention or its binding partner to facilitate separation of complexes from uncomplexed forms of one or both of the proteins, as well as to accommodate automation of the assay. Binding of a proteoglycan of the invention to a PT-binding partner, can be accomplished in any vessel suitable for containing the reactants. Examples include microtitre plates, test tubes, and micro-centrifuge tubes. In one embodiment, a fusion protein can be provided which adds a domain that allows the protein to be bound to a matrix. For example, glutathione-S-transferase/ACE-2 (GST/proteoglycan of the invention) fusion proteins can be adsorbed onto glutathione sepharose beads (Sigma Chemical, St. Louis, Mo.) or glutathione derivatized microtitre plates, which are then combined with the PT-inding partner, e.g. an $^{35}S$-labeled PT-binding partner, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of proteoglycan of the invention or PT-binding partner found in the bead fraction is quantitated from the gel using standard electrophoretic techniques such as described in the appended examples.

Other techniques for immobilizing proteins on matrices are also available for use in the subject assay. For instance, either the proteoglycan of the invention or its cognate binding partner can be immobilized utilizing conjugation of biotin and streptavidin. For instance, biotinylated proteoglycan molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with the proteoglycan of the invention can be derivatized to the wells of the plate, and the proteoglycan of the invention trapped in the wells by antibody conjugation. As above, preparations of a PT-binding protein and a test compound are incubated in the proteoglycan presenting wells of the plate, and the amount of complex trapped in the well can be quantitated. Exemplary methods for detecting such complexes, in addition to those described above for the GST-immobilized complexes, include immunodetection of complexes using antibodies reactive with the PT-binding partner, or which are reactive with protein and compete with the binding partner; as well as enzyme-linked assays which rely on detecting an enzymatic activity associated with the binding partner, either intrinsic or extrinsic activity. In the instance of the latter, the enzyme can be chemically conjugated or provided as a fusion protein with the PT-binding partner. To illustrate, the PT-binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al (1974) *J Biol Chem* 249:7130).

For processes which rely on immunodetection for quantitating one of the proteins trapped in the complex, antibodies against the proteoglycan of the invention can be used. Alternatively, the protein to be detected in the complex can be "epitope tagged" in the form of a fusion protein which includes, in addition to the sequence of the core of the proteoglycan of the invention, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150-21157) which includes a 10-residue sequence from c-myc, as well as the pFLAG system (International Biotechnologies, Inc.) or the pEZZ-protein A system (Pharmacia, N.J.).

Cell-free assays can also be used to identify compounds which interact with a proteoglycan of the invention and modulate an activity of a proteoglycan of the invention. Accordingly, in one embodiment, a proteoglycan of the invention is contacted with a test compound and the catalytic activity of the proteoglycan of the invention is monitored. In one embodiment, the ability of the proteoglycan of the invention to bind to a binding partner is determined. The binding affinity of a proteoglycan of the invention to a binding partner can be determined according to methods known in the art.

Cell Based Assays

Cell based assays can be used, in particular, to identify compounds which modulate expression of a gene encoding a proteoglycan of the invention, modulate translation of the mRNA encoding a proteoglycan of the invention, modulate the posttranslational modification of the core protein of the proteoglycan, or which modulate the stability of the mRNA or protein. Accordingly, in one embodiment, a cell which is capable of producing a proteoglycan of the invention, e.g., a muscle cell, is incubated with a test compound and the amount of proteoglycan of the invention produced in the cell medium is measured and compared to that produced from a cell which has not been contacted with the test compound. The specificity of the compound vis a vis the proteoglycan of the invention can be confirmed by various control analysis, e.g., measuring the expression of one or more control genes.

Cell based assays can also rely on a reporter gene system detecting whether two molecules interact or not, e.g., the classic two hybrid system, that can be conducted in yeast or in mammalian cells.

Compounds which can be tested include small molecules, proteins, and nucleic acids. In particular, this assay can be used to determine the efficacity of antisense molecules or ribozymes that bind to RNA encoding the proteoglycan of the invention.

In another embodiment, the effect of a test compound on transcription of a gene encoding a proteoglycan is determined by transfection experiments using a reporter gene operatively linked to at least a portion of the promoter of a gene encoding a proteoglycan of the invention. A promoter region of a gene can be isolated, e.g., from a genomic library according to methods known in the art. Promoters of genes encoding proteoglycans, e.g., biglycan, are publically available, e.g., from GenBank. The reporter gene can be any gene encoding a protein which is readily quantifiable, e.g., the luciferase or CAT gene, well known in the art.

This invention further pertains to novel agents identified by the above-described screening assays and uses thereof for treatments as described herein.

Assays for Identifying Compounds which Modulate Phosphorylation

Biglycan was shown to phosphorylate alpha-sarcoglycan and MuSK. Accordingly, compounds which stimulate phosphorylation of these compounds may exercise at least part of the activity of biglycan in stabilizing muscle cell membranes or of potentiating postsynaptic membranes. Thus, also within the scope of the invention are methods for identifying such compounds. In one embodiment, the method comprises contacting a cell, e.g., a muscle cell, with a compound, and monitoring the level of phosphorylation of a DAPC component, such as alpha-sarcoglycan, or MuSK, wherein a higher level of phosphorylation relative to that in an untreated cell indicates that the compound stimulates phosphorylation. Such assays can also be conducted in vitro using cell extracts or purified proteins. For example, the method may comprise contacting a purified sarcoglycan or MuSK and a cell extract from biglycan-activated cells (i.e., cells contacted with biglycan) or a kinase in the presence of a test compound, and monitoring whether the presence of the test compound prevents or stimulates phosphorylation.

Additional Exemplary Uses for the Proteoglycans of the Invention

The proteoglycans, or the core thereof, of the invention, can also be used as a supplement to a cell or tissue culture (e.g., system for growing organs). Any cell type may benefit from these supplements. The amount of compound to be added to the cultures can be determined in small scale experiments, by, e.g., incubating the cells or organs with increasing amounts of a specific compound of the invention. Preferred cells include eukaryotic cells, e.g., muscle cells or neuronal cells.

Other preferred tissues include atrophic tissue. Thus, such tissue can be incubated in vitro with an effective amount of a compound of the invention to reverse tissue atrophy. In one embodiment, atrophic tissue is obtained from as subject, the tissue is cultured ex vivo with a compound of the invention in an amount and for a time sufficient to reverse the tissue atrophy, and the tissue can then be readministered to the same or a different subject.

Alternatively, the compounds of the invention can be added to in vitro cultures of cells or tissue obtained from a subject having a muscular dystrophy, or other disease that can be treated with a compound of the invention, to improve their growth or survival in vitro. The ability to maintain cells, such as brain cells or muscle cells from subjects having a muscular dystrophy or other disease, is useful, for, e.g., developing therapeutics for treating the disease.

Kits of the Invention

The invention provides kits for diagnostic tests or therapeutic purposes.

The materials for performing the diagnostic assays of the present invention can be made available in a kit and sold, for example, to hospitals, clinics and doctors. A kit for detecting altered expression and/or localization of the proteoglycan of the invention, for example, can contain a reagent such as antibody binding to the proteoglycan of the invention, and, if desired, a labeled second antibody, a suitable solution such as a buffer for performing, for example, an immunohistochemical reaction and a known control sample for comparison to the test sample.

A kit for detecting altered expression of mRNA encoding the proteoglycan of the invention in a sample obtained from an individual, e.g., an individual suspected of being predisposed to a disorder, e.g., a muscular, neuromuscular, or neurological disorder, also can be prepared. Such a kit can contain, for example one or more of the following reagents: a reagent such as an oligonucleotide probe that hybridizes to mRNA encoding the proteoglycan of the invention, suitable solutions for extracting mRNA from a tissue sample or for performing the hybridization reaction and a control mRNA sample for comparison to the test sample, and a series of control mRNA samples useful, for example, for constructing a standard curve.

Such diagnostic assay kits are particularly useful because the kits can contain a predetermined amount of a reagent that can be contacted with a test sample under standardized conditions to obtain an optimal level of specific binding of the reagent to the sample. The availability of standardized methods for identifying an individual predisposed to a disorder, e.g., muscular dystrophy will allow for greater accuracy and precision of the diagnostic methods.

Kits for therapeutic or preventive purposes can include a therapeutic and optionally a method for administering the therapeutic or buffer necessary for solubilizing the therapeutic.

The present invention is further illustrated by the following examples which should not be construed as limiting in any way. The contents of all cited references (including literature references, issued patents, published patent applications as cited throughout this application are hereby expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $2^{nd}$ Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

EXAMPLES

Example 1

Characterization of a Dystroglycan-Binding Protein, DAG-125

This Example describes the identification of a dystroglycan-binding protein, termed DAG-125.

In order to identify novel dystroglycan binding partners, a ligand blot overlay assay, was developed as follows. Postsynaptic and non-synaptic membrane fractions from Torpedo electric organ were prepared as previously described (Bowe, et al. (1994) *Neuron.* 12: 1173). All handling of membranes and protein was performed at 4° C.

Membrane proteins were separated by SDS-PAGE (5-15% gradient gel), and transferred to nitrocellulose. To detect dystroglycan binding proteins, the nitrocellulose was rinsed and blocked for 3 hr in Hank's Balanced Salt Solution containing 1 mM $CaCl_2$, 1 mM $MgCl_2$, 1% bovine serum albumin, 1% Nonfat Dry Milk, 1 mM DTT, 10 mM HEPES, pH 7.4, and was then incubated overnight in the same buffer containing $^{35}$S-methionine-labelled dystroglycan fragments produced by in vitro transcription/translation as follows.

DNA fragments encoding $DG_{1-891}$ and $DG_{345-891}$ (human alpha-dystroglycan sequence is described, e.g., in Ibraghimov-BeskrovnayaHum (1993) *Mol Genet* 2: 1651) were cloned in the in vitro expression vector pMGT developed by A. Ahn (Ahn and Kunkel (1995) *J Cell Biol.* 128: 363). Additional in vitro expression plasmids used in this study (including $DG_{1-750}$, $DG_{776-891}$, and $DG_{345-653}$) were prepared by PCR-based subcloning of these inserts. The PCR primers included restriction sites for religation into the EcoRI site of pMGT. Dystroglycan protein fragments were generated by in vitro transcription/translation using the Promega TNT T7 coupled reticulocyte system as per the manufacturer's instructions. For protein to be used in ligand blot overlay assay, the reaction mixture contained $^{35}$S-methionine (with no unlabeled methionine). After incubation for 2 hr, the reaction mixture was passed over Bio-Spin desalting columns (Bio-Rad, Hercules, Calif.) to remove unincorporated amino acids and salts.

After incubation of the blots with the in vitro translated proteins, the blots were rinsed and dried and bound dystroglycan fragments were visualized by autoradiography. To detect dystroglycan present in the SDS-PAGE sample, an agrin blot overlay assay was performed essentially as described in O'Toole, et al. (1996) *PNAS* 93:7369. Briefly, the nitrocellulose was rinsed and blocked for 3 hr in HEPES-buffered Minimum Essential Medium supplemented with 1% bovine serum albumin and 10% horse serum. It was then incubated for 4 hr in this buffer containing recombinant rat agrin (isoform $A_0B_0$, prepared as described in O'Toole et al., supra), followed by a second layer containing 1 μg/ml anti-agrin antibody $^{125}$I-Mab-131 (Stressgen Laboratories, Victoria, BC). Bound anti-agrin antibody was visualized by autoradiography.

Figure 2:
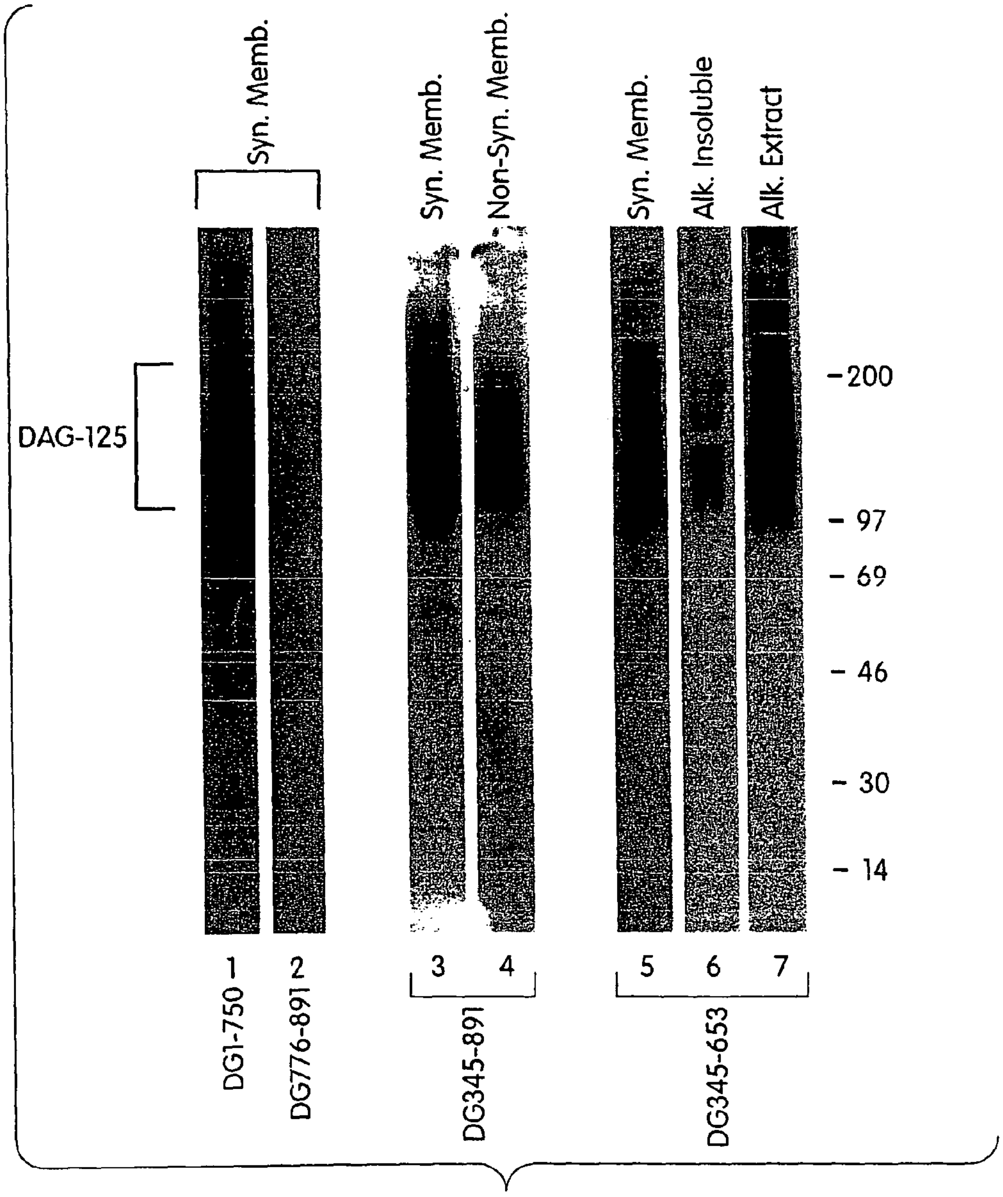
FIG. 2 shows the results of a ligand blot overlay assay, in which filters with various extracts (as indicated) were incubated with portions of alpha-dystroglycan.

The results are shown in FIG. 2. Lanes 1 and 2 indicate that certain fragments of dystroglycan bound to an about 125 kD, highly glycosylated polypeptide, which was termed DAG-125 (for "Dystroglycan-Associated Glycoprotein, 125 kDa"). As shown in FIG. 2A, the extracellular domain of dystroglycan (lane 1: $DG_{1-750}$) bound to DAG-125, while the intracellular portion of dystroglycan (lane 2: $DG_{776-891}$) did not.

Lanes 3 and 4 of FIG. 2 show that DAG-125 is enriched in synaptic as compared to non-synaptic membranes.

To solubilize DAG-125, synaptic membranes were centrifuged at 100,000×g for 1 hour (hr) and resuspended in $ddH_2O$. The pH was adjusted to 11.0 or 12.0 (as indicated) with NaOH and the membranes stirred for 1 hr. Insoluble material was removed by centrifugation at 100,000×g for 1 hr. The alkaline extract was neutralized with 10 mM Tris HCl and adjusted to pH 7.4. DAG-125 remained soluble under these conditions as determined by resistance to pelleting during a second centrifugation. Lanes 5-7 of FIG. 2 show that DAG-125 is a peripheral membrane protein that can be extracted from the synaptic membrane by alkaline treatment. Synaptic membranes were extracted at pH 12 and the insoluble (lane 6) and soluble fraction (lane 7) were analyzed. Greater than 90% of DAG-125 is solubilized by pH 12.0 treatment. Thus, DAG-125 is likely to be a peripheral membrane protein, since it is removed from the membranes by alkaline-treatment.

Example 2

Association Between α-Dystroglycan and DAG-125

This Example demonstrates that DAG-125 associates with in vitro-translated α-dystroglycan, bacterially produced GST-α-dystroglycan fusion protein and native α-dystroglycan in solution.

DAG-125 was solubilized by alkaline-treatment, and neutralized, as described above, and incubated with column matrices and recombinant or native dystroglycan as indicated in FIG. 3. The input material and eluates from the beads were analyzed by ligand blot overlay assay for the presence of DAG-125 ($^{35}$S-DG345-653 as probe) or native α-dystroglycan (agrin overlay, see Example 1).

Figure 3A:
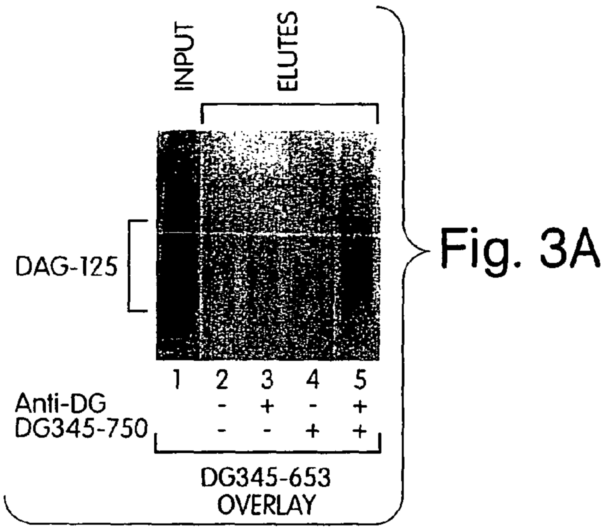
FIG. 3 (A-C) shows the results of a blot overlay assays in which filters with input and elutes from columns were incubated with portions of alpha dystroglycan or agrin.

FIG. 3A shows DAG-125 incubated with goat anti-mouse Ig-conjugated agarose beads in the presence or absence of in vitro translated dystroglycan polypeptide ($DG_{345-750}$) and/or anti-dystroglycan monoclonal antibody (NCL-β-DG; Novocastra, Newcastle-on-Tyne, UK). The results indicate that DAG-125 co-precipitated with dystroglycan plus anti-dystroglycan antibody (lane 5), but was not precipitated in the absence of either or both (lanes 2-4). Thus, DAG-125 binds to in vitro translated dystroglycan peptide DG345-750.

Figure 3B:
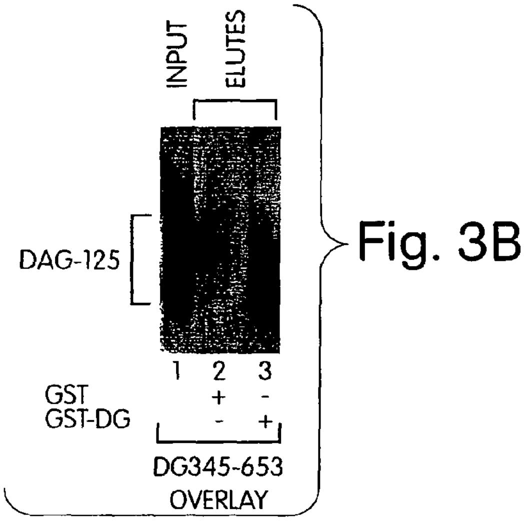

FIG. 3B shows DAG-125 incubated with glutathione-Sepharose beads that had been pre-incubated with either bacterially produced GST or a bacterially produced GST-dystroglycan fusion protein (GST-$DG_{345-653}$). A fusion protein of glutathione S-transferase (GST) and amino acids 345-653 of dystroglycan was produced by using PCR-based subcloning to introduce dystroglycan coding sequence into the bacterial protein expression vector pGEX-1 T (Pharmacia, Piscataway, N.J.). The resulting bacterial expression plasmid, pGST-$DG_{345-653}$, was then introduced into the *E. coli* strain BL21 and expressed fusion protein recovered from the cytoplasmic fraction as per manufacturer's instructions. Control protein (GST) was obtained using pGEX-1 T. The results show that DAG-125 was co-precipitated with the dystroglycan fusion protein (lane 3), but not with GST alone (lane 2). Thus, DAG-125 binds to alpha-dystroglycan peptide 345-653 produced in bacteria.

Figure 3C:
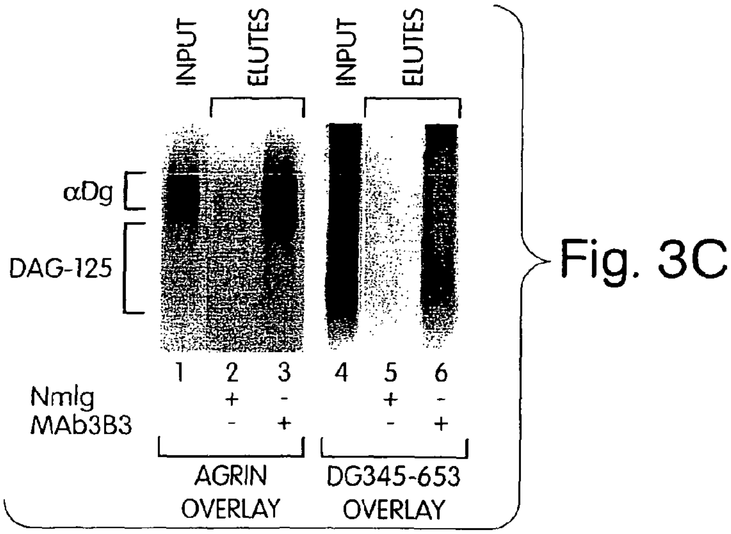

FIG. 3C shows DAG-125 and native α-dystroglycan. Alkaline extracts of Torpedo electric organ membranes contain both DAG-125 and α-dystroglycan. This extract was applied to agarose columns conjugated to either control antibody or to an anti-Torpedo dystroglycan monoclonal antibody (MAb3B3; Bowe, M. A., et al. (1994) *Neuron.* 12: 1173). The results show that native α-dystroglycan and DAG-125 were co-precipitated by the anti-Torpedo dystroglycan antibody, Mab3B3, (lanes 3 and 6), but not by control antibody (lanes 2 and 5). Western blots indicate that Mab3B3 does not recognize DAG-125 (see Bowe, M. A., et al., 1994, *Neuron.* 12: 1173-1180).

Thus, FIG. 3 shows that DAG-125 co-precipitates with in vitro-translated alpha-dystroglycan, bacterially produced GST-alpha-dystroglycan protein, and with native alpha-dystroglycan.

Example 3

Localization of the DAG-125 Binding Domain of α-Dystroglycan

This Example describes that the DAG-125 binding domain of α-dystroglycan is contained in an approximately 150 amino acid carboxyl-terminal domain of the protein.

Figure 4:
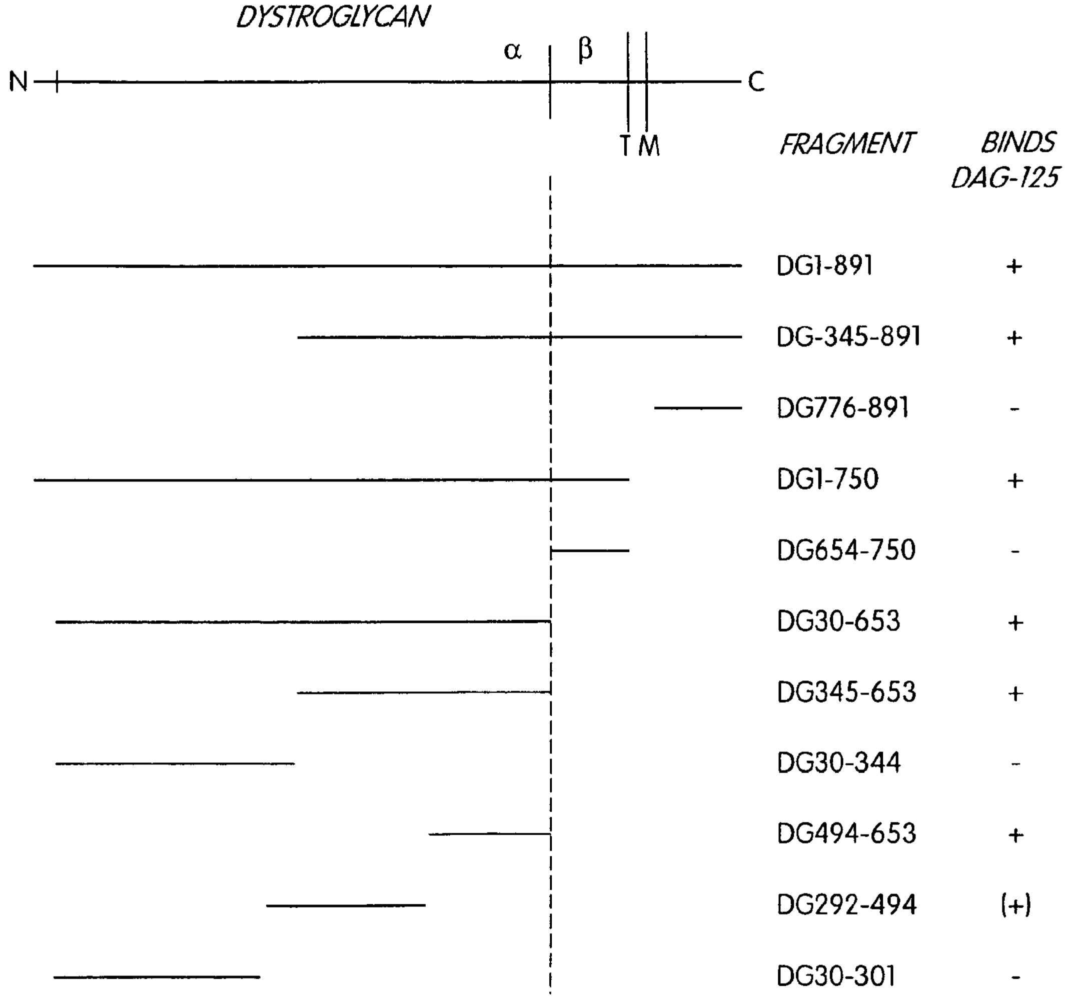
FIG. 4 is a diagram showing portions of dystroglycan used in a blot overlay assays and the presence (+) or absence (−) of binding.

In order to determine the region of α-dystroglycan that interacts with DAG-125, a panel of dystroglycan fragments were prepared by in vitro translation (FIG. 4) and the ability of each to bind DAG-125 was tested using the ligand blot overlay assay. FIG. 4, which shows the results, indicates that DAG-125 binds to the carboxyl-terminal one-third of α-dystroglycan. A small contribution from the middle third of α-dystroglycan is also possible. The ectodomain of β-dystroglycan does not appear to contribute to binding of DAG-125. Moreover, these fragments were produced under conditions in which the polypeptides are not glycosylated. Therefore, carbohydrate side chains on dystroglycan are not necessary for its binding to DAG-125.

Thus, the major binding domain is contained in about 150 amino acid region of dystroglycan. The location of this domain and the lack of a carbohydrate requirement indicate that α-dystroglycan's binding site for biglycan is distinct from that mediating association with agrin, laminin, and perlecan.

Example 4

Identification of DAG-125 as Biglycan or a Proteoglycan Related Thereto

This Example demonstrates that DAG-125 is biglycan or a protein related thereto.

It was found that DAG-125 co-purified with postsynaptic membranes, but that, however, it was insoluble in all non-ionic detergents tested including Triton X-100 and n-octyl-β-D-glucopyranoside, both of which efficiently extract α/β- dystroglycan from these membranes (Bowe, et al. (1994) *Neuron.* 12: 1173; Deyst, et al. (1995) *J Biol Chem.* 270: 25956-9). Even without detergent, about 50% of DAG-125 could be extracted at pH 11 and near-complete solubilization was achieved by a short pH 12 treatment (see FIG. 2A). Importantly, DAG-125 remained soluble when returned to neutral pH. Based upon these properties and the findings that DAG-125 binds to both heparin and chondroitin sulfate columns, the following purification protocol was developed.

Postsynaptic-rich membrane fractions were first pre-extracted with 25 mM n-octyl-1-D-glucopyranoside to remove detergent-soluble proteins. DAG-125 was then solubilized by alkaline extraction (pH 12.0), as described in Example 1. The alkaline extract was diluted in SEN Buffer (20 mM Tris HCl, 100 mM NaCl, 23 μg/ml aprotinin, 0.5 μg/ml leupeptin, 5 mM benzamidine, 0.7 μg/ml pepstatin A, 1 mM phenylmethylsulfonylflouride, 0.02% azide, 0.1% Tween 20, pH 7.6) and recentrifuged to remove any proteins precipitating upon neutralization. The extract remained in SEN Buffer for the remainder of the purification, with only the NaCl concentration changed as indicated. The extract was passed over a MAb3B3 column (Bowe, et al. (1994) *Neuron.* 12: 1173) to remove α-dystroglycan. The MAb3B3 column flow-through was passed over a combined, non-DAG-125-binding lectin-agarose column (peanut agglutinin and *ulex europaeus* agglutinin I, Vector Labs, Burlingame, Calif.) as a second pre-clear. The flow-through was next applied to a column of chondroitin sulfate-agarose (CS-agarose). The CS-agarose column was prepared by coupling chondroitin sulfate B (Sigma, St. Louis, Mo.; #C-3788) to -aminohexyl-agarose (Sigma) activated with N-ethyl-N'-(3-dimethylaminopropyl)-carbodiimide (Sigma). After incubation with the lectin column flow-through, the CS column was washed extensively and eluted with a 0.1-2.0 M NaCl gradient. DAG-125 eluted in 0.3-0.65 M NaCl. These fractions were pooled, diluted to 0.3 M NaCl, and applied to a heparin-agarose column (Sigma #H-0402). The column was washed and eluted with a 0.3-2 M NaCl gradient. DAG-125 eluted in 0.6-0.85 M NaCl. These fractions were pooled, concentrated by ethanol precipitation (final purity of DAG-125 of about 30%), redissolved in SDS-PAGE sample buffer, separated on a 5-15% gradient gel, and transferred to a PVDF membrane. A portion of the PVDF membrane was analyzed for DAG-125 by blot overlay and the remainder was transiently stained with Ponceau S. Two regions (“U” and “L”; see FIG. 5A) of the DAG-125 band on the Ponceau stained membrane were excised and digested with trypsin. The released peptides were analyzed by HPLC using a C8 column and UV detection. The column profiles were virtually identical, indicating that the polydisperse band is due to the presence of a single, heterogeneously glycosylated protein.

Three peptides from the trypsin digest were collected as fractions from the HPLC analysis and subjected to automated Edman degradation, as described previously (Bowe, et al. (1994) *Neuron.* 12: 1173). The sequences obtained were compared to public databases. The alignment of the Torpedo DAG-125 peptides to the deduced sequence of human biglycan (amino acids 241-249; 258-266; and 330-348) is shown in FIG. 5B. Human biglycan is described in Fisher et al. (1989), infra) and its amino acid sequence is set fort in SEQ ID NO: 9. All DAG-125 peptide fragments were highly homologous to mammalian biglycan, with an overall 76% identity (FIG. 5B). Thus, DAG-125 is a Torpedo orthologue of mammalian biglycan or a close homolog thereof.

Human biglycan, produced in the vaccinia system, as described below, was also shown to bind to alpha-dystroglycan. The binding was less strong than with Torpedo DAG-125, probably reflecting the fact that the biglycan produced in this system is a mixture of core biglycan and proteoglycan biglycan. However, this further supports that Torpedo orthologue of mammalian biglycan or a close homolog thereof.

The domain structure of human biglycan is shown in FIG. 5C. Biglycan is one of a family of small leucine-rich repeat proteins (Hocking et al. (1998) *Matrix Biol.* 17: 1). It consists of a pre-pro-peptide that is not present in the mature polypeptide. This domain is followed by a short unique sequence with two chondroitin sulfate attachment sites (shown as stacked beads in the Figure). There are two pairs and one pair of disulfide-linked cysteines at the amino and carboxyl-terminal domains, respectively. Finally, the bulk of the protein is comprised of 10 (or 11 depending upon the classification of the region within the carboxyl-terminal cysteine pair) leucine-rich repeats. The position of the three Torpedo peptides relative to the human sequence is indicated by horizontal lines.

Example 5

Chondroitin Sulfate Chains of Biglycan are Necessary for Binding of Biglycan to α-Dystroglycan Mammalian biglycan is often substituted with chondroitin sulfate. To determine if Torpedo biglycan is also a chondroitin sulfate proteoglycan and whether glycosylation is important for its binding to α-dystroglycan, DAG-125 was digested with various glycosidases and glycosaminoglycanases and the products were analyzed by α-dystroglycan ligand blot overlay with $^{35}$S-DG345-653.

Enzyme treatments were carried out on alkaline-extracted Torpedo electric organ synaptic membrane proteins at 37° C. overnight. Enzymes, final concentration, supplier and catalog numbers are listed in Table I. All reactions were performed in the protease inhibitors present in SEN Buffer, with the addition of 1 mM EDTA, 10 mM N-ethylmaleimide, and 0.8% mouse serum albumin. Chondroitinases (all forms) were buffered with 100 mM Tris-acetate (pH 8.0). Hyaluronidase and keratanase were buffered with 50 mM sodium acetate (pH 5.0). Heparinases (I, II, and III), chondro-4-sulfatase and chondro-6-sulfatase were buffered with 10 mM $NaPO_4$ (pH 7.4). N-Glycanase, O-glycanase, neuraminidase, α-N-acetylgalactosaminidase, β-N-acetylglucoasaminidase were buffered with 50 mM Tris HCl (pH 7.3). Control treatments included buffers and protease inhibitors without added enzymes.

Figure 6:
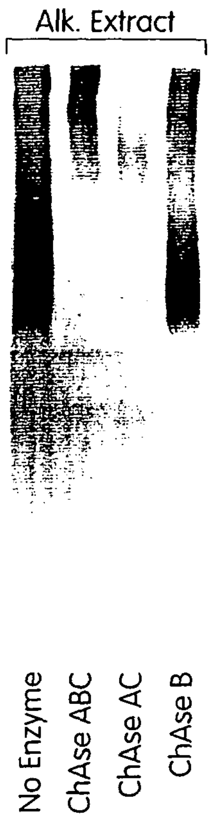
FIG. 6 shows the results of an analysis of Torpedo DAG-125 glycosylation.

The results are shown in FIG. 6 and in Table I.

TABLE I

| Enzyme | Inhibit Binding? | Enzyme (Units/ mL) | ConcSource | Cat. # |
|---|---|---|---|---|
| Chondroitinase ABC | + | 0.5 | Sigma | C-2905 |
| Chondroitinase ABC + 5 mM $ZnCl_2$ | – | 0.5 | Sigma | C-2905 |
| Chondroitinase ABC, Protease-free | + | 0.5 | Sigma | C-3667 |
| Chondroitinase ABC, Protease-free | + | 0.5 | Roche | 1080717 |
| Chondroitinase AC | + | 0.5 | Sigma | C-2780 |
| Chondroitinase B | +/– | 25 | Sigma | C-8058 |
| Heparinase I | – | 25 | Sigma | H-2519 |
| Heparinase II | – | 5 | Sigma | H-3812 |
| Heparinase III (Heparitinase) | – | 5 | Sigma | H-8891 |
| Chondro-4-sulfatase | +/– | 0.5 | Sigma | C-2655 |
| Chondro-6-sulfatase | – | 0.5 | Sigma | C-2655 |

TABLE I-continued

| Enzyme | Inhibit Binding? | Enzyme (Units/mL) | ConcSource | Cat. # |
|---|---|---|---|---|
| Keratanase | – | 0.02 | Roche | 982954 |
| α-N-acetylgalactosaminidase | – | 2 | Sigma | A-9763 |
| β-N-acetylglucoasaminidase | – | 8 | Sigma | A-2264 |
| N-Glycanase | – | 15 | Genzyme | N-Gly-1 |
| O-Glycanase | – | 0.03 | Genzyme | B2950 |
| Neuraminidase | – | 1 | Genzyme | NSS-1 |

The results indicate that removal of chondroitin sulfate side chains abolished the binding to α-dystroglycan. Chondroitinase B (specific for dermatan sulfate) had a much smaller effect compared to chondroitinases which removed chondroitin sulfate A and C. No other glycosidase or glycosaminoglycanase treatment had a detectable effect on α-dystroglycan binding (see Table I). Several lines of evidence indicate that the effects of chondroitinase digestion are due to chondroitinase activity and not to contaminating proteases: 1) the digestions were performed in a cocktail of protease inhibitors; 2) the same result was seen with four different preparations of chondroitinase, including two which had been affinity purified to remove proteases; and 3) the effect was prevented by addition of 5 mM $Zn^{2+}$, an inhibitor of chondroitinase but not of proteases.

To further investigate the binding properties of biglycan, the binding of α-dystroglycan to biglycan derived from a variety of sources, as well as to decorin, a small leucine-rich proteoglycan that is about 50% identical to biglycan, were investigated.

Figure 7:
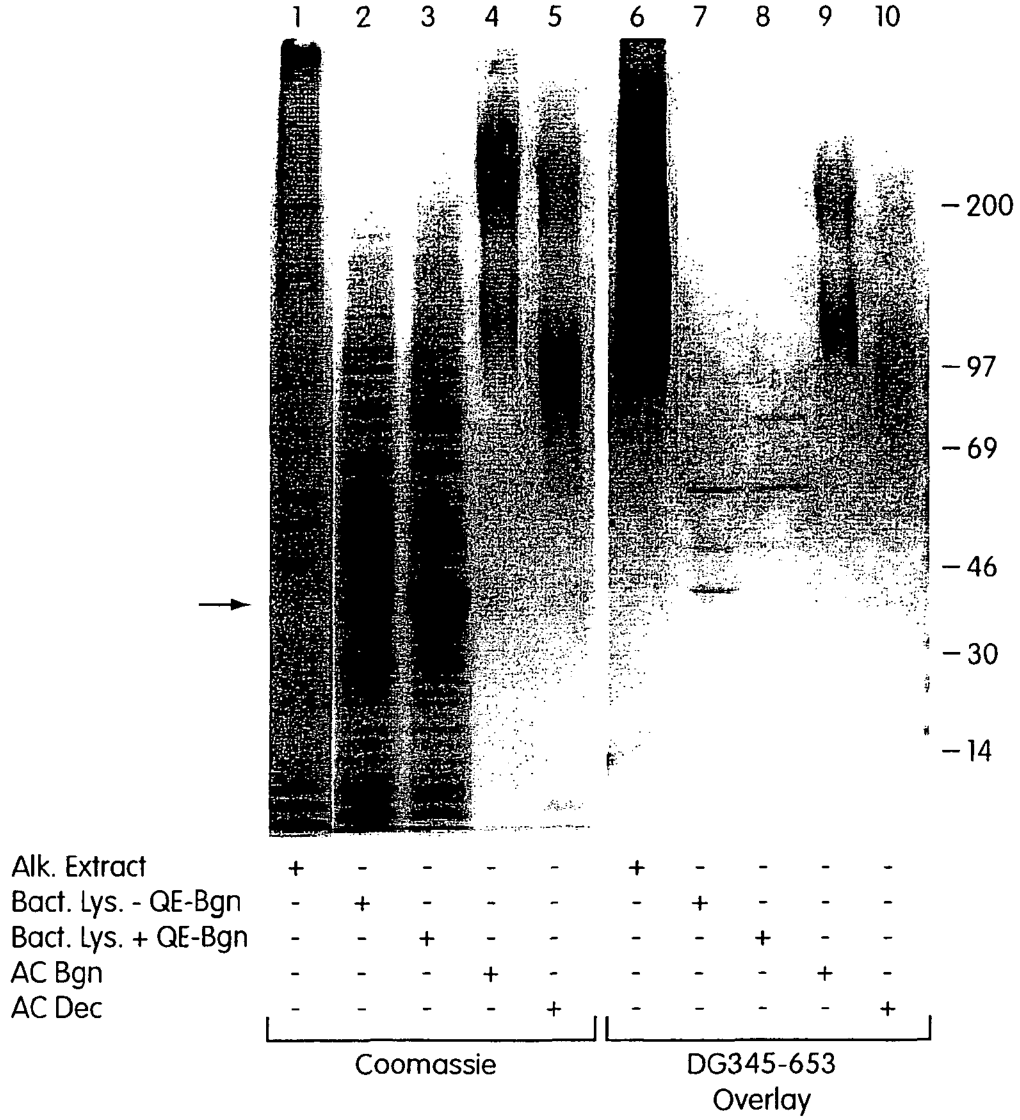
FIG. 7 shows that the binding of dystroglycan to biglycan is dependent upon specific chondroitin sulfate side chains. QE-Bgn is bacterially expressed biglycan core. AC stands for articular cartilage.

Biglycan (or decorin) were analyzed by SDS-PAGE and Coomassie Brilliant Blue staining for protein (lanes 1-5 of FIG. 7) or blot overlay assay for dystroglycan binding (lanes 6-10 of FIG. 7): lanes 1, 6: alkaline extract of Torpedo synaptic membranes (1 μg total protein, of which biglycan is estimated to be <2%); lanes 2, 7: lysate of non-induced bacteria; lanes 3, 8: lysate of induced bacteria expressing recombinant human biglycan (QE-Bgn; prominent band at ~37 kD-arrow); lanes 4, 9: biglycan purified from bovine articular cartilage (4 μg; Sigma); lanes 5, 10: decorin purified from bovine articular cartilage (4 μg; Sigma). The results indicate that biglycan present in electric organ binds dystroglycan much more strongly then biglycan or decorin purified from articular cartilage (compare Coomassie staining to dystroglycan overlay).

The recombinant human biglycan was produced as follows. P16, a cloning plasmid consisting of Bluescript containing a cDNA encoding human biglycan (SEQ ID NO: 9) was provide by Larry Fisher (National Institute of Dental Research, National Institutes of Health) (Fisher et al. (1989), supra). The sequence encoding the mature secreted peptide (amino acids 1-343) was amplified by PCR and subcloned into the bacterial expression vector pQE9 (Qiagen, Valencia, Calif.). The resulting plasmid, pQE-biglycan, adds the sequence MRGSHHHHHHGS (SEQ ID NO: 10) to the amino terminus. Recombinant protein was produced in *E. coli* strain M15[pREP4]. Uninduced bacteria provide control protein. Induced or non-induced bacteria were isolated by centrifugation and resuspended in SDS-PAGE sample buffer for analysis by ligand blot overlay. Thus, bacterially-expressed biglycan, which contains no chondroitin sulfate side chains, did not bind α-dystroglycan (FIG. 7), consistent with a requirement for chondroitin sulfate chains. Biglycan purified from articular cartilage bound α-dystroglycan poorly, even at >100-fold higher loading than that used for Torpedo biglycan analysis. These findings indicate that specific chondroitin sulfate chains are required to mediate α-dystroglycan binding to biglycan.

Thus, biglycan from Torpedo synaptic membranes is substituted with chondroitin sulfate chains, which are predominantly chondroitin sulfate A and/or C, and chondroitin sulfate substitution of biglycan is necessary for binding to dystroglycan.

Example 6

Biglycan Binds to Sarcoglycan Components

This Example describes that biglycan core binds to alpha- and to gamma sarcoglycans and that biglycan proteoglycan also binds to gamma-sarcoglycan, and that decorin failed to bind to any of the sarcoglycans (no detectable level of binding was observed).

The binding of biglycan and decorin to the different components of sarcoglycan of the DAPC was investigated by overlay assay using recombinantly produced human sarcoglycans, on biglycan proteoglycan (core and side chains), biglycan core (no side chains), decorin proteoglycan (core and side chains), decorin core (no side chains), a hybrid between biglycan and decorin core (the “hybrid” with side chains), and Torpedo electric organ membrane fraction (TEOM). The hybrid contained the first 30 amino acids of human biglycan (cysteine rich domain) and the remaining portion of the biglycan molecule was swapped with that of decorin.

The sarcoglycans were produced by in vitro transcription and translation using a Promega TNT kit, as described in Ahn and Kunkel (1995) *J. Cell Biol.* 128: 363. The biglycan and decorin core polypeptide and proteoglycan were produced recombinantly by vaccinia-virus infection of rat osteosarcoma cells, as described in Hocking et al. (1996) J. Biol. Chem. 271:19571. Briefly, the cDNA sequence encoding the mature core protein of human biglycan ligated to a polyhistidine fusion cassette under the control of T7 promoter was inserted into the pBGN4 vector. An encephalomyocarditis virus untranslated region was inserted downstream of the T7 promoter to facilitate cap-independent ribosome binding and thereby increases translation efficiency up to 10-fold. The fusion cassette encodes the canine insulin signal sequence (INS), six consecutive histidine residues (POLYHIS), and the factor Xa recognition site (Xa). A recombinant vaccina virus, vBGNA, encoding the T7 regulated BGN4 construct, was generated by a homologous recombination event between wild-type vaccinia virus and thymidine kinase flanking sequences in the plasmid, pBGN4. There are two extra amino acids between the polyhistidine sequence and the Factor Xa site and two extra amino acids between the Factor Xa site and the start of the mature core protein sequence of biglycan. Thus, the vector contains from 5' to 3': EMC UTR-INS-POLYHIS-[Glu-Ser]-Xa-[Leu-Glu]-mature biglycan devoid of the biglycan signal sequence and propeptide sequence). The biglycan that is produced from this system is a mixture containing proteoglycan biglycan and biglycan devoid of glycaosaminoglycan chains (“core biglycan”).

The overlay assays were preformed as described above for DAG-125.

Figure 8A:
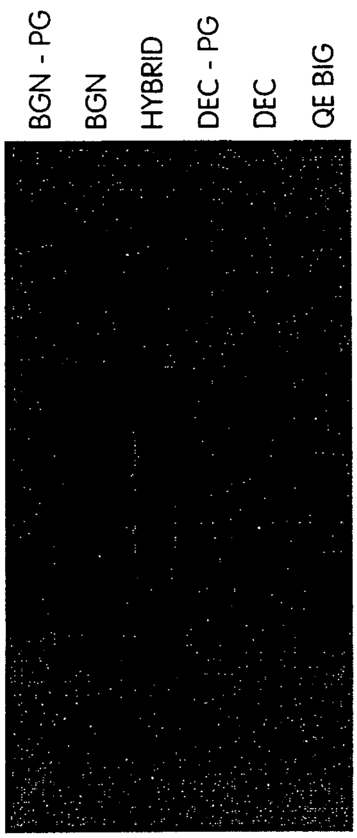
FIG. 8 A-C show overlay assays blots containing biglycan proteoglycan (BGN-PG), biglycan core (BGN), a biglycan-decorin hybrid (Hybrid), decorin proteoglycan (DEC-PG), decorin (DEC), bacterially produced biglycan (QE-BIG), and Torpedo electric organ membrane fraction (TEOM), which were incubated with $^{35}S$ labeled alpha-sarcoglycan (FIG. 8A), gamma-sarcoglycan (FIG. 8B), and delta-sarcoglycan (FIG. 8C).
Figure 8B:
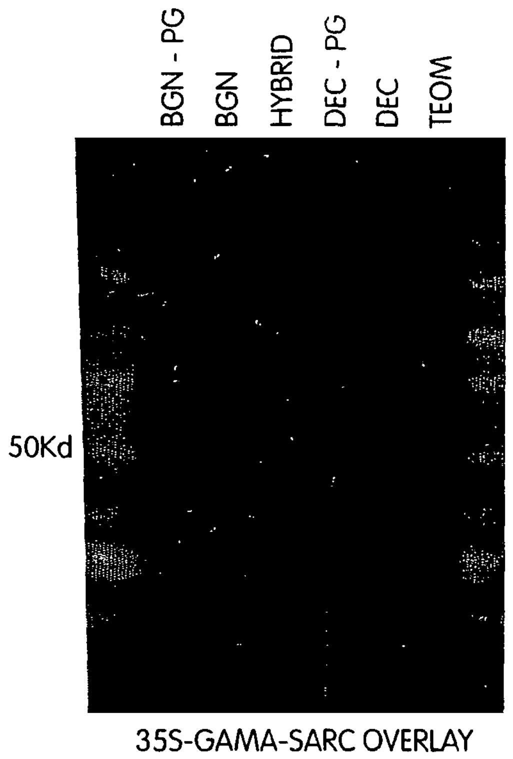
Figure 8C:
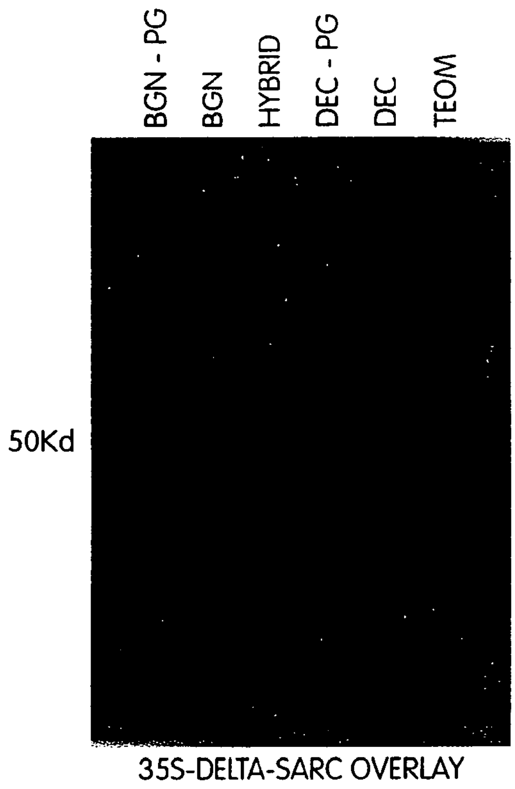

The results, which are shown as FIGS. 8 A-C, indicate the following: α-sarcoglycan binds to biglycan core and to the hybrid; γ-sarcoglycan binds to biglycan core, to biglycan proteoglycan and very weakly to the hybrid; and 8-sarcoglycan binds to biglycan core very weakly.

Thus, biglycan binds to -sarcoglycan via its core peptide. Furthermore, since the hybrid binds to -sarcoglycan, but that decorin does not bind to it, binding of biglycan to α-sarcoglycan occurs through the N-terminal 30 amino acids of biglycan, i.e., the region that includes the cysteine-rich region, but no leucine-rich repeats. In addition, the results indicate that glycosylation of sarcoglycan is not necessary for its binding to biglycan.

Human biglycan was also shown to bind to native alpha- and gamma-sarcoglycan in solution. This was demonstrated by isolating native human alpha- and gamma-sarcoglycan by detergent extraction of cultured mouse myotubes, incubating the extracts with recombinant human core biglycan prepared as described above, and then immunoprecipitating the resulting complexes were then immunoprecipitated with antibodies to alpha-sarcoglycan (vector laboratories). The immunoprecipitates were then resolved by SDS-polyacrylamide gel electrophoresis and western blotted with antibodies to biglycan. The anti-biglycan antibody was raised against a bacterially-produced biglycan fusion protein. The results, which are shown in FIG. 8D, show that native sarcoglycans alpha and gamma bind to biglycan.

Example 7

Biglycan is Expressed at Synaptic and Non-Synaptic Regions and is Up-Regulated in Dystrophic Muscle Previous reports have shown that biglycan mRNA and protein are expressed in muscle (Bianco, et al. (1990) *J. Histochem Cytochem.* 38: 1549; Bosse, et al. (1993) *J. Histochem. Cytochem.* 41: 13). Since the biglycan that was used in the above-described Examples was obtained from synaptic membranes, it was investigated whether biglycan is also expressed at the neuromuscular junction.

Frozen sections of normal adult mouse muscle were double-labeled with α-bungarotoxin (Bgtx; to localize AChRs) and antibodies to biglycan. Cryostat sections (10 μm) of leg muscle from fresh-frozen wild-type (C57 BL) mice were mounted on slides, fixed, and treated with chondroitinase essentially as described in (Bianco, P., et al., 1990, *J Histochem Cytochem.* 38:1549). Primary antibodies were anti-biglycan (LF-106; generously provided by L. Fisher) diluted in PBS containing 5% BSA, 1% normal goat or horse serum, and 0.1% Triton X-100. Incubation in primary antibodies or non-immune control serum proceeded overnight at 4° C. Except where noted, all subsequent steps were performed at room temperature. Bound antibodies were detected with Cy3-labelled anti-rabbit Ig (Jackson Laboratories, West Grove, Pa.). For double-labelling, sections were first fixed for 5 min in 1% formaldehyde, rinsed and incubated in fluorescein-conjugated α-bungarotoxin (Molecular Probes, Eugene Oreg.) for 1 hr. The sections were then washed, fixed, treated with chondroitinase and stained for biglycan as described above. Sections were air-dried, mounted in Citifluor (Ted Pella, Redding, Calif.) and examined on a Nikon Eclipse microscope. Images were acquired on a cooled CCD camera using IP Lab Spectrum software and then imported to Adobe Photoshop.

Figure 9:
FIG. 9 shows biglycan expression at the neuromuscular junction.

The results, which are shown in FIG. 9, indicate that biglycan immunoreactivity is distributed over the entire periphery of the myofibers and synapses, and that it is also concentrated at some neuromuscular junctions.

Figure 10:
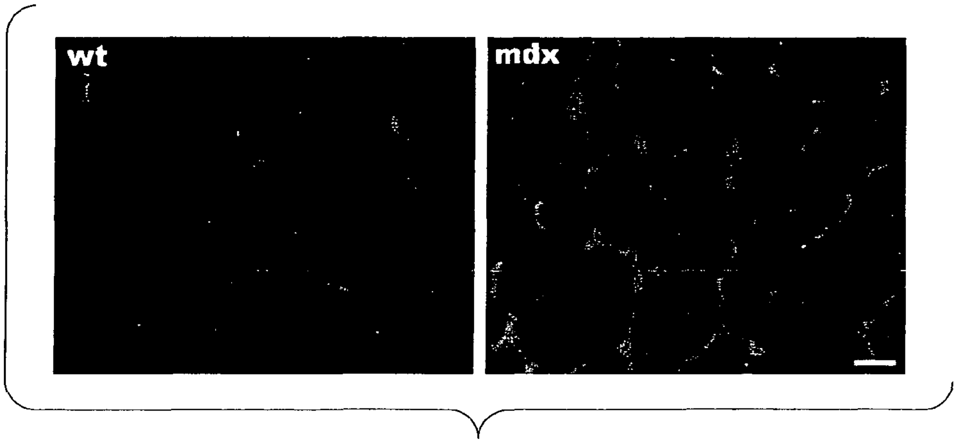
FIG. 10 shows the upregulation of biglycan expression in wild type (wt) and dystrophic (mdx) muscle.

Since biglycan binds to a component of the DAPC, it was investigated whether or not its expression was altered in a mouse model of muscular dystrophy in which dystrophin is absent, i.e., the mdx mouse. Adult mice, which contain almost exclusively regenerated muscle fibers that survive due to utrophin compensation were investigated (Grady, et al. (1997) *Cell* 90: 729). Frozen sections of normal and mdx muscle from 6 wk old mice were mounted on the same slides and immunostained for biglycan as described above. Immunostaining revealed that the level of biglycan expressed in mdx muscle is elevated compared to control animals (FIG. 10). These observations raise the possibility that biglycan could be part of the compensatory mechanism that allows survival of dystrophin negative muscle fibers.

Example 8

Biglycan Binds to the MuSK Ectodomain

This Example demonstrates that biglycan binds to other components of the synaptic membrane, in particular, the MuSK ectodomain.

Figure 11:
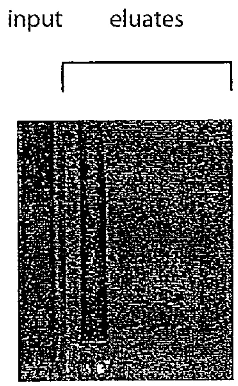
FIG. 11 shows the results of a co-immunoprecipitation of biglycan with recombinant MuSK-Fc.

Torpedo biglycan (DAG-125) was solubilized by alkaline extraction and neutralized, as described in Example 1, and incubated with protein A-agarose beads and with either human IgG (HIgG) or with human Fc fusion proteins containing the ectodomains of recombinant human MuSK (Glass et al. (1996) *Cell*; and Donzuela et al. (1995) *Neuron*), TIE-2, or TRK for co-precipitations. The results, which are shown in FIG. 11, indicate that Torpedo biglycan binds to the MuSK ectodomain, but not to IgG, nor to the two unrelated receptor tyrosine kinase ectodomains TIE-2 and TRK. It was also shown that MuSK solubilized from muscle membranes binds to Torpedo biglycan. Decorin was also shown to bind to MuSK.

Thus, DAG-125 binds to MuSK.

Example 9

Biglycan Preparations Potentiate Agrin-Induced AChR Clustering on Myotubes

This Example demonstrates that biglycan potentiates agrin-induced AChR clustering.

Primary chick myotubes were incubated for 20 hours with recombinant biglycan core (no GAG) with or without the addition of 1 unit (about 10 pM) of recombinant rat agrin isoform 12-4-8. Cultures incubated in 1 nM biglycan+agrin increased AChR clustering by an average of 50% over cultures incubated in 1 unit of agrin only. Higher concentrations of biglycan had no effect or possibly inhibited agrin-induced clustering. In another example, exogenous biglycan-enriched preparations (about 30% pure) were also found to potentiate agrin-induced AChR clustering when applied to cultured chick myotubes.

Thus, biglycan potentiates (50% increase) agrin-induced AChR clustering when present at about $10^{-9}$ M (i.e., about 1.4 nM). At higher concentrations ($10^{-8}$ M, $10^{-7}$ M, i.e., about 140 nM) biglycan inhibits agrin-induced AChR clustering. This was demonstrated on wild-type chick myotubes, which were prepared as described in Nastuk et al., 1991 (*Neuron* 7: 807-818), using either core or proteoglycan human recombinant biglycan, produced by the vaccinia system, described above. Thus, there is a biphasic effect of biglycan on agrin-induced AChR clustering.

Example 10

Biglycan and Decorin Induce Tyrosine Phosphorylation of MuSK

Figure 12:
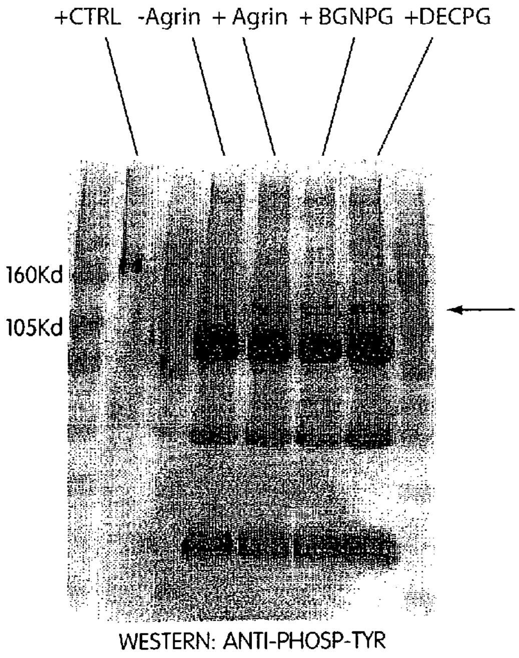
FIG. 12 is a Western blot containing cell extracts of cells incubated with or without agrin and with biglycan proteoglycan (BGNPG) or decoring proteoglycan (DECPG) incubated with anti-phosphotyrosine antibody.

The culture of chick myotubes with agrin resulted, as expected, in the stimulation of phosphorylation of MuSK. It was observed that the stimulation of chick myotubes with human biglycan proteoglycan, decorin-proteoglycan, biglycan core and decorin core (separately) also induce tyrosine phosphorylation of MuSK on muscle cells. Phosphorylation was determined by immunoprecipitation and Western blot using an anti-phosphotyrosine antibody. The biglycan and decorin proteoglycan and core were produced by the vaccinia system described above. The results are shown in FIG. 12.

Similarly to agrin-induced AChR clustering, agrin-induced MuSK phosphorylation was also shown to be biphasic: human biglycan core can either potentiate (at 1.4 nM) or inhibit (at 140 nM) agrin-induced MuSK phosphorylation in cultured C2C12 myotubes.

Example 11

Myotubes cultured from biglycan$^{-/o}$ mice show a defective response to agrin The role of biglycan in mediating agrin-induced AChR clustering was further proved by using biglycan knockout mice (biglycan$^{-/o}$) male mice).

Figure 13A:
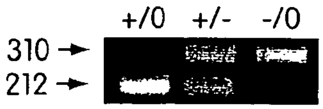
FIG. 13A shows a genotype analysis. PCR genotyping was performed on genomic DNA using primer pairs specific for mutant and wild type biglycan alleles (Xu et al. 1998). PCR products from a wild type (male; +/o), a heterozygote (female; +/−), and a knockout (male; −/o) are shown. Size of PCR products is indicated on left.

Biglycan$^{-/o}$ mice were generated by Marian Young at the NIH. PCR genotyping of the mice was performed on genomic DNA using primer pairs specific for mutant and wild type biglycan alleles (Xu et al. (1998) *Nat. Genet.* 20:78). PCR products from a wild type (male; +/o), a heterozygote (female; +/−), and a knockout (male; −/o) are shown in FIG. 13A.

Figure 13B:
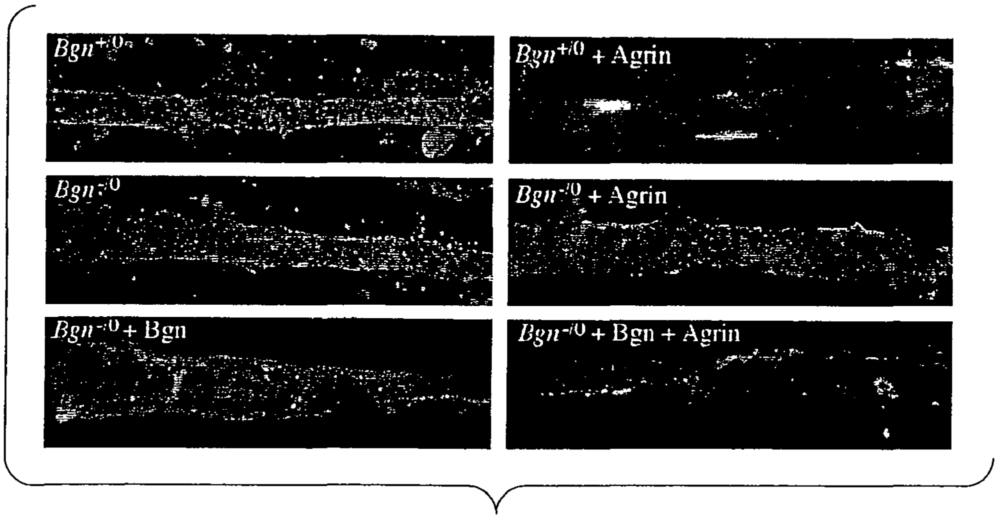
FIG. 13B shows defective agrin-induced AChR clustering in myotubes cultured from biglycan null mice and its rescue by addition of exogenous biglycan. A Bgn female (+/−) was mated to a Bgn male (+/o) and primary cultures were established from each male pup in the resulting litter. The genotype of each pup was determined as shown in FIG. 13A. Myotube cultures derived from each mouse were then treated either with or without recombinant agrin-4,8 for 18 hours. Myotubes were then labeled with rhodamine-a-bungarotoxin to visualize AChRs. Wild type myotubes show a robust AChR clustering response to agrin, while myotubes from biglycan−/o mice fail to cluster AChR in response to agrin. Exogenous biglycan (1.4 nM) restores the agrin-induced AChR clustering response.

A Bgn female (+/−) was mated to a Bgn male (+/o) and primary cultures were established from each male pup in the resulting litter. The genotype of each pup was determined as described in the previous paragraph. Myotube cultures derived from each mouse were then treated either with or without recombinant agrin 4,8 for 18 hours. Agrin 4,8 is an alternatively spliced variant, having a four amino acid insert at site Y and an eight amino acid insert at site Z (see, e.g., Iozzo R. I (1998) *Ann. Rev. Biochem.* 67:609, and Firns et al. (1993) Neuron 11:491). Myotubes were then labeled with rhodamine-1-bungarotoxin to visualize AChRs. As shown in FIG. 13B, the agrin-induced AChR clustering on the biglycan$^{-/o}$ myotubes is greatly reduced compared to those from wild type littermate controls. These results thus provide strong and direct evidence for a role of biglycan in agrin-induced AChR clustering.

Figure 13C:
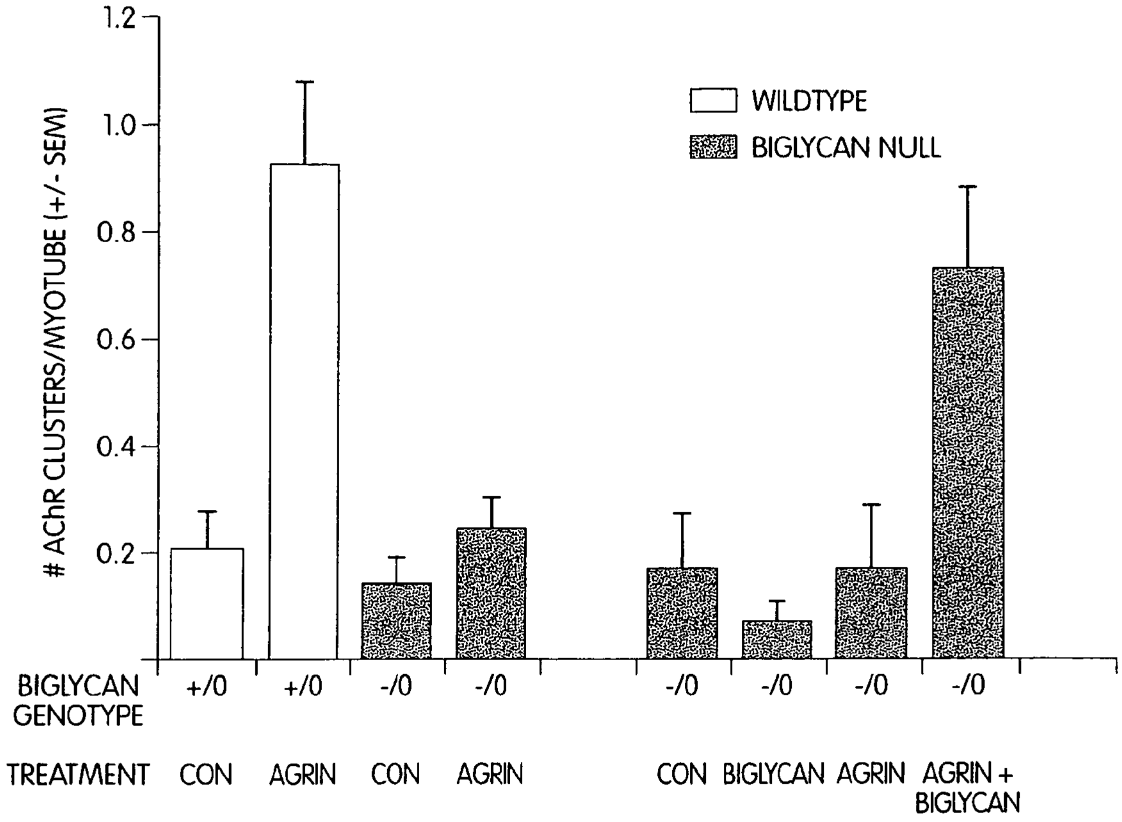
FIG. 13C shows quantification of AChR clustering. AChR clusters and myotubes were counted in a minimum of 10 fields for cultures treated either with (AGRIN) or without (Con) recombinant agrin4,8 in the presence of biglycan (1.4 nM) as indicated. A similar deficit in agrin-induced AChR clustering was observed in two other experiments.
Figure 14:
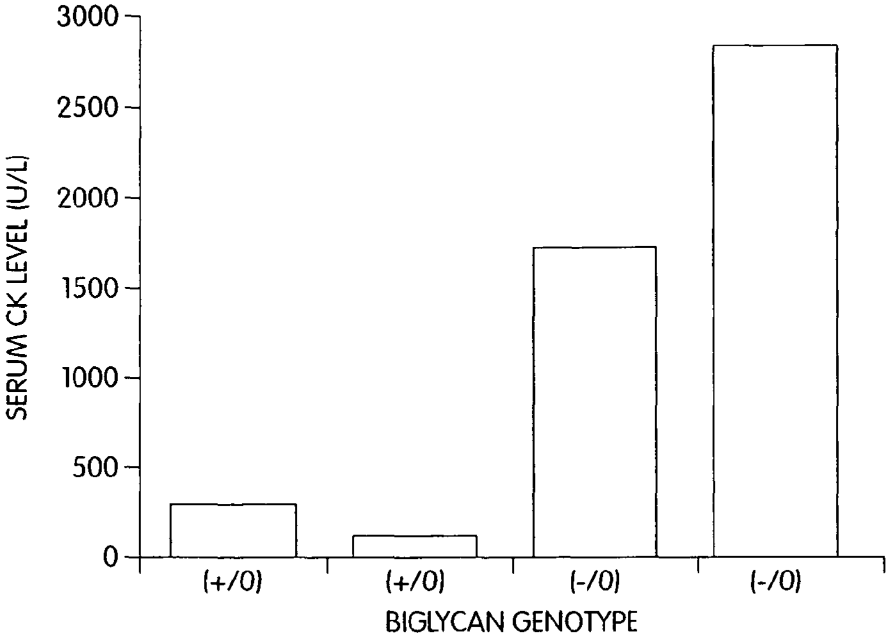
FIG. 14 shows the level of serum creatine kinase in wild type and biglycan knock out mice.

FIG. 13C shows a quantitation of AChR clustering. AChR clusters and myotubes were counted in a minimum of 10 fields for cultures treated either with (AGRIN) or without (Con) recombinant agrin 4,8.

Example 12

Recovery of Response to Agrin in Biglycan$^{-/o}$ Mice by the Addition of Recombinant Biglycan This example shows that the defective response of AChR aggregation in biglycan$^{-/o}$ mice in response to agrin can be rescued by the addition of exogenous recombinant human biglycan core.

This was demonstrated by adding 1.4 nM (0.05 micrograms/ml) of recombinant core human biglycan, produced in the vaccinia system described above, to the cultures of biglycan$^{-/o}$ myotubes described in Example 11. AchR clustering was measured as determined in Example 11.

The results, which are presented in FIG. 13B, indicate that the addition of biglycan core restores the response of biglycan$^{-/o}$ myotubes to agrin.

Thus, this experiment proves the importance of biglycan in agrin-induced AChR clustering. In addition, since this example was performed with core biglycan, i.e., with no proteoglycan side chains, this example demonstrates that the core is particularly important for the agrin-induced postsynaptic differentiation. This further demonstrates that biglycan affects a cell simply by contacting the cell with biglycan.

Example 13

Serum Creatine Kinase is Elevated in Biglycan Knockout Mice

Figure 15:
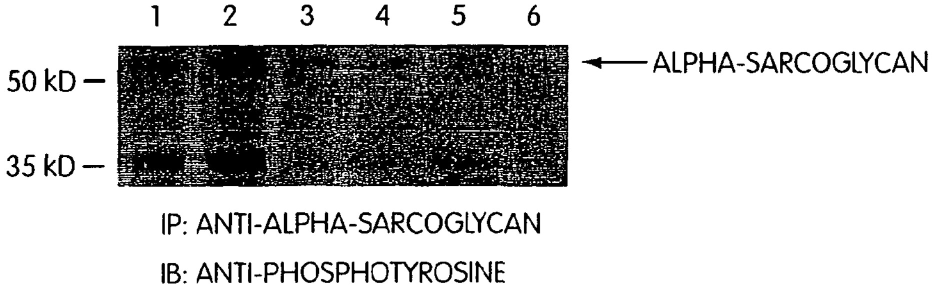
FIG. 15 shows that exogenous biglycan induces alpha-sarcoglycan phosphorylation in a MuSK dependent manner. Wild type C2C12 myotubes (lanes 1, 2, and 6) and MuSK null myotubes (lanes 3-5) were treated for thirty minutes as follows: lanes 1, 3, and 6, unstimulated; lanes 2 and 5, stimulated with a mixture of recombinant proteoglycan and core biglycan (produced in osteosarcoma cells; 1 mg/mL); lane 4, stimulated with agrin 12.4.8. The cultures were detergent extracted and alpha-sarcoglycan was immunoprecipitated, separated by SDS-PAGE, blotted, and probed with anti-phosphotyrosine antibody (lanes 1-5) or MIgG (lane 6). The addition of biglycan induced tyrosine phosphorylation of alpha-sarcoglycan and p35 in wild type C2C12 cells but not in MuSK knockout cells.

Serum creating kinase (CK) levels from four mice (two male, two female) ages 16 weeks old were assayed. As shown in FIG. 15, CK levels from biglycan knockout mice are about 10 fold greater than wild types. Sera from three other wild type female mice had similar CK levels as these wild type males.

Thus, although biglycan$^{-/o}$ mice do not show gross abnormalities (Xu et al. (1998) *Nat. Genet.* 20:78), the expression of dystrophin and utrophin are not grossly abnormal, and the synapses also appear grossly normal, they have an abnormally high CK level, relative to wild type animals. Such elevations are a hallmark of muscle cell damage, such as that seen in muscular dystrophy (Emery (1993) Duchenne Muscular Dystrophy Oxford Monographs on Medical Genetics. Oxford: New York. Oxford Univ. Press). In addition, these mice have leaky membranes, as judged by Evans Blue uptake, and show signs of muscle cell death and regeneration as judged by the presence of myofibers with centrally-located nuclei in the adult. Thus, these results indicate that the muscle cell plasma membrane is likely to be compromised in these animals. These observations, together with the restoration of agrin-induced AChR clustering in myotubes from biglycan$^{-/o}$ mice by the addition of biglycan, strongly suggest that the absence of biglycan or the presence of a defective biglycan results in defective muscle and/or nerve plasma membrane which can be restored by the addition of exogenous biglycan.

Example 14

Biglycan Core Stimulates Musk Dependent Tyrosine Phosphorylation of Alpha-Sarcoglycan and a 35 kD DAPC Component in Myotubes This example demonstrates that biglycan induces tyrosine phosphorylation of DAPC components and has therefore a signaling function.

Human biglycan was prepared using the vaccina system described above Wildtype myotubes or MuSK null myotubes were incubated for 30 minutes in the presence of 1 microgram/ml (27 nM) of a mixture of core and proteoglycan forms of human biglycan. The cultures were detergent extracted and alpha-sarcoglycan was immunoprecipitated, separated by SDS-PAGE, blotted, and probed with anti-phosphotyrosine antibody or MIgG. The results, which are presented in FIG. 15, show that the tyrosine phosphorylation of alpha-sarcoglycan is increased in the presence of biglycan in wild type cells, but not in MuSK null myotubes. In addition, it was observed that an unidentified 35 kD DAPC component was also phosphorylated in wild type cells but not in MuSK null myotubes. In addition, the results show that biglycan is capable of a signaling function, in the absence of agrin.

Equivalents

Those skilled in the art will recognize, or be able to ascertain using no more than routine experimentation, many equivalents of the specific embodiments of the invention described herein. Such equivalents are intended to be encompassed by the following claims.

We claims:

1. A pharmaceutical composition comprising:
(i) a polypeptide consisting of a sequence at least 80% identical to amino acids 38-365 of SEQ ID NO: 9, wherein the polypeptide is capable of binding to alpha-sarcoglycan and gamma-sarcoglycan and does not comprise glycosaminoglycan (GAG) side chains; and
(ii) a physiologically acceptable carrier or excipient;
wherein the composition is formulated as a sterile aqueous solution suitable for systemic administration or injection.

2. The pharmaceutical composition of claim 1, wherein the polypeptide consists of an amino acid sequence which is at least about 90% identical to amino acids 38-365 of SEQ ID NO: 9.

3. The pharmaceutical composition of claim 1, wherein the polypeptide consists of an amino acid sequence that is at least about 95% identical to amino acids 38-365 of SEQ ID NO: 9.

4. The pharmaceutical composition of claim 1, wherein the polypeptide is encoded by a nucleic acid which hybridizes to SEQ ID NO: 8 under stringent conditions of 6.0× sodium chloride/sodium citrate (SSC) at about 45° C. to a complementary strand of SEQ ID NO: 8.

5. The pharmaceutical composition of claim 1, wherein the polypeptide consists of an amino acid sequence that is at least about 99% identical to amino acids 38-365 of SEQ ID NO: 9.

6. The pharmaceutical composition of claim 1, which is formulated for injection.

7. The pharmaceutical composition of claim 6, which is formulated for intramuscular injection.

8. The pharmaceutical composition of claim 6, which is formulated for subcutaneous injection.

9. The pharmaceutical composition of claim 1, which is formulated for systemic administration.

10. The pharmaceutical composition of claim 1, which comprises a suspending, stabilizing, or dispersing agent.

11. A pharmaceutical composition comprising:
(i) a polypeptide consisting of a sequence at least 80% identical to amino acids 20-365 of SEQ ID NO: 9, wherein the polypeptide is capable of binding to alpha-sarcoglycan and gamma-sarcoglycan and does not comprise glycosaminoglycan (GAG) side chains; and
(ii) a physiologically acceptable carrier or excipient;
wherein the composition is formulated as a sterile aqueous solution suitable for systemic administration or injection.

12. The pharmaceutical composition of claim 11, wherein the polypeptide consists of an amino acid sequence which is at least about 90% identical to amino acids 20-365 of SEQ ID NO: 9.

13. The pharmaceutical composition of claim 11, wherein the polypeptide consists of an amino acid sequence which is at least about 95% identical to amino acids 20-365 of SEQ ID NO: 9.

14. The pharmaceutical composition of claim 11, wherein the polypeptide consists of an amino acid sequence which is at least about 99% identical to amino acids 20-365 of SEQ ID NO: 9.

15. The pharmaceutical composition of claim 11, which is formulated for injection.

16. The pharmaceutical composition of claim 15, which is formulated for intramuscular injection.

17. The pharmaceutical composition of claim 15, which is formulated for subcutaneous injection.

18. The pharmaceutical composition of claim 11, which is formulated for systemic administration.

* * * * *

SEQUENCE LISTING

<160> NUMBER OF SEQ ID NOS: 10

<210> SEQ ID NO 1
<211> LENGTH: 9
<212> TYPE: PRT
<213> ORGANISM: Torpedo sp.

<400> SEQUENCE: 1

Ile Gln Ala Ile Glu Phe Glu Asp Leu
1               5

<210> SEQ ID NO 2
<211> LENGTH: 9
<212> TYPE: PRT
<213> ORGANISM: Torpedo sp.

<400> SEQUENCE: 2

Leu Gly Leu Gly Phe Asn Glu Ile Arg
1               5

<210> SEQ ID NO 3
<211> LENGTH: 19
<212> TYPE: PRT
<213> ORGANISM: Torpedo sp.

<400> SEQUENCE: 3

Thr Ser Tyr His Gly Ile Ser Leu Phe Asn Asn Pro Val Asn Tyr Trp
1               5                   10                  15

Asp Val Leu

<210> SEQ ID NO 4
<211> LENGTH: 9
<212> TYPE: PRT
<213> ORGANISM: Homo sapiens

<400> SEQUENCE: 4

Ile Gln Ala Ile Glu Leu Glu Asp Leu
1               5

<210> SEQ ID NO 5
<211> LENGTH: 9
<212> TYPE: PRT
<213> ORGANISM: Homo sapiens

<400> SEQUENCE: 5

Leu Gly Leu Gly His Asn Gln Ile Arg
1               5

<210> SEQ ID NO 6
<211> LENGTH: 19
<212> TYPE: PRT
<213> ORGANISM: Homo sapiens

<400> SEQUENCE: 6

Ala Tyr Tyr Asn Gly Ile Ser Leu Phe Asn Asn Pro Val Pro Tyr Trp
1               5                   10                  15

Glu Val Gln

<210> SEQ ID NO 7
<211> LENGTH: 1685
<212> TYPE: DNA
<213> ORGANISM: Homo sapiens -continued

<400> SEQUENCE: 7
gagtagctgc tttcggtccg ccggacacac cggacagata gacgtgcgga cggcccacca 60
ccccagcccg ccaactagtc agcctgcgcc tggcgcctcc cctctccagg tccatccgcc 120
atgtggcccc tgtggcgcct cgtgtctctg ctggccctga gccaggccct gccctttgag 180
cagagaggct tctgggactt caccctggac gatgggccat tcatgatgaa cgatgaggaa 240
gcttcgggcg ctgacacctc aggcgtcctg gacccggact ctgtcacacc cacctacagc 300
gccatgtgtc ctttcggctg ccactgccac ctgcgggtgg ttcagtgctc cgacctgggt 360
ctgaagtctg tgcccaaaga gatctcccct gacaccacgc tgctggacct gcagaacaac 420
gacatctccg agctccgcaa ggatgacttc aagggtctcc agcacctcta cgccctcgtc 480
ctggtgaaca acaagatctc caagatccat gagaaggcct tcagcccact gcggaagctg 540
cagaagctct acatctccaa gaaccacctg gtggagatcc cgcccaacct acccagctcc 600
ctggtggagc tccgcatcca cgacaaccgc atccgcaagg tgcccaaggg agtgttcagc 660
gggctccgga acatgaactg catcgagatg ggcgggaacc cactggagaa cagtggcttt 720
gaacctggag ccttcgatgg cctgaagctc aactacctgc gcatctcaga ggccaagctg 780
actggcatcc ccaaagacct ccctgagacc ctgaatgaac tccacctaga ccacaacaaa 840
atccaggcca tcgaactgga ggacctgctt cgctactcca agctgtacag gctgggccta 900
ggccacaacc agatcaggat gatcgagaac gggagcctga gcttcctgcc caccctccgg 960
gagctccact tggacaacaa caagttggcc agggtgccct cagggctccc agacctcaag 1020
ctcctccagg tggtctatct gcactccaac aacatcacca aagtgggtgt caacgacttc 1080
tgtcccatgg gcttcggggt gaagcgggcc tactacaacg gcatcagcct cttcaacaac 1140
cccgtgccct actgggaggt gcagccggcc actttccgct gcgtcactga ccgcctggcc 1200
atccagtttg gcaactacaa aaagtagagg cagctgcagc caccgcgggg cctcagtggg 1260
ggtctctggg gaacacagcc agacatcctg atggggaggc agagccagga agctaagcca 1320
gggcccagct gcgtccaacc cagcccccca cctcaggtcc ctgaccccag ctcgatgccc 1380
catcaccgcc tctccctggc tcccaagggt gcaggtgggc gcaaggcccg gcccccatca 1440
catgttccct tggcctcaga gctgcccctg ctctcccacc acagccaccc agaggcaccc 1500
catgaagctt ttttctcgtt cactcccaaa cccaagtgtc caaagctcca gtcctaggag 1560
aacagtccct gggtcagcag ccaggaggcg gtccataaga atggggacag tgggctctgc 1620
cagggctgcc gcacctgtcc agaacaacat gttctgttcc tcctcctcat gcatttccag 1680
ccttg 1685

<210> SEQ ID NO 8
<211> LENGTH: 1104
<212> TYPE: DNA
<213> ORGANISM: Homo sapiens

<400> SEQUENCE: 8
atgtggcccc tgtggcgcct cgtgtctctg ctggccctga gccaggccct gccctttgag 60
cagagaggct tctgggactt caccctggac gatgggccat tcatgatgaa cgatgaggaa 120
gcttcgggcg ctgacacctc aggcgtcctg gacccggact ctgtcacacc cacctacagc 180
gccatgtgtc ctttcggctg ccactgccac ctgcgggtgg ttcagtgctc cgacctgggt 240
ctgaagtctg tgcccaaaga gatctcccct gacaccacgc tgctggacct gcagaacaac 300
gacatctccg agctccgcaa ggatgacttc aagggtctcc agcacctcta cgccctcgtc 360
ctggtgaaca acaagatctc caagatccat gagaaggcct tcagcccact gcggaagctg 420
cagaagctct acatctccaa gaaccacctg gtggagatcc cgcccaacct acccagctcc 480
ctggtggagc tccgcatcca cgacaaccgc atccgcaagg tgcccaaggg agtgttcagc 540
gggctccgga acatgaactg catcgagatg ggcgggaacc cactggagaa cagtggcttt 600
gaacctggag ccttcgatgg cctgaagctc aactacctgc gcatctcaga ggccaagctg 660
actggcatcc ccaaagacct ccctgagacc ctgaatgaac tccacctaga ccacaacaaa 720
atccaggcca tcgaactgga ggacctgctt cgctactcca agctgtacag gctgggccta 780
ggccacaacc agatcaggat gatcgagaac gggagcctga gcttcctgcc caccctccgg 840
gagctccact tggacaacaa caagttggcc agggtgccct cagggctccc agacctcaag 900
ctcctccagg tggtctatct gcactccaac aacatcacca aagtgggtgt caacgacttc 960
tgtcccatgg gcttcggggt gaagcgggcc tactacaacg gcatcagcct cttcaacaac 1020
cccgtgccct actgggaggt gcagccggcc actttccgct gcgtcactga ccgcctggcc 1080
atccagtttg gcaactacaa aaag 1104

<210> SEQ ID NO 9
<211> LENGTH: 368
<212> TYPE: PRT
<213> ORGANISM: Homo sapiens

<400> SEQUENCE: 9

```
Met Trp Pro Leu Trp Arg Leu Val Ser Leu Leu Ala Leu Ser Gln Ala
1               5                   10                  15

Leu Pro Phe Glu Gln Arg Gly Phe Trp Asp Phe Thr Leu Asp Asp Gly
            20                  25                  30

Pro Phe Met Met Asn Asp Glu Glu Ala Ser Gly Ala Asp Thr Ser Gly
        35                  40                  45

Val Leu Asp Pro Asp Ser Val Thr Pro Thr Tyr Ser Ala Met Cys Pro
    50                  55                  60

Phe Gly Cys His Cys His Leu Arg Val Val Gln Cys Ser Asp Leu Gly
65                  70                  75                  80

Leu Lys Ser Val Pro Lys Glu Ile Ser Pro Asp Thr Thr Leu Leu Asp
                85                  90                  95

Leu Gln Asn Asn Asp Ile Ser Glu Leu Arg Lys Asp Asp Phe Lys Gly
            100                 105                 110

Leu Gln His Leu Tyr Ala Leu Val Leu Val Asn Asn Lys Ile Ser Lys
        115                 120                 125

Ile His Glu Lys Ala Phe Ser Pro Leu Arg Lys Leu Gln Lys Leu Tyr
    130                 135                 140

Ile Ser Lys Asn His Leu Val Glu Ile Pro Pro Asn Leu Pro Ser Ser
145                 150                 155                 160

Leu Val Glu Leu Arg Ile His Asp Asn Arg Ile Arg Lys Val Pro Lys
                165                 170                 175

Gly Val Phe Ser Gly Leu Arg Asn Met Asn Cys Ile Glu Met Gly Gly
            180                 185                 190

Asn Pro Leu Glu Asn Ser Gly Phe Glu Pro Gly Ala Phe Asp Gly Leu
        195                 200                 205

Lys Leu Asn Tyr Leu Arg Ile Ser Glu Ala Lys Leu Thr Gly Ile Pro
    210                 215                 220

Lys Asp Leu Pro Glu Thr Leu Asn Glu Leu His Leu Asp His Asn Lys
225                 230                 235                 240

Ile Gln Ala Ile Glu Leu Glu Asp Leu Leu Arg Tyr Ser Lys Leu Tyr
```

-continued

```
                245                 250                 255

Arg Leu Gly Leu Gly His Asn Gln Ile Arg Met Ile Glu Asn Gly Ser
            260                 265                 270

Leu Ser Phe Leu Pro Thr Leu Arg Glu Leu His Leu Asp Asn Asn Lys
        275                 280                 285

Leu Ala Arg Val Pro Ser Gly Leu Pro Asp Leu Lys Leu Leu Gln Val
    290                 295                 300

Val Tyr Leu His Ser Asn Asn Ile Thr Lys Val Gly Val Asn Asp Phe
305                 310                 315                 320

Cys Pro Met Gly Phe Gly Val Lys Arg Ala Tyr Tyr Asn Gly Ile Ser
                325                 330                 335

Leu Phe Asn Asn Pro Val Pro Tyr Trp Glu Val Gln Pro Ala Thr Phe
            340                 345                 350

Arg Cys Val Thr Asp Arg Leu Ala Ile Gln Phe Gly Asn Tyr Lys Lys
        355                 360                 365


<210> SEQ ID NO 10
<211> LENGTH: 12
<212> TYPE: PRT
<213> ORGANISM: Plasmid pQE-biglycan

<400> SEQUENCE: 10

Met Arg Gly Ser His His His His His His Gly Ser
1               5                   10
```